US006933113B2

(12) United States Patent
Case et al.

(10) Patent No.: US 6,933,113 B2
(45) Date of Patent: Aug. 23, 2005

(54) MODULATION OF ENDOGENOUS GENE EXPRESSION IN CELLS

(75) Inventors: Casey C. Case, San Mateo, CA (US); Alan Wolffe, deceased, late of Orinda, CA (US), by Elizabeth Wolffe, legal representative; Fyodor Urnov, Richmond, CA (US); Albert Lai, Richmond, CA (US); Andrew Snowden, Richmond, CA (US); Siyuan Tan, Alameda, CA (US); Philip Gregory, El Cerrito, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 394 days.

(21) Appl. No.: 09/942,087

(22) Filed: Aug. 28, 2001

(65) Prior Publication Data

US 2002/0160940 A1 Oct. 31, 2002

Related U.S. Application Data

(63) Continuation-in-part of application No. 09/229,037, filed on Jan. 12, 1999, now Pat. No. 6,534,261.

(51) Int. Cl.[7] .......................... C12Q 1/68; C12N 15/63; C12N 15/11
(52) U.S. Cl. ...................... 435/6; 435/320.1; 435/69.1; 435/455; 435/458; 536/23.4
(58) Field of Search ...................... 435/6, 320.1, 69.1, 435/455, 458, 456; 536/23.4

(56) References Cited

U.S. PATENT DOCUMENTS

| | | | |
|---|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid et al. |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,602,009 A | 2/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,814,618 A | 9/1998 | Bujard et al. |
| 5,830,721 A | 11/1998 | Stemmer et al. |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,004,941 A | 12/1999 | Bujard et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,160,091 A | 12/2000 | Peukert et al. |
| 6,242,568 B1 | 6/2001 | Barbas, III et al. |
| 6,270,990 B1 | 8/2001 | Anderson et al. |

FOREIGN PATENT DOCUMENTS

| | | |
|---|---|---|
| EP | 0 875 567 | 4/1998 |
| WO | WO 92/02536 | 2/1992 |
| WO | WO 95/11922 | 5/1995 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/27092 | 6/1999 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |

(Continued)

OTHER PUBLICATIONS

Altincicek et al. "Interaction of the corepressor alien with DAX–1 is abrogated by mutations of DAX–1 involved in adrenal . . . " J. Biol. Chem. 275:7662–7667 (2000).

Cook et al. "Three conserved transcriptional repressor domains are a defining feature of the TIEG subfamily . . . " J. Biol. Chem. 274:29500–29504 (1999).

Crawford et al. "Nuclear receptor DAX–1 recruits nuclear receptor corepressor N–CoR . . . " Mol. Cell. Biol. 18:2949–2956 (1998).

(Continued)

Primary Examiner—John S. Brusca
(74) Attorney, Agent, or Firm—Sean Brennan; Dahna Pasternak

(57) ABSTRACT

Disclosed herein are methods and compositions for modulating expression of endogenous cellular genes using recombinant zinc finger proteins.

33 Claims, 13 Drawing Sheets

FOREIGN PATENT DOCUMENTS

| WO | WO 99/48909 | 9/1999 |
| --- | --- | --- |
| WO | WO 00/23464 | 4/2000 |
| WO | WO 00/27878 | 5/2000 |
| WO | WO 00/41566 | 7/2000 |
| WO | WO 00/42219 | 7/2000 |
| WO | WO 01/04296 A1 | 1/2001 |
| WO | WO 02/066640 A2 | 8/2002 |
| WO | WO 03/016496 A2 | 2/2003 |

OTHER PUBLICATIONS

Ito et al. "DAX-1 inhibits SF-1-mediated transactivation via a carboxy-terminal domain . . . " Mol. Cell. Biol. 17:1476-1483 (1997).

Lai et al. "RBP1 recruits the mSIN3-histone deacetylase complex to the pocket of . . . " Mol. Cell. Biol. 21:2918-2932 (2001).

LaPierre et al. "Identification of a novel transcriptional repressor encoded by human cytomegalovirus" J. Virology 75:6062-6069 (2001).

Maxon et al. "Ash1p is a site-specific DNA-binding protein that actively represses transcription" Proc. Natl. Acad. Sci. USA 98:1495-1500 (2001).

Sabbattini et al. "Binding of Ikaros to the lambda5 promoter silences transcription . . . " EMBO Journal 20:2812-2822 (2001).

Zazopoulos et al. "DNA binding and transcriptional repression by DAX-1 blocks steroidogenesis" Nature 390:311-315 (1997).

Zhang et al. "A conserved alpha-helical motif mediates teh interaction of Sp1-like transcriptional repressore . . . " Mol. Cell. Biol. 21:5041-5049 (2001).

Agarwal et al., "Stimulation of Transcript Elongation Requires Both the Zinc Finger and RNA Polymerase II Binding Domains of Human TFIIS," *Biochemistry* 30(31):7842-7851 (1991).

Antao et al., "A Thermodynamic Study of Unusually Stable RNA and DNA Hairpins," *Nuc. Acids. Res.* 19(21):5901-5905 (1991).

Barbas, C. F., "Recent Advances in Phage Display," *Curr. Opin. Biotech.* 4:526-530 (1993).

Barbas et al., "Assembly of Combinatorial Antibody Libraries on Phage Surfaces: The Gene III Site," *PNAS* 88:7978-7982 (1991).

Barbas et al., "Semisynthetic Combinatorial Antibody Libraries: A Chemical Solution to the Diversity Problem," *PNAS* 89:4457-4461 (1992).

Beerli et al., "Toward Controlling Gene Expression at Will: Specific Regulation of the erbB-2/HER-2 Promoter by Using Polydactyl Zinc Finger Proteins Constructed From Modular Building Blocks," *Proc. Natl. Acad. Sci. U.S.A.* 95:14628-14633 (1998).

Beerli et al., "Positive and negative regulation of endogenous genes by designed transcription factors," *Proc. Natl. Acad. Sci. U.S.A.* 97:1495-1500 (2000).

Bellefroid et al., "Clustered Organization of Homologous KRAB Zinc-Finger Genes With Enhanced Expression in Human T Lymphoid Cells," *EMBO J.* 12(4):1363-1374 (1993).

Berg, J.M., "DNA Binding Specificity of Steroid Receptors," *Cell* 57:1065-1068 (1989).

Berg, J.M., "Sp1 and the Subfamily of Zinc-Finger Proteins with Guanine-Rich Binding Sites," *PNAS* 89:11109-11110 (1992).

Berg et al., "The Galvanization of Biology: A Growing Appreciation for the Roles of Zinc," *Science* 271:1081-1085 (1996).

Berg, J.M., "Letting Your Fingers do the Walking," *Nature Biotechnology* 15:323 (1997).

Bergqvist et al., "Loss of DNA-binding and new Transcriptional Trans-Activation Function in Polyomavirus Large T-Angtigen with Mutation of Zinc Finger Motif," *Nuc. Acids Res.* 18(9):2715-2720 (1990).

Blaese et al., "Vectors in Cancer Therapy: How Will They Deliver?," *Cancer Gene Therapy* 2(4):291-297 (1995).

Bonde et al., "Ontogeny of the v-erbA Oncoprotein from the Thyroid Hormone Receptor: An Alteration in the DNA Binding Domain Plays a Role Crucial for verbA Function," *J. Virology* 65(4):2037-2046 (1991).

Caponigro et al., "Transdominant Genetic Analysis of a Growth Control Pathway," PNAS 95:7508-7513 (1998).

Celenza et al., "A Yeast Gene That Is Essential for Release from Glucose Repression Encodes a Protein Kinase," *Science* 233:1175-1180 (1986).

Cheng et al., "Identification of Potential Target Genes for Adrlp through Characterization of Essential Nucleotides in UASI," *J. Mol. Cellular Biol.* 14(6):3842-3852 (1994).

Cheng et al., "A Single Amino Acid Substitution in Zinc Finger 2 of Adrlp Changes its Binding Specificity at two Positions in UAS1,"*J. Mol. Biol.* 251:1-8 (1995).

Choo et al., A Role in DNA-Binding for the Linker Sequences of the First Three Zinc Fingers of TFIIIA *Nuc. Acids Res.* 21(15):3341-3346 (1993).

Choo et al., "Promoter-Specific Activation of Gene Expression Directed By Bacteriophage-Selected Zinc Fingers," *J. Mol. Biol.* 273:525-532 (1997).

Choo et al., "Designing DNA-Binding Proteins on the Surface of Filamentous Phage," *Curr. Opin. Biotechnology* 6:431-436 (1995).

Choo, Y., "Recognition of DNA Methylation by Zinc Fingers," *Nature Struct Biol.* 5(4):264-365 (1998).

Choo et al., "All Wrapped Up," *Nature Structural Biology* 5(4):253-255 (1998).

Choo, Y., "End Effects in DNA Recognition Code," *Nuc. Acids. Res.* 26(2):554-557 (1998).

Choo et al., Physical Basis of Protein-DNA Recognition Code, *Curr. Opin. Struct. Biol.* 7(1):117-125 (1997).

Choo et al., "Toward a Code for the Interactions of Zinc Fingers With DNA: Selection of Randomized Fingers Displayed on Phage," *Proc. Natl. Acad. Sci. U.S.A.* 91:11163-11167 (1994).

Choo et al., "Selection of DNA Binding Sites for Zinc Fingers using Randomized DNAs reveals Coded Interactions," *Proc. Natl. Acad. Sci. U.S.A.* 91:11168-11172 (1994).

Choo et al., "In vivo Repression by a Site-Specific DNA-Binding Protein Designed against an Onogenic Sequence," *Nature* 372:642-645 (1994).

Clark et al., "Zinc Fingers in *Caenorhabiditis elegans*: Finding Families and Probing Pathways," *Science* 282:2018-2022 (1998).

Corbi et al., "Synthesis of a New Zinc Finger Peptide: Comparison of Its "Code" Deduced and CASTing Derived Binding Sites," *FEBS Letters* 417:71-74 (1997).

Crozatier et al., "Single Amino Acid Exchanges in Separate Domains of the Drosophila Serendipity Zinc Finger Protein Cause Embroyonic and Sex Biased Lethality," *Genetics* 131:905-916 (1992).

Debs et al., Regulation of Gene Expression in Vivo by Liposome–Mediated Delivery of a Purified Transcription Factor, *J. Biological Chemistry* 265(18):10189–10192 (1990).

DesJardins et al., "Repeated CT Elements Bound by Zinc Finger Proteins Control the Absolute and Relative Activities of the Two Principal Human C–myc Promoters," *Mol. Cell. Biol.* 13(9):5710–5724 (1993).

Desjarlais et al., "Redesigning the DNA–Binding Specificity of a Zinc Finger Protein: A Data Base–Guided Approach," *Proteins: Structure, Function, and Genetics* 12(2):101–104 (1992).

Desjarlais et al., "Toward Rules Relating Zinc Finger Protein–Sequences and DNA Binding Perferences," *PNAS* 89:7345–7349 (1992).

Desjarlais et al., "Use of a Zinc–Finger Consensus Sequence Framework and Specificity Rules to Design Specific DNA Binding Proteins," *PNAS* 90:2256–2260 (1993).

Desjarlais et al., "Length–Encoded Multiplex binding Site Determination: Application to Zinc Finger Proteins," *PNAS* 91:11099–11103 (1994).

Dibello et al., "The Drosophila Broad–Complex Encodes a Family of Related Proteins Containing Zinc Fingers," *Genetics* 129:385–397 (1991).

Donze et al., "Activation of delta–globin gene expression by erythroid Krupple–like factor: a potential approach for gene therapy of sickle cell disease," *Blood* 88:4051–4057 (1996).

Elrod–Erickson et al., "High–Resolution Structures of Variant Zif268–DNA Complexes: Implications for Understanding Zinc Finger–DNA Recognition," *Structure* 6(4):451–464 (1998).

Elrod–Erickson et al., "Zif268 Protein–DNA Complex Refined at 1.6: a Model System for Understanding Zinc Finger–DNA Interactions," *Structure* 4(10):1171–1180 (1996).

Fairall et al., "The Crystal Structure of a Two Zinc–Finger Peptide Reveals an Extension to the Rules for Zinc–Finger/DNA Recognition," *Nature* 366:483–487 (1993).

Frankel et al., "Fingering Too Many Proteins," *Cell* 53:675 (1988).

Friesen et al., "Phage Display of RNA Binding Zinc Fingers from Transcription Factor IIA," *J. Biological Chem.* 272(17):10994–10997 (1997).

Friesen et al., "Specific RNA Binding Proteins Constructed from Zinc Fingers," *Nature Structural Biology* 5(7):543–546 (1998).

Ghosh "A relational database of transcription factors," *Nucleic Acids Res* 18:1749–1756 (1990).

Gillemans et al., "Altered DNA Binding Specificity Mutants of EKLF and Spl Show that EKLF is an Activator of the b–globin Locus Control Region in vivo," *Genes and Development* 12:2863–2873 (1998).

Gogos et al., "Recognition of Diverse Sequences by Class I Zinc Fingers: Asymmetries and Indirect Effects on Specificity in the Interaction Between CF211 and A+T–Rich Sequences Elements," *PNAS* 93(5):2159–2164 (1996).

Gossen et al., "Tight Control of Gene Expression in Mammalian Cells by Tetracycline–Responsive Promoter," *PNAS* 89:5547–5551 (1992).

Greisman & Pabo, "A General Strategy for Selecting High–Affinity Zinc Finger Proteins for Diverse DNA Target Sites," *Science* 275:657–661 (1997).

Hall et al., "Functional Interaction between the Two Zinc Finger Domains of the V–erbA Oncoprotein," *Cell Growth & Differentiation* 3:207–218 (1992).

Hamilton et al., "High Affinity Binding Sites for the Wilms' Tumor Suppressor Protein WTI," *Nuc. Acids. Res.* 23(2):277–284 (1995).

Hamilton et al., "Comparison of the DNA Binding Characteristics of the Related Zinc Finger Proteins WT1 and EGR1," *Biochemistry* 37:2051–2058 (1998).

Hanas et al., "Internal Deletion Mutants of Xenopus Transcription Factor IIIA," *Nuc. Acids. Res.* 17(23):9861–9870 (1989).

Hayes et al., "Locations of Contacts Between Individual Zinc Fingers *Xenopus laevis* Transcription Factor IIIA and the Internal Control Region of a 5S RNA Gene," *Biochemistry* 31:11600–11605 (1992).

Heinzel et al., "A Complex containing N–CoR, MSin3 and Histone Deacetylese Medates Transcriptional Repression," *Nature* 387:43–48 (1997).

Hirst et al., "Discrimination of DNA Response Elements for Thyroid Hormone and Estrogen is Dependent of Dimmerization of Receptor DNA Binding Domains," *PNAS* 89:5527–5531 (1992).

Hoffman et al., "Structures of DNA–Binding Mutant Zinc Finger Domains: Implications for DNA Binding," *Protein Science* 2:951–965 (1993).

Imhof et al., "Transcriptional Regulation of the AP–2alpha Promoter by BTEB–1 and AP–2REP, a Novel WT–1/EGR–Related Zinc Finger Repressor," *Molecular and Cellular Biology* 19(1):194–204 (1999).

Isalan et al., "Synergy Between Adjacent Zinc Fingers in Sequence–Specific DNA Recognition," *PNAS* 94(11):5617–5621 (1997).

Isalan et al., "Comprehensive DNA Recognition Through Concerted Interactions from Adjacent Zinc Fingers," *Biochemistry* 37:12026–12033 (1998).

Jacobs, G.H., "Determination of the Base Recognition Positions of Zinc Fingers From Sequence Analysis," *EMBO J.* 11(12):4507–4517 (1992).

Jamieson et al. "A Zinc Finger Directory for High–Affinity DNA Recognition," *PNAS* 93:12834–12839 (1996).

Jamieson et al., "In Vitro Selection of Zinc Fingers with Altered DNA–Binding Specificity," *Biochemistry* 33:5689–5695 (1994).

Jones et al., "Replacing the complementarity–determining regions in a human antibody with those from a mouse" *Nature* 321:522–525 (1986).

Julian et al., "Replacement of His23 by Cys in a Zinc Finger of HIV–1NCp7 Led to a Change in 1H NMR–Derived 3D Structure and to a Loss of Biological Activity," *FEBS Letters* 331(1,2):43–48 (1993).

Kamiuchi et al., "New Multi Zinc Finger Protein: Biosynthetic Design and Characteristics of DNA Recognition," *Nucleic Acids Symposium Series* 37:153–154 (1997).

Kang et al., "Zinc Finger Proteins as Designer Transcription Factors," *J. Biol. Chem.* 275(12):8742–8748 (2000).

Kim et al., "Serine at Position 2 in the DNA Recognition Helix of a Cys2–His2 Zinc Finger Peptide is Not, in General, Responsible for Base Recognition," *J. Mol. Biol.* 252:1–5 (1995).

Kim et al., "Site–Specific Cleavage of DNA–RNA Hybrids by Zinc Finger/FokI Cleavage Domain Fusions," *Gene* 203:43–49 (1997).

Kim et al., "A 2.2 A° Resolution Crystal Structure of a Designed Zinc Finger Protein Bound to DNA," *Nat. Struct. Biol.* 3(11):940–945 (1996).

Kim et al., "Design of TATA Box–Binding Protein/Zinc Finger Fusions for Targeted Regulation of Gene Expression," *PNAS* 94:3616–3620 (1997).

Kim et al., "Hybrid Restriction Enzymes: Zinc Finger Fusions Fok I Cleavage Domain," *PNAS* 93:1156–1160 (1996).

Kim et al. "Transcriptional repression by zinc finger peptides. Exploring the potential for applications in gene therapy" *J. Biol. Chem.* 272:29795–29800 (1997).

Kim et al. "Getting a handhold on DNA: design of poly–zinc finger proteins with femtomolar dissociation constants," *Proc. Natl. Acad. Sci. USA* 95:2812–2817 (1998).

Kinzler et al., "The GLI Gene is Member of the Kruppel Family of Zinc Finger Proteins," *Nature* 332:371–374 (1988).

Klug, A., "Gene Regulatory Proteins and Their Interaction with DNA," *Ann. NY Acad. Sci.* 758:143–160 (1995).

Klug et al., "Protein Motifs 5: Zinc Fingers," *FASEB J.* 9:597–604 (1995).

Klug, "Zinc Finger Peptides for the Regulation of Gene Expression," *J. Mol. Biol.* 293:215–218 (1999).

Kothekar, "Computer Simulation of Zinc Finger Motifs from Cellular Nucleic Acid Binding Proteins and Their Interaction with Consensus DNA Sequences," *FEBS Letters* 274(1,2):217–222 (1990).

Kriwacki et al., "Sequence–specific recognition of DNA by zinc–finger peptides derived from the transcription factor Sp–1," *Proc. Natl. Acad. Sci. USA* 89:9759–9763 (1992).

Kulda et al., "The Regulatory Gene areA Mediating Nitrogen Metabolite R in *Aspergillus nidulans* Mutations Affecting Specificity of Gene Activation Alter a Loop Residue of Putative Zinc Finger," *EMBO J.* 9(5):1355–1364 (1990).

Laird–Offringa et al., "RNA–Binding Proteins Tamed," *Nat. Structural Biol.* 5(8):665–668 (1998).

Liu et al., "Design of Polydactyl Zinc–Finger Proteins for Unique Addressing Within Complex Genomes," *Proc. Natl. Acad. Sci. U.S.A.* 94:5525–5530 (1997).

Liu et al., "Transcription Factor EGR–1 Suppresses the Growth and Transformation of Human HT–1080 Fibrosarcoma Cells by Induction of Transforming Growth Factor Beta 1," *Proc. Natl. Acad. Sci. U.S.A.* 93(21):11831–11836 (1996).

Liu et al., "Regulation of an Endogenous Locus Using a Panel of Designed Zinc Finger Proteins Targeted to Accessible Chromatin Regions: Activation of Vascular Endothelial Growth Factor A," *Journal of Biological Chemistry* 276(14):11323–11334 (2001).

Mandel–Gutfreund et al., "Quantitative Parameters for Amino Acid–Base Interaction: Implication for Predication of Protein–DNA Binding Sites," *Nuc. Acids Res.* 26(10):2306–2313 (1998).

Margolin et al., "Kruppel–Associated Boxes are Potent Transcriptional Repression Domains," *PNAS* 91:4509–4513 (1993).

Mizushima et al., "pEF–BOS, a Powerful Mammilian Expression Vector," *Nuc. Acids. Res.* 18(17):5322 (1990).

Mukhopadhyay et al. "The von Hippel–lindau Tumor Suppressor Gene Product Interacts with Sp 1 to Repress Vascular Endothelial Growth Factor Promoter Activity" *Mol. Cell. Biol.* 17(9):5629–5639 (1997).

Nakagama et al., "Sequence and Structural Requirements for High–Affinity DNA Binding by the WT1 Gene Product," *Molecular and Cellular Biology* 15(3):1489–1498 (1995).

Nardelli et al., "Zinc Finger–DNA Recognition: Analysis of Base Specificity by Site–Directed Mutagenesis," *Nucleic Acids Research* 20(16):4137–4144 (1992).

Nardelli et al., "Base Sequence Discrimination by Zinc–Finger DNA–Binding Domians," *Nature* 349:175–178 (1991).

Nekludova et al., "Distinctive DNA Conformation With Enlarged Major Groove is Found in Zn–Finger–DNA and Other Protein–DNA Complexes," *PNAS* 91:6948–6952 (1994).

Orkin et al., "Report and Recommendations of the Panel to Assess the NIH Investment in Research on Gene Therapy," (Dec. 7, 1995).

Pabo et al., "Systematic Analysis of Possible Hydrogen Bonds between Amino Acid Side Chains and B–form DNA," *J. Biomolecular Struct. Dynamic* 1:1039–1049 (1983).

Pabo et al., "Protein–DNA Recognition," *Ann. Rev. Biochem.* 53:293–321 (1984).

Pabo, C. O., "Transcription Factors: Structural Families and Principals of DNA Recognition," *Ann. Rev. Biochem.* 61:1053–1095 (1992).

Pavletich et al., "Crystal Structure of a Five–Finger GLI–DNA Complex: New Perspectives on Zinc Fingers," *Science,* 261:1701–1707 (1993).

Pavletich et al., "Zinc Finger–DNA Recognition: Crystal Structure of a Zif268–DNA Complex at 2.1 A," *Science* 252:809–817 (1991).

Pengue et al., "Repression of Transcriptional Activity at a Distance by the Evolutionarily Conserved KRAB Domain Present in a Subfamily of Zinc Finger Proteins," *Nuc. Acids Res.* 22(15):2908–2914 (1994).

Pengue et al., "Transcriptional Silencing of Human Immunodeficiency Virus Type I Long Terminal Repeat–Driven Gene Expression by the Kruppel–Associated Box Repressor Domain Targeted to the Transactivating Response Element," *J. Virology* 69(10):6577–6580 (1995).

Pengue et al., "Kruppel–Associated Box–Mediated Repression of RNA Polymerase 11 Promoters is Influenced by the Arrangement of Basal Promoter Elements," *PNAS* 93:1015–1020 (1996).

Pomerantz et al., "Analysis of Homeodomain Function by Structure–Based Design of a Transciption Factor," *PNAS* 92:9752–9756 (1995).

Pomerantz et al., "Structure–Based Design of a Dimeric Zinc Finger Protein," *Biochemistry* 37(4):965–970 (1998).

Pomerantz et al., "Structure–Based Design of Transcription Factors," *Science* 267:93–96 (1995).

Qian et al., "Two–Dimensional NMR Studies of the Zinc Finger Mofit:. Solution Structures and Dynamics of Mutant ZFY Domains Containing Aromatic Substitutions in the Hydrophobic Core," *Biochemistry* 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," *Molecular Endocrinology* 6(7):1103–1112 (1992).

Rauscher et al., "Binding of the Wilms' Tumor Locus Zinc Finger Protein to the EGR–1 Consensus Sequence," *Science* 250:1259–1262 (1990).

Ray et al., "Repressor to Activator Switch by Mutations in the First Zn Finger of the Glucocorticoid Receptor: Is Direct DNA Binding Necessary?," *PNAS* 88:7086–7090 (1991).

Rebar et al., "Phage Display Methods for Selecting Zinc Finger Proteins with Novel DNA–Binding Specificities," *Methods in Enzymology* 267:129–149 (1996).

Rebar et al., "Zinc Finger Phage: Affinity Selection of Fingers With New DNA–Binding Specifities," *Science* 263:671–673 (1994).

Reith et al., "Cloning of the Major Histocompatibility Complex Class II Promoter Binding Protein Affected in a Hereditary Defect in Class II Gene Regulation," *PNAS* 86:4200–4204 (1989).

Rhodes et al., "Zinc Fingers: They Play a Key Part in Regulating the Activity of Genes in Many Species, From Yeast to Humans. Fewer Than 10 Years Ago No One Knew They Existed." *Scientific American* 268:56–65 (1993).

Rice et al., "Inhibitors of HIV Nucleocapsid Protein Zinc Fingers as Candidates for the Treatment of AIDS," *Science.* 270:1194–1197 (1995).

Rivera et al., "A Humanized System for Pharmacologic Control of Gene Expression," *Nature Medicine* 2(9):1028–1032 (1996).

Rollins et al., "Role of TFIIIA Zinc Fingers In vivo: Analysis of Single–Finger Function in Developing Xenopus Embyros," *Molecular Cellular Biology* 13(8):4776–4783 (1993).

Sadowski et al., "GAL4–VP16 is an unusually potent transcriptional activator," *Nature* 335:563–568 (1988).

Saleh et al., "A Novel Zinc Finger Gene on Human Chromosome 1 qter That is Alternatively Spliced in Human Tissues and Cell Lines," *American Journal of Human Genetics* 52:192–203 (1993).

Shi et al., "Specific DNA–RNA Hybrid Binding by Zinc Finger Proteins," *Science* 268:282–284 (1995).

Shi et al., "DNA Unwinding Induced by Zinc Finger Protein Binding," *Biochemistry* 35:3845–3848 (1996).

Shi et al., "A Direct Comparison of the Properties of Natural and Designed Finger Proteins," *Chem. & Biol.* 2(2):83–89 (1995).

Singh et al., "Molecular Cloning of an Enhancer Binding Protein: Isolation by Screening of an Expression Library with a Recognition Site DNA," *Cell* 52:415–423 (1988).

Skerka et al., "Coordinate Expression and Distinct DNA-Binding Characteristics of the Four EGR–Zinc Finger Proteins in Jurkat T Lymphocytes," *Immunobiology* 198:179–191 (1997).

South et al., "The Nucleocapsid Protein Isolated from HIV–1 Particles Binds Zinc and Forms Retroviral–Type Zinc Fingers," *Biochemistry* 29:7786–7789 (1990).

Spengler et al., "Regulation of Apoptosis and Cell Cycle Arrest by ZZC1, A Novel Zinc finger Protein Expressed in the Pituitary Gland and the Brain," *EMBO J* 16(10):2814–2825 (1997).

Suzuki et al., "Stereochemical Basis of DNA Recognition by Zn Fingers," *Nuc. Acids Res.* 22(16):3397–3405 (1994).

Suzuki et al. "DNA Recognition Code of Transcription Factors in the Helix–turn–Helic, Probe Helic, Hormone Receptor, and Zinc Finger Families," *PNAS* 91:12357–12361 (1994).

Swirnoff et al., "DNA–Binding Specificity of NGFI–A and Related Zinc Finger Transcription Factors," *Mol. Cell. Biol.* 15(4):2275–2287 (1995).

Taylor et al., "Designing Zinc–Finger ADRI Mutants with Altered Specificity of DNA Binding to T in UASI Sequences," *Biochemistry* 34:3222–3230 (1995).

Thiesen et al., "Determination of DNA Binding Specificities of Mutated Zinc Finger Domains," *FEBS Letters* 283(1):23–26 (1991).

Thiesen et al., "Amino Acid Substitutions in the SP1 Zinc Finger Domain Alter the DNA Binding Affinity to Cognate SP1 Target Site," *Biochem. Biophys. Res. Communications* 175(1):333–338 (1991).

Thiesen, H.J., "From Repression Domains to Designer Zinc Finger Proteins: A Novel Strategy for Intracellular Immunization Against HIV," *Gene Expression* 5:229–243 (1996).

Thukral et al., "Localization of a Minimal Binding Domain and Activation Regions in Yeast Regulaory Protein ADRI1," *Molecular Cellular Biology* 9(6):2360–2369 (1989).

Thukral et al., "Two Monomers of Yeast Transcription Factor ADR1 Bind a Paldromic Sequence Symmetrically to Activate ADH2 Expression," *Molecular Cellular Biol.* 11(3):1566–1577 (1991).

Thukral et al., "Alanine Scanning Site–Directed Mutagenesis of the Zinc Fingers of Transcription Factor ADR1: Residues that Contact DNA and that Transactivate," *PNAS* 88:9188–9192 (1991), + correction page.

Thukral et al., "Mutations in the Zinc Fingers of ADR1 That Change the Specificity of DNA Binding and Transactivation," *Mol. Cell Biol.* 12(6):2784–2792 (1992).

Vortkamp et al., "Identification of Optimized Target Sequences for the GL13 Zinc Finger Protein," *DNA Cell Biol.* 14(7):629–634 (1995).

Wang et al., "Dimerization of Zinc Fingers Mediated by Peptides Evolved In Vitro From Random Sequences," *Proc. Natl. Acad. Sci. U.S.A.* 96:9568–9573 (1999).

Webster et al., "Conversion of the E1A Cys4 Zinc Finger to a Nonfunctional His2, Cys2 Zinc Finger by a Single Point Mutation," *PNAS* 88:9989–9993 (1991).

Whyatt et al., "The Two Zinc Finger–Like Domains of GATA–1 Have Different DNA Binding Specificities," *EMBO J.* 12(13):4993–5005 (1993).

Wilson et al., "In Vivo Mutational Analysis of the NGFI–A Zinc Fingers," *J. Biol. Chem.* 267(6):3718–3724 (1992).

Witzgall et al., "The Kruppel–Associated Box–A (KRAB–A) Domain of Zinc Finger Proteins Mediates Transcriptional Repression," *PNAS* 91:4514–4518 (1994).

Wolfe et al., "Analysis of Zinc Fingers Optimized Via Phage Display: Evaluating the Utility of a Recognition Code," *J. Mol. Biol.* 285:1917–1934 (1999).

Wright et al., "Expression of a Zinc Finger Gene in HTLV–1 and HTLV–II Transformed Cells," *Science* 248:588–591 (1990).

Wu et al., "Building Zinc Fingers by Selection: Toward a Therapeutic Application," *PNAS* 92:344–348 (1995).

Wu et al., "Human Immunodeficiency Virus Type 1 Nucleocapsid Protein Reduces Reverse Transcriptase Pausing at a Secondary Structure near the Murine Leukemia Virus Polypurine Tract" *J. Virol.* 70(10):7132–7142 (1996).

Yang et al., "Surface Plasmon Resonance Based Kinetic Studies of Zinc Finger–DNA Inteaction," *J. Immunol. Methods* 183:175–182 (1995).

Yu et al., "A Hairpin Ribozyme Inhibits Expression of Diverse Strains of Human Immunodeficiency Virus Type 1," *PNAS* 90:6340–6344 (1993).

Zhang et al., "Synthetic Zinc Finger Transcription Factor Action at an Endogenous Chromosomal Site. Activaton of the Human Erythropoietin Gene," *Journal of Biological Chemistry* 275(43):33850–33860 (2000).

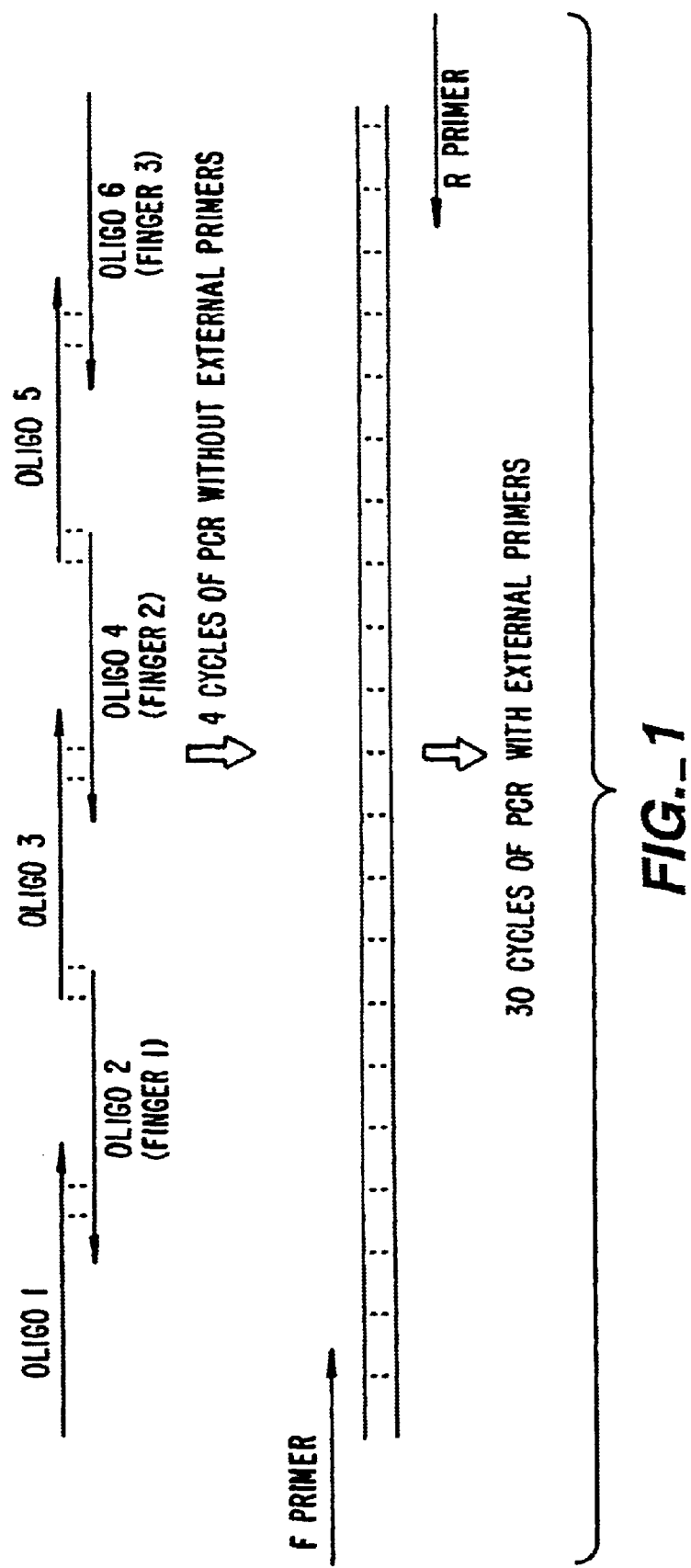
FIG._1

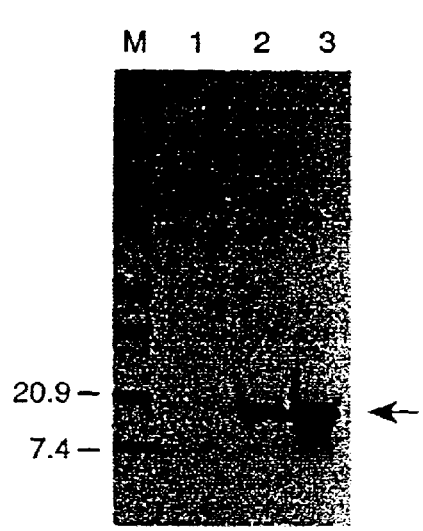
*FIG._2A*
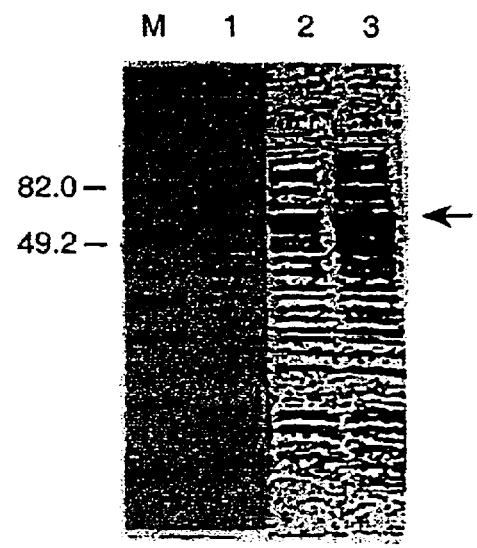
*FIG._2B*
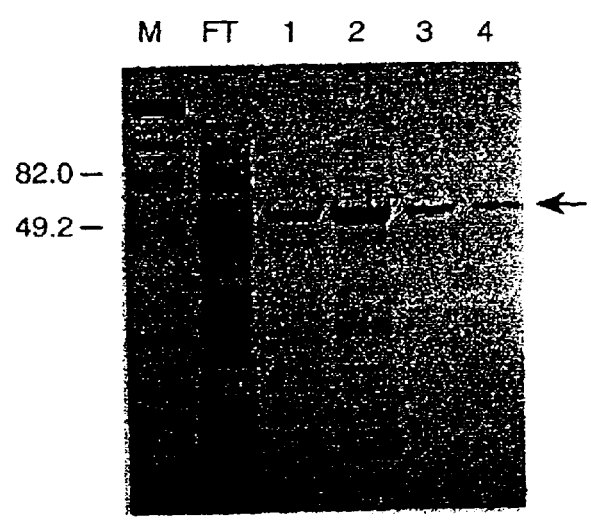
*FIG._2C*
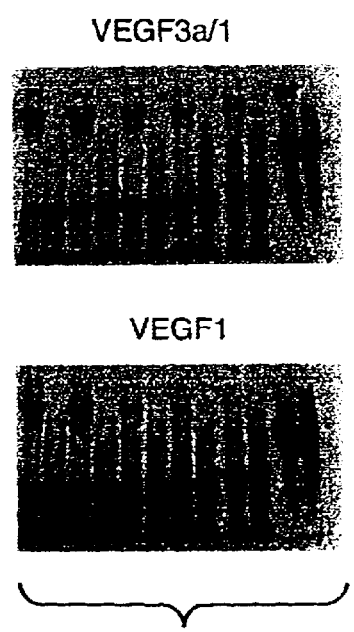
*FIG._4A*

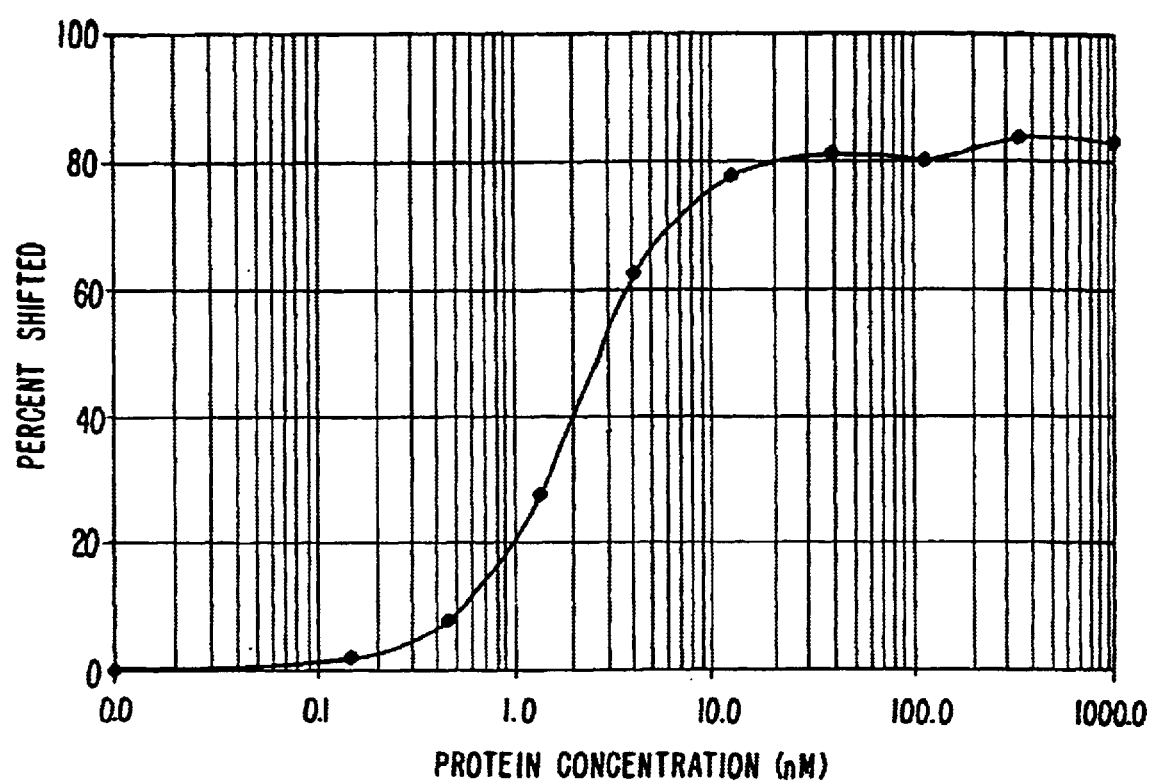
FIG._3

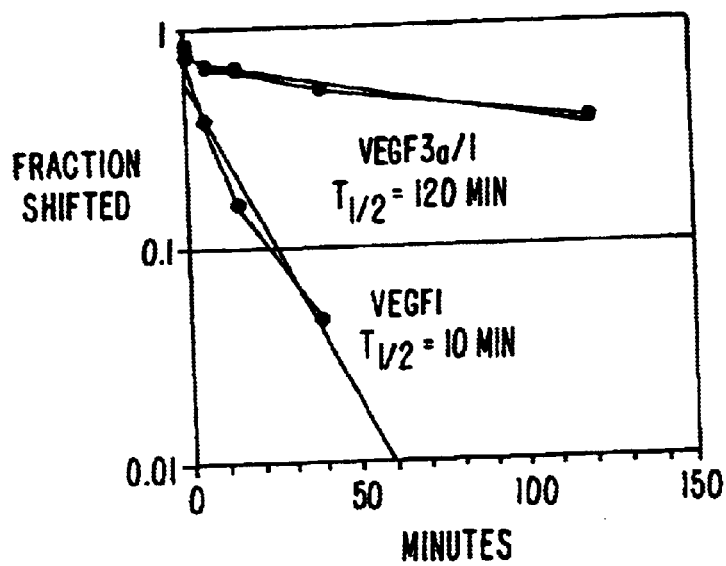
FIG._4B
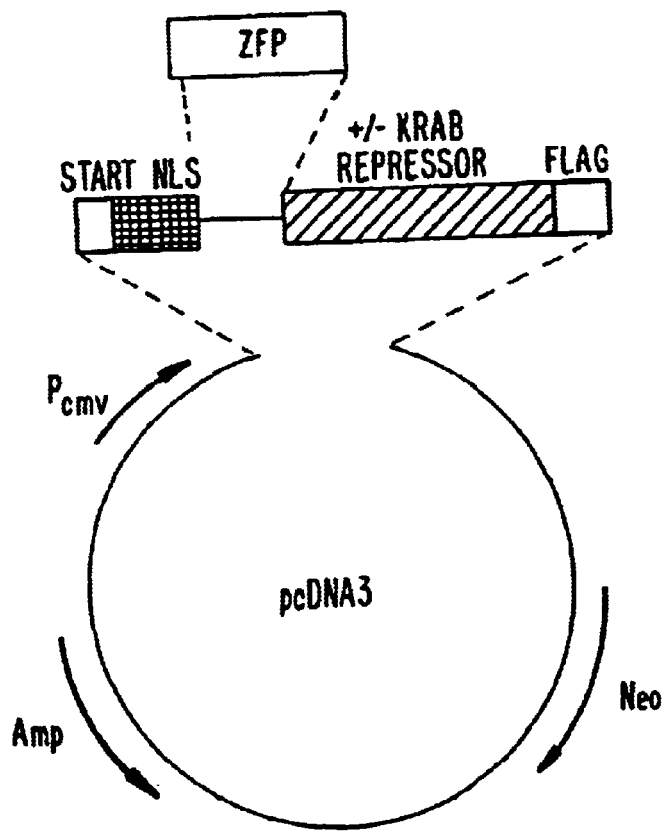
FIG._5

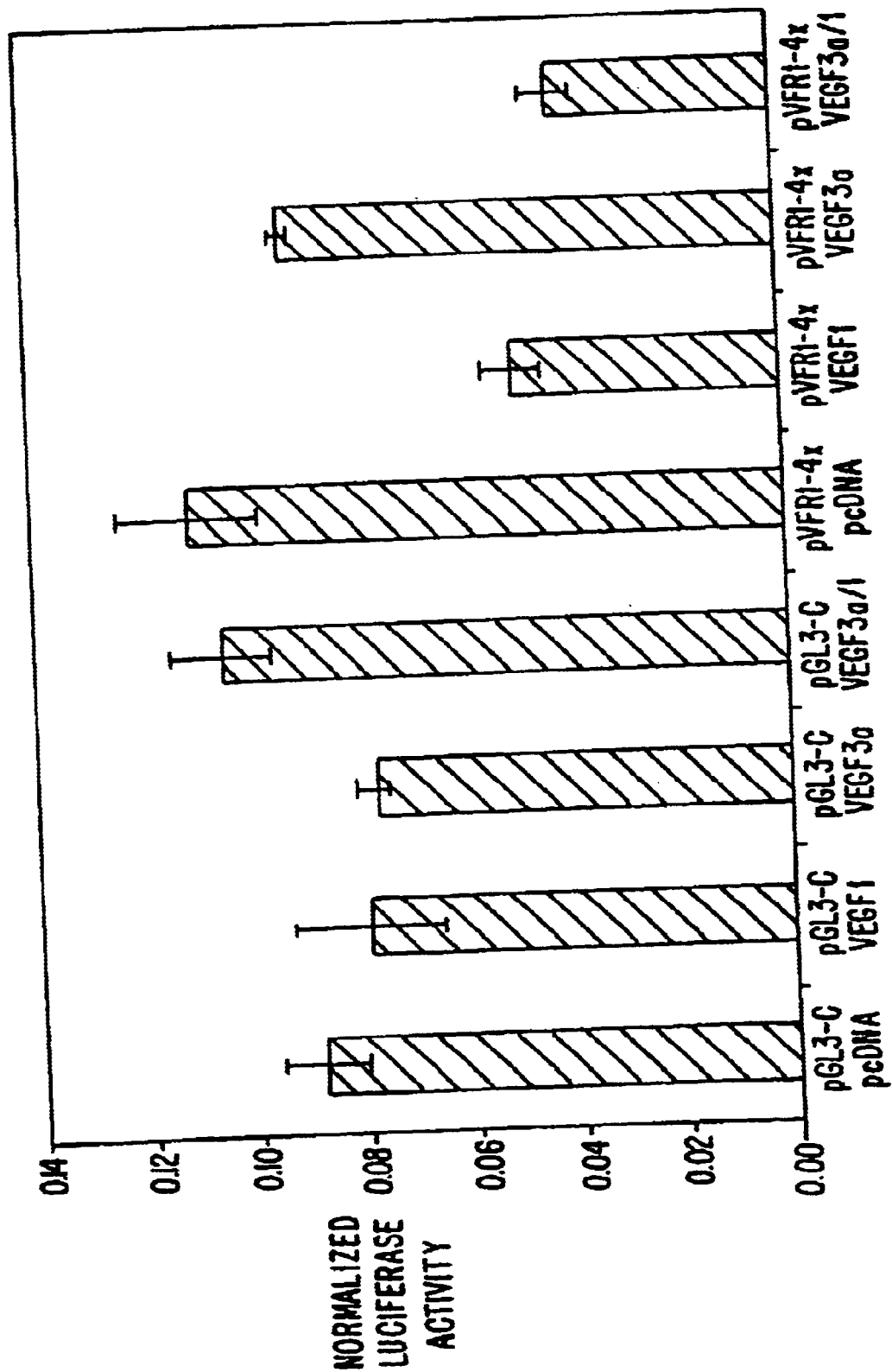
FIG._6

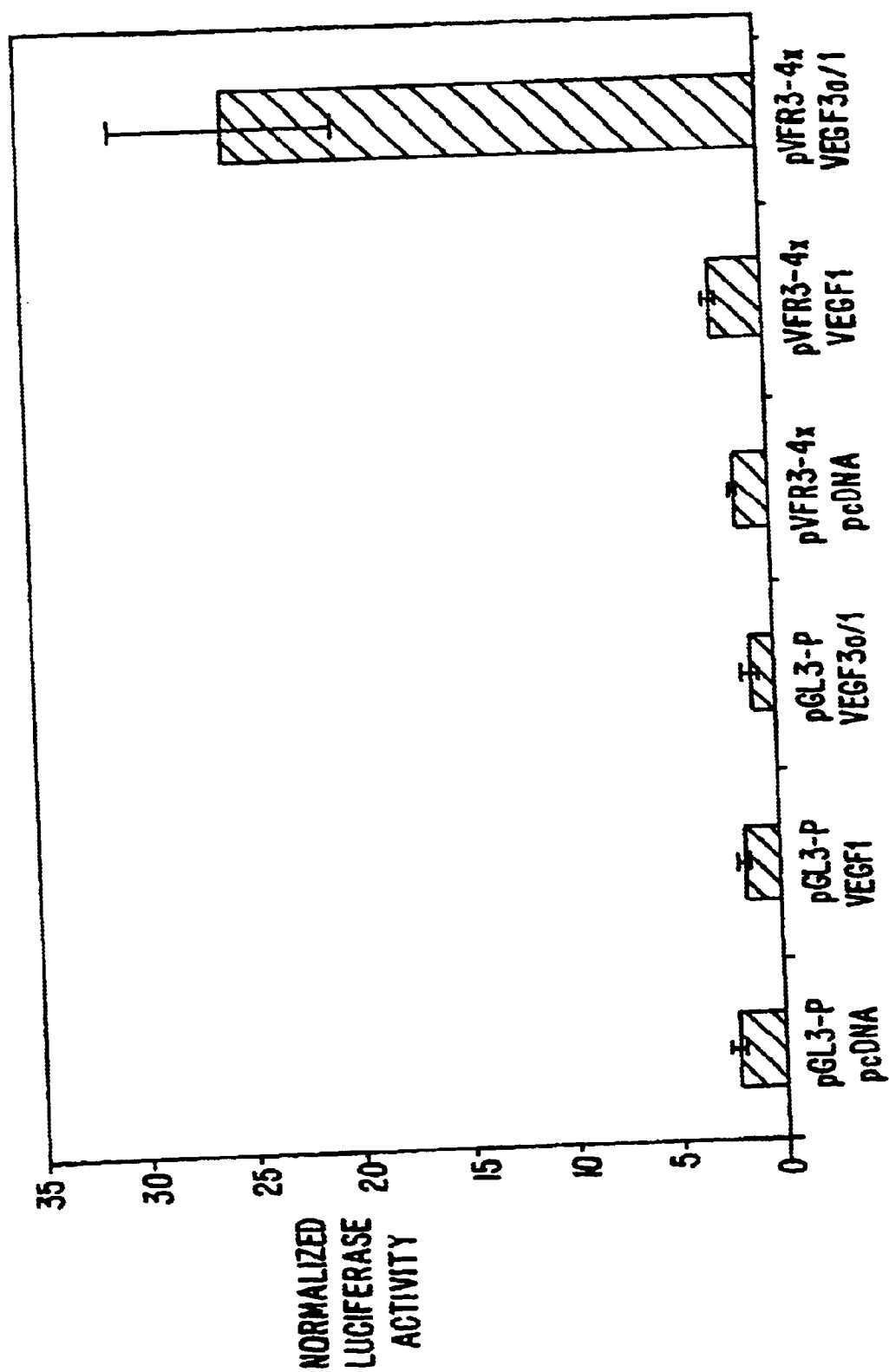
FIG._7

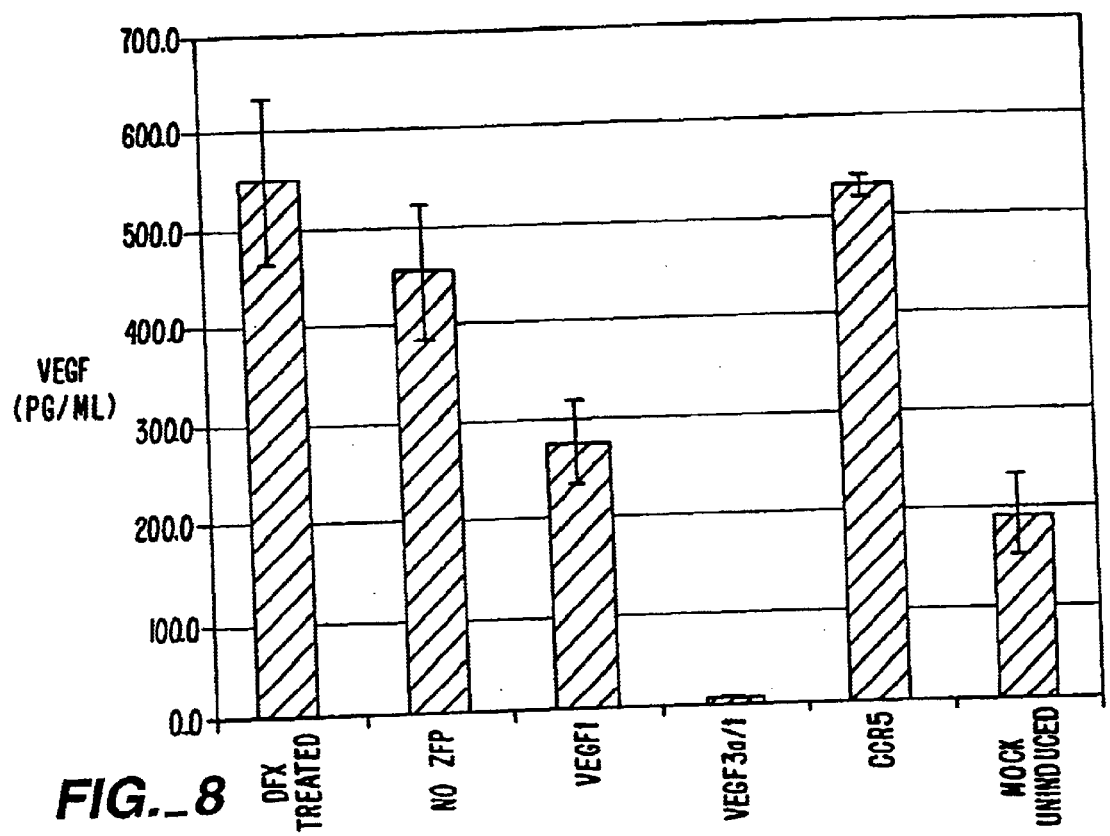
FIG._8
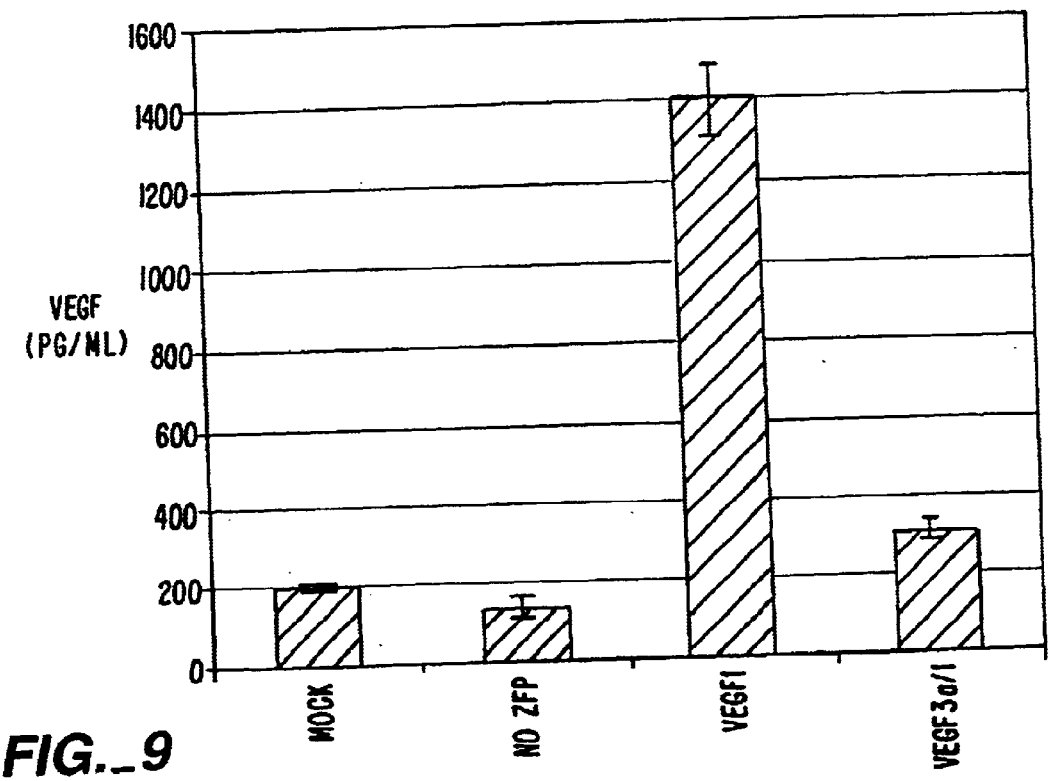
FIG._9

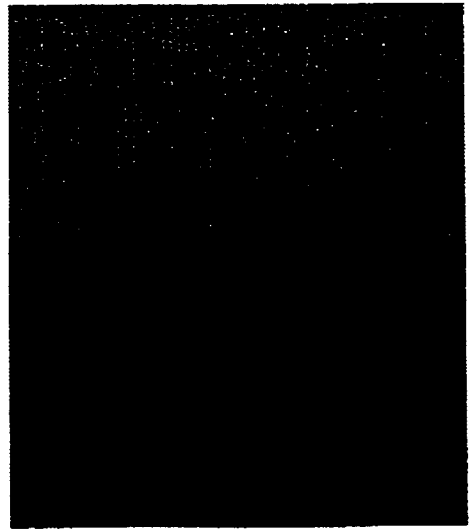
FIG._10A
FIG._10B

MODULATION OF ENDOGENOUS GENE EXPRESSION IN CELLS

CROSS-REFERENCE TO RELATED APPLICATIONS

This application is a continuation-in-part of U.S. patent application Ser. No. 09/229,037, filed Jan. 12, 1999 now U.S. Pat. No. 6,534,261, the disclosure of which is hereby incorporated by reference in its entirety.

TECHNICAL FIELD

The present disclosure provides methods and compositions for regulating expression of endogenous genes using exogenous molecules comprising, for example, recombinant zinc finger proteins.

BACKGROUND

Many, perhaps most physiological and pathophysiological processes can be controlled by the selective up or down regulation of gene expression. If methods existed for gene expression control, pathologies could be treated. Examples include the inappropriate expression of proinflamatory cytokines in rheumatoid arthritis, under expression of the hepatic LDL receptor in hypercholesteremia, over expression of proangiogenic factors and under expression of anti-angiogenic factors in solid tumor growth, to name just a few. In addition, pathogenic organisms such as viruses, bacteria, fungi, and protozoa could be controlled by altering gene expression. There is a clear unmet need for therapeutic approaches that are simply able to up-regulate beneficial genes and down-regulate disease causing genes.

In addition to the direct therapeutic utility provided by the ability to manipulate gene expression, this ability can be used experimentally to determine the function of a gene of interest. One common existing method for experimentally determining the function of a newly discovered gene is to clone its cDNA into an expression vector driven by a strong promoter and measure the physiological consequence of its over-expression in a transfected cell. This method is labor intensive and does not address the physiological consequences of down-regulation of a target gene. Simple methods allowing the selective over and under-expression of uncharacterized genes would be of great utility to the scientific community. Methods that permit the regulation of genes in cell model systems, transgenic animals and transgenic plants would find widespread use in academic laboratories, pharmaceutical companies, genomics companies and in the biotechnology industry.

An additional use of tools permitting the manipulation of gene expression is in the production of commercially useful biological products. Cell lines, transgenic animals and transgenic plants could be engineered to over-express a useful protein product. The production of erythropoietin by such an engineered cell line serves as an example. Likewise, production from metabolic pathways might be altered or improved by the selective up or down-regulation of a gene encoding a crucial enzyme. An example of this is the production of plants with altered levels of fatty acid saturation.

Methods currently exist in the art, which allow one to alter the expression of a given gene, e.g., using ribozymes, antisense technology, small molecule regulators, over-expression of cDNA clones, and gene-knockouts. These methods have to date proven to be generally insufficient for many applications and typically have not demonstrated either high target efficacy or high specificity in vivo. For useful experimental results and therapeutic treatments, these characteristics are desired.

Gene expression is normally controlled through alterations in the function of sequence specific DNA binding proteins called transcription factors. These bind in the general proximity (although occasionally at great distances) of the point of transcription initiation of a gene. They act to influence the efficiency of formation or function of a transcription initiation complex at the promoter. Transcription factors can act in a positive fashion (transactivation) or in a negative fashion (transrepression).

Transcription factor function can be constitutive (always "on") or conditional. Conditional function can be imparted on a transcription factor by a variety of means, but the majority of these regulatory mechanisms depend of the sequestering of the factor in the cytoplasm and the inducible release and subsequent nuclear translocation, DNA binding and transactivation (or repression). Examples of transcription factors that function this way include progesterone receptors, sterol response element binding proteins (SREBPs) and NF-kappa B. There are examples of transcription factors that respond to phosphorylation or small molecule ligands by altering their ability to bind their cognate DNA recognition sequence (Hou et al., *Science* 256:1701 (1994); Gossen & Bujard, *PNAS* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). This mechanism is common in prokaryotes but somewhat less common in eukaryotes.

Zinc finger proteins ("ZFPs") are proteins that bind to DNA, RNA and/or protein in a sequence-specific manner. Zinc fingers were first identified in the transcription factor TFIIIA from the oocytes of the African clawed toad, *Xenopus laevis*. ZFPs are widespread in eukaryotic cells. An exemplary motif characterizing one class of these proteins ($C_2H_2$ class) is -Cys-$(X)_{2-4}$-Cys-$(X)_{12}$-His-$(X)_{3-5}$His (SEQ ID NO:1) (where X is any amino acid). A single finger domain is about 30 amino acids in length and several structural studies have demonstrated that it contains an alpha helix containing the two invariant histidine residues co-ordinated through zinc with the two cysteines of a single beta turn. To date, over 10,000 zinc finger sequences have been identified in several thousand known or putative transcription factors. ZFPs are involved not only in DNA-recognition, but also in RNA binding and protein-protein binding. Current estimates are that this class of molecules will constitute about 2% of all human genes.

The X-ray crystal structure of Zif268, a three-finger domain from a murine transcription factor, has been solved in complex with its cognate DNA-sequence and shows that each finger can be superimposed on the next by a periodic rotation and translation of the finger along the main DNA axis. The structure suggests that each finger interacts independently with DNA over 3 base-pair intervals, with side-chains at positions –1, 2, 3 and 6 on each recognition helix making contacts with respective DNA triplet subsite. The amino terminus of Zif268 is situated at the 3' end of its DNA recognition subsite. Recent results have indicated that some zinc fingers can bind to a fourth base in a target segment (Isalan et al., *PNAS* 94:5617–5621 (1997). The fourth base is on the opposite strand from the other three bases recognized by zinc finger and complementary to the base immediately 3' of the three base subsite.

The structure of the Zif268-DNA complex also suggested that the DNA sequence specificity of a ZFP might be altered by making amino acid substitutions at the four helix positions (−1, 2, 3 and 6) on a zinc finger recognition helix. Phage display experiments using zinc finger combinatorial libraries to test this observation were published in a series of papers in 1994 (Rebar et al., *Science* 263:671–673 (1994); Jamieson et al., *Biochemistry* 33:5689–5695 (1994); Choo et al., *PNAS* 91:11163–11167 (1994)). Combinatorial libraries were constructed with randomized side-chains in either the first or middle finger of Zif268 and then isolated with an altered Zif268 binding site in which the appropriate DNA sub-site was replaced by an altered DNA triplet. Correlation between the nature of introduced mutations and the resulting alteration in binding specificity gave rise to a partial set of substitution rules for rational design of ZFPs with altered binding specificity.

Greisman & Pabo, *Science* 275:657–661 (1997) discuss an elaboration of a phage display method in which each finger of a zinc finger protein is successively subjected to randomization and selection. This paper reported selection of ZFPs for a nuclear hormone response element, a p53 target site and a TATA box sequence.

Recombinant ZFPs have been reported to have the ability to regulate gene expression of transiently expressed reporter genes in cultured cells (see, e.g., Pomerantz et al., *Science* 267:93–96 (1995); Liu et al., *PNAS* 94:5525–5530 1997); and Beerli et al., *PNAS* 95:14628–14633 (1998)).

For example, Pomerantz et al., *Science* 267:93–96 (1995) report an attempt to design a novel DNA binding protein by fusing two fingers from Zif268 with a homeodomain from Oct-1. The hybrid protein was then fused with either a transcriptional activator or repressor domain for expression as a chimeric protein. The chimeric protein was reported to bind a target site representing a hybrid of the subsites of its two components. The authors then constructed a reporter vector containing a luciferase gene operably linked to a promoter and a hybrid site for the chimeric DNA binding protein in proximity to the promoter. The authors reported that their chimeric DNA binding protein could activate or repress expression of the luciferase gene.

Liu et al., *PNAS* 94:5525–5530 (1997) report forming a composite ZFP by using a peptide spacer to link two component ZFPs, each having three fingers. The composite protein was then further linked to transcriptional activation or repression domains. It was reported that the resulting chimeric protein bound to a target site formed from the target segments bound by the two component ZFPs. It was further reported that the chimeric ZFP could activate or repress transcription of a reporter gene when its target site was inserted into a reporter plasmid in proximity to a promoter operably linked to the reporter.

Beerli et al., *PNAS* 95:14628–14633 (1998) report construction of a chimeric six finger ZFP fused to either a KRAB, ERD, or SID transcriptional repressor domain, or the VP16 or VP64 transcriptional activation domain. This chimeric ZFP was designed to recognize an 18 bp target site in the 5' untranslated region of the human erbB-2 gene. Using this construct, the authors of this study report both activation and repression of a transiently expressed reporter luciferase construct linked to the erbB-2 promoter.

In addition, a recombinant ZFP was reported to repress expression of an integrated plasmid construct encoding a bcr-abl oncogene (Choo et al., *Nature* 372:642–645 (1994)). The target segment to which the ZFPs bound was a nine base sequence GCA GAA GCC chosen to overlap the junction created by a specific oncogenic translocation fusing the genes encoding bcr and abl. The intention was that a ZFP specific to this target site would bind to the oncogene without binding to abl or bcr component genes. The authors used phage display to select a variant ZFP that bound to this target segment. the variant ZFP thus isolated was then reported to repress expression of a stably transfected bcr-abl construct in a cell line.

To date, these methods have focused on regulation of either transiently expressed genes, or on regulation of exogenous genes that have been integrated into the genome. The transiently expressed genes described by Pomerantz et al., Liu et al., and Beerli et al. are episomal and are not packaged into chromatin in the same manner as chromosomal genes. Moreover, even the stably expressed gene described by Choo et al. is randomly integrated into the genome and is not found in a native chromatin environment as compared to an endogenous gene. In contrast, specific regulation of an endogenous cellular gene in its native chromatin environment using a ZFP has not yet been demonstrated in the art.

SUMMARY

In one aspect, a method of modulating expression of an endogenous cellular gene in a cell is provided. In certain embodiments, the method comprises the step of contacting a first target site in the endogenous cellular gene with a designed or selected zinc finger protein, wherein the protein comprises a functional domain; and wherein said the contacting results in modulating expression of the endogenous cellular gene. The modulation of expression can be, for example, repression or activation.

Any of the methods described herein can further comprise the step of contacting a second target site in the endogenous cellular gene with a second zinc finger protein. The first and second target sites can be adjacent or non-adjacent. Additionally, the first and second zinc finger proteins can be covalently linked. In certain embodiments, the first and/or second target sites are upstream of a transcription initiation site of the endogenous cellular gene. In other embodiments, the first and/or second target sites are adjacent to a transcription initiation site of the endogenous cellular gene. In yet other embodiments, the first and/or second target sites are downstream of a transcription initiation site of the endogenous cellular gene.

In any of the methods described herein, the first and/or second zinc finger protein can be a fusion protein comprising at least two regulatory domains. Similarly, in any of the methods described herein, the first and/or second zinc finger protein can be a fusion protein comprising a functional domain, for example, bifunctional domains (e.g, thyroid hormone receptor, retinoic acid receptor, estrogen receptor and glucocorticoid receptor); functional domains that act to repress expression (e.g., unliganded thyroid hormone receptors (TR) for repression), v-erbA, Dax, RBP, MeCP2, MBD2B, a DNMT or any combination thereof); and functional domains that act to activate expression (e.g. ligand-bound thyroid hormone receptor, such as TR bound by the ligand is 3,5,3'-triiodo-L-thyronine (T3)). In certain embodiments, both the first and second zinc finger proteins are fusion proteins, each comprising a functional domain or at least two functional domains. In embodiments in which two or more functional domains are employed, these domains can be the same or can include any number of different functional domains. Furthermore, in embodiments where one or more of the functional domains are bifunctional domains (BFDs) whose the modulating activity is dependent upon interaction of the BFD with a second molecule, the second molecule can be, for example, a protein and/or a small molecule (e.g., thyroid hormone (T3), all-trans-retinoic acid, estradiol, tamoxifen, 4-hydroxytamoxifen, RU-486 and dexamethasone).

In any of the methods described herein, the cell can be, for example, an animal cell (e.g., a mammalian cell such as a human cell), a plant cell, a bacterial cell, a protozoal cell, or a fungal cell.

In certain embodiments, the methods described herein further comprise the step of first administering to the cell a delivery vehicle comprising the zinc finger protein, wherein the delivery vehicle comprises a liposome or a membrane translocation polypeptide.

In still further embodiments, the zinc finger proteins are delivered to the cell as nucleic acid molecules encoding the designed or selected zinc finger protein. Thus, in certain embodiments, the first and/or zinc finger proteins are encoded by a zinc finger protein nucleic acid operably linked to a promoter, and the method further comprises the step of first administering the nucleic acid to the cell in a lipid-:nucleic acid complex or as naked nucleic acid. In other embodiments, wherein the zinc finger protein(s) is(are) encoded by an expression vector (e.g., a viral expression vector, a retroviral expression vector, an adenoviral expression vector, or an AAV expression vector) comprising a zinc finger protein nucleic acid operably linked to a promoter, and the method further comprises the step of first administering the expression vector to the cell. In any of the methods described herein, the promoter operably linked to the zinc finger protein-encoding nucleic acid can be inducible.

In a still further aspect, the zinc finger protein(s) comprise(s) an SP-1 backbone.

These and other embodiments will be readily apparent to one of skill in the art upon reading the present disclosure.

BRIEF DESCRIPTION OF THE DRAWINGS

FIG. 1: PCR amplification scheme for production of ZFP-encoding synthetic genes.

FIG. 2. Expression and purification of typical ZFPs.

FIG. 2A: Unfused ZFP before induction (lane 1), after induction (lane 2), and after purification (lane 3).

FIG. 2B: MBP-VEGF expression before induction (lane 1), after induction (lane 2), and after French Press lysis (lane 3).

FIG. 2C: Purification of MBP-VEGF by amylose affinity column showing flow-through (FT), and initial fractions (1–4). Fraction 2 was used for electrophoretic mobility shift assays ("EMSA"). M, molecular weight markers.

FIG. 3. Typical EMSA experiment with MBP fused ZFP. MBP-VEGF1 protein was bound to labeled duplex DNA as described in the text. A three-fold protein dilution series was carried out; each point represents the percent shifted at that particular protein concentration plotted on a semi-log graph. Quantitation was by phosphorimager. In this case, the protein concentration yielding 50% of maximum shift (the apparent $K_d$) was 2 nM.

FIG. 4. Off-rate experiment comparing VEGF1 to VEGF3a/1. Protein-DNA complexes were pre-formed and incubated with a 1000-fold excess of unlabeled oligonucleotide. Samples were electrophoresed at various times and the amount of shifted product was measured by phosphorimager. Curve fitting was used to calculate the indicated complex half-lives.

FIG. 5. Typical expression vector used for transient ZFP expression in mammalian cells.

FIG. 6. Co-transfection data showing repression of luciferase reporter activity via VEGF-KRAB protein expression. Error bars show the standard deviation of triplicate transfections. pGL3-C (reporter vector control); pVFR1-4x (VEGF reporter plasmid); VEGF1 (VEGF1-KRAB); VEGF3a (VEGF3a-KRAB); VEGF3a/1 (VEGF3a/1-KRAB).

FIG. 7. Co-transfection data showing activation of luciferase reporter activity via VEGF-VP16 protein expression. Error bars show the standard deviation of triplicate transfections. pGL3-P (reporter with no VEGF target); pcDNA (empty effector vector control); pVFR3-4x (VEGF reporter plasmid); VEGF1 (VEGF1-VP16); VEGF3a (VEGF3a-VP16); VEGF3a/1 (VEGF3a/1-VP16).

FIG. 8. VEGF ELISA data showing repression of endogenous VEGF gene expression due to transfection of a VEGF ZFP-KRAB effector plasmid. DFX treated (control nontransfected Dfx treated cells; No ZFP (pcDNA-control), VEGF1 (VEGF1-KRAB), VEGF3a/1 (VEGF3a/1-KRAB), CCR5 (CCR5-KRAB); Mock uninduced (mock transfected cells untreated with DFX). Error bars show the standard deviation of duplicate transfections.

FIG. 9. VEGF ELISA data showing activation of endogenous VEGF gene expression due to transfection of a VEGF ZFP-VP16 effector plasmid. Mock (mock transfected cells); No ZFP (NVF-control), VEGF1 (VEGF1-VP16), VEGF3a/1 (VEGF3a/1-VP16). Error bars show the standard deviation of duplicate transfections.

FIG. 10. RNase protection assay showing changes in VEGF specific mRNA by VEGF-specific ZFPs. Panel A: Activation of VEGF mRNA, NVF-Control (no ZFP), VEGF1-NVF (VEGF1-VP16), CCR5-5-NVF (CCR5-VP16), CCR5-3-NVF (CCR5-VP16). Panel B: Repression of VEGF mRNA. NKF-Control (no ZFP), VEGF1-NKF (VEGF1-KRAB), VEGF3a/1-NKF (VEGF3a/1-KRAB), CCR5-3-NKF (CCR5-KRAB). The size of the 148 nucleotide VEGF specific band is indicated by an arrow. The VEGF specific probe was synthesized from a human angiogenesis multi-probe template set (Pharmingen). As a control, signals from the housekeeping genes L32 and GAPDH are shown (arrrows).

DETAILED DESCRIPTION

Introduction

Figure 11:
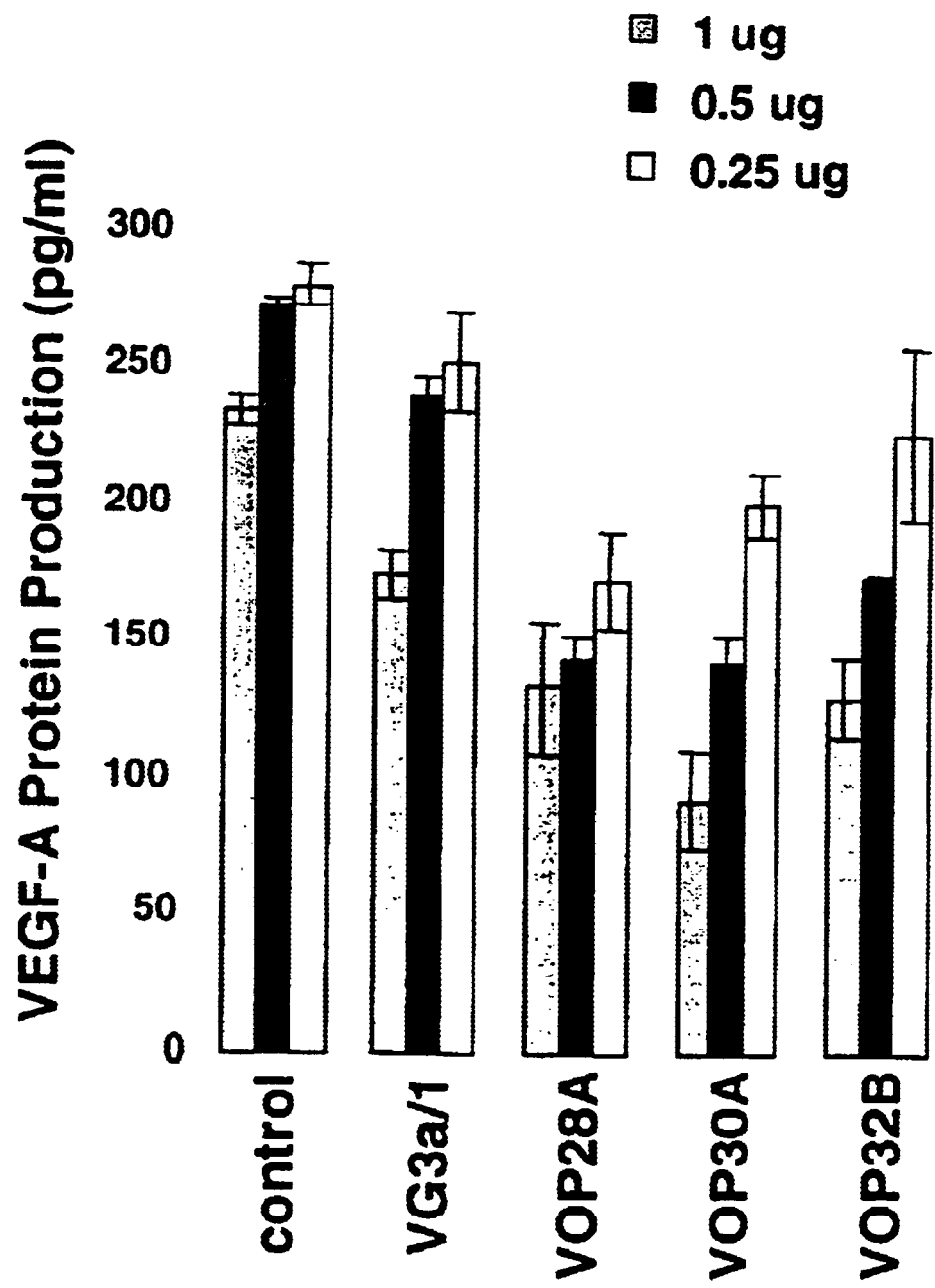
FIG. 11. Levels of VEGF-A protein in the culture medium of human 293 cells that have been transfected with plasmids encoding different v-erbA/ZFP fusions. The different ZFP binding domains are indicated along the abscissa and are described in Example 9. For each plasmid, different concentrations of DNA were used for transfection, as indicated in the Figure. Control cells were transfected with vector plasmid, which lacked sequences encoding a ZFP fusion protein.

The present application demonstrates for the first time that ZFPs can be used to regulate expression of an endogenous cellular gene that is present in its native chromatin environment. The present disclosure thus provides zinc finger DNA binding proteins that have been engineered to specifically recognize, with high efficacy, endogenous cellular genes. The experiments described herein demonstrate that a 3 finger ZFP with a target site affinity of less than about 10 nM (VEGF1) can be used to effectively activate or repress activity of an endogenous gene. Furthermore, a 6 finger ZFP (VEGF3a/1) was also shown to effectively repress activity of an endogenous gene. Preferably, ZFPs exhibit high affinity for their target sites, with $K_d$s of less than about 100 nM, preferably less than about 50 nM, most preferably less than about 25 nM or lower.

As a result, exogenous molecules such as, for example, ZFPs can be used to regulate endogenous gene expression, both through activation and repression of endogenous gene transcription. The ZFPs can also be linked to regulatory domains, creating chimeric transcription factors to activate or repress transcription. In one preferred embodiment, the methods of regulation use ZFPs with a $K_d$ of less than about 25 nM to activate or repress gene transcription. ZFPs therefore can be used to repress transcription of an endogenous cellular gene by 20% or more, and can be used to activate transcription of an endogenous cellular gene by about 1.5 fold or more.

Such methods of regulating gene expression allow for novel human and mammalian therapeutic applications, e.g., treatment of genetic diseases, cancer, fungal, protozoal, bacterial, and viral infection, ischemia, vascular disease, arthritis, immunological disorders, etc., as well as providing means for functional genomics assays, and means for developing plants with altered phenotypes, including disease resistance, fruit ripening, sugar and oil composition, yield, and color.

As described herein, ZFPs can be designed to recognize any suitable target site, for regulation of expression of any endogenous gene of choice. Examples of endogenous genes suitable for regulation include VEGF, CCR5, ERα, Her2/ Neu, Tat, Rev, HBV C, S, X, and P, LDL-R, PEPCK, CYP7, Fibrinogen, ApoB, Apo E, Apo(a), renin, NF-κB, I-κB, TNF-α, FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bc1–2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, and other disease-related genes.

A general theme in transcription factor function is that simple binding and sufficient proximity to the promoter are all that is generally needed. Exact positioning relative to the promoter, orientation, and within limits, distance do not matter greatly. This feature allows considerable flexibility in choosing sites for constructing artificial transcription factors. The target site recognized by the ZFP therefore can be any suitable site in the target gene that will allow activation or repression of gene expression by a ZFP, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region. As described below, typically each finger recognizes 2–4 base pairs, with a two finger ZFP binding to a 4 to 7 bp target site, a three finger ZFP binding to a 6 to 10 base pair site, and a six finger ZFP binding to two adjacent target sites, each target site having from 6–10 base pairs.

As described herein, two ZFPs can be administered to a cell, recognizing either the same target endogenous cellular gene, or different target endogenous cellular gene. The first ZFP optionally is associated with the second ZFP, either covalently or non-covalently. Recognition of adjacent target sites by either associated or individual ZFPs can be used to produce cooperative binding of the ZFPs, resulting in an affinity that is greater than the affinity of the ZFPs when individually bound to their target site.

In one embodiment, two ZFPs are produced as a fusion protein linked by an amino acid linker, and the resulting six finger ZFP recognizes an approximately 18 base pair target site (see, e.g., Liu et al., PNAS 94:5525–5530 (1997)). An 18 base pair target site is expected to provide specificity in the human genome, as a target site of that size should occur only once in every $3 \times 10^{10}$ base pairs, and the size of the human genome is $3.5 \times 10^9$ base pairs (see, e.g., Liu et al., PNAS 94:5525–5530 (1997)). In another embodiment, the ZFPs are non-covalently associated, through a leucine zipper, a STAT protein N-terminal domain, or the FK506 binding protein (see, e.g., O'Shea, Science 254: 539 (1991), Barahmand-Pour et al., Curr. Top. Microbiol. Immunol. 211:121–128 (1996); Klemm et al., Annu. Rev. Immunol. 16:569–592 (1998); Ho et al., Nature 382:822–826 (1996)).

In another embodiment, the ZFP is linked to at least one or more regulatory domains, described below. Preferred regulatory domains include transcription factor repressor or activator domains such as KRAB and VP16, co-repressor and co-activator domains, DNA methyl transferases, histone acetyltransferases, histone deacetylases, and endonucleases such as Fok1. For repression of gene expression, typically the expression of the gene is reduced by about 20% (i.e., 80% of non-ZFP modulated expression), more preferably by about 50% (i.e., 50% of non-ZFP modulated expression), more preferably by about 75–100% (i.e., 25% to 0% of non-ZFP modulated expression). For activation of gene expression, typically expression is activated by about 1.5 fold (i.e., 150% of non-ZFP modulated expression), preferably 2 fold (i.e., 200% of non-ZFP modulated expression), more preferably 5–10 fold (i.e., 500–1000% of non-ZFP modulated expression), up to at least 100 fold or more.

The expression of engineered ZFP activators and repressors can be also controlled by systems typified by the tet-regulated systems and the RU-486 system (see, e.g., Gossen & Bujard, *PNAS* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). These impart small molecule control on the expression of the ZFP activators and repressors and thus impart small molecule control on the target gene(s) of interest. This beneficial feature could be used in cell culture models, in gene therapy, and in transgenic animals and plants.

The practice of conventional techniques in molecular biology, biochemistry, chromatin structure and analysis, computational chemistry, cell culture, recombinant DNA, bioinformatics, genomics and related fields are well-known to those of skill in the art and are discussed, for example, in the following literature references: Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999, all of which are incorporated by reference in their entireties.

Definitions

As used herein, the following terms have the meanings ascribed to them unless specified otherwise.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. The terms also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Nucleic acids include, for example, genes, cDNAs, and mRNAs. Polynucleotide sequences are displayed herein in the conventional 5'-3' orientation.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "binding protein" "or binding domain" is a protein or polypeptide that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger binding protein" is a protein or polypeptide that binds DNA, RNA and/or protein, preferably in a sequence-specific manner, as a result of stabilization of protein structure through coordination of a zinc ion. The term zinc finger binding protein is often abbreviated as zinc finger protein or ZFP. The individual DNA binding domains are typically referred to as "fingers" A ZFP has least one finger, typically two fingers, three fingers, or six fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$-His-$(X)_{3-5}$-His (SEQ ID NO:1)(where X is any amino acid). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081–1085 (1996)).

A "designed" zinc finger protein is a protein not occurring in nature whose structure and composition result principally from rational criteria. Rational criteria for design include application of substitution rules and computerized algorithms for processing information in a database storing information of existing ZFP designs and binding data, for example as described in co-owned PCT WO 00/42219. A "selected" zinc finger protein is a protein not found in nature whose production results primarily from an empirical process such as phage display. See e.g., U.S. Pat. Nos. 5,789, 538; 6,007,988; 6,013,453; WO 95/19431; WO 96/06166 and WO 98/54311.

A "target site" or "target sequence" is a sequence that is bound by a binding protein such as, for example, a ZFP. Target sequences can be nucleotide sequences (either DNA or RNA) or amino acid sequences. A single target site typically has about four to about ten base pairs. Typically, a two-fingered ZFP recognizes a four to seven base pair target site, a three-fingered ZFP recognizes a six to ten base pair target site, and a six fingered ZFP recognizes two adjacent nine to ten base pair target sites. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

The term "adjacent target sites" refers to non-overlapping target sites that are separated by zero to about 5 base pairs.

The term "naturally-occurring" is used to describe an object that can be found in nature, as distinct from being artificially produced by a human.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the ZFP. Any assay system can be used, as long is it gives an accurate measurement of the actual $K_d$ of the ZFP. In one embodiment, the $K_d$ for a ZFP is measured using an electrophoretic mobility shift assay ("EMSA"), as described in Example 1 and elsewhere in the present specification. Unless an adjustment is made for ZFP purity or activity, the $K_d$ calculations made using the method of Example 1 may result in an underestimate of the true $K_d$ of a given ZFP. Preferably, the $K_d$ of a ZFP used to modulate transcription of an endogenous cellular gene is less than about 100 nM, more preferably less than about 75 nM, more preferably less than about 50 nM, most preferably less than about 25 nM.

"Specific binding" between, for example, a ZFP and a specific target site means a binding affinity of at least $1 \times 10^6$ $M^{-1}$.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. Thus, the term "exogenous regulatory molecule" refers to a molecule that can modulate gene expression in a target cell but which is not encoded by the cellular genome of the target cell.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and components of chromatin remodeling complexes.

Thus, an "endogenous cellular gene" refers to a gene that is native to a cell, which is in its normal genomic and chromatin context, and which is not heterologous to the cell. Such cellular genes include, e.g., animal genes, plant genes, bacterial genes, protozoal genes, fungal genes, mitrochondrial genes, and chloroplastic genes.

An "endogenous gene" refers to a microbial or viral gene that is part of a naturally occurring microbial or viral genome in a microbially or virally infected cell. The microbial or viral genome can be extrachromosomal or integrated into the host chromosome. This term also encompasses endogenous cellular genes, as described above.

A "native chromatin environment" refers to the naturally occurring, structural relationship of genomic DNA (e.g., bacterial, animal, fungal, plant, protozoal, mitochondrial, and chloroplastic) and DNA-binding proteins (e.g., histones, non-histone chromosomal proteins and bacterial DNA binding protein II), which together form chromosomes. The endogenous cellular gene can be in a transcriptionally active or inactive state in the native chromatin environment.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

The phrase "RNA polymerase pause site" is described in Uptain et al., *Annu. Rev. Biochem.* 66:117–172 (1997).

"Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321:522–525 (1986), and published UK patent application No. 8707252). Backbone sequences for the ZFPs are preferably be selected from existing human $C_2H_2$ ZFPs (e.g., SP-1). Functional domains are preferably selected from existing human genes, (e.g., the activation domain from the p65 subunit of NF-κB). Where possible, the recognition helix sequences will be selected from the thousands of existing ZFP DNA recognition domains provided by sequencing the human genome. As much as possible, domains will be combined as units from the same existing proteins. All of these steps will minimize the introduction of new junctional epitopes in the chimeric ZFPs and render the engineered ZFPs less immunogenic.

"Administering" an expression vector, nucleic acid, ZFP, or a delivery vehicle to a cell comprises transducing, transfecting, electroporating, translocating, fusing, phagocytosing, shooting or ballistic methods, etc., i.e., any means by which a protein or nucleic acid can be transported across a cell membrane and preferably into the nucleus of a cell.

The term "effective amount" includes that amount which results in the desired result, for example, deactivation of a previously activated gene, activation of a previously repressed gene, or inhibition of transcription of a structural gene or translation of RNA.

A "delivery vehicle" refers to a compound, e.g., a liposome, toxin, or a membrane translocation polypeptide, which is used to administer a ZFP. Delivery vehicles can also be used to administer nucleic acids encoding ZFPs, e.g., a lipid:nucleic acid complex, an expression vector, a virus, and the like.

A "gene," for the purposes of the present disclosure, includes a DNA region encoding a gene product (see below), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus.

For example, the long terminal repeat (LTR) of retroviruses is a promoter region which may be a target for a modified zinc finger binding polypeptide. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a modified zinc finger binding polypeptide as described herein.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2-to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2-to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the modified zinc finger-nucleotide binding polypeptides disclosed herein may modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) Nature Biotechnology 15:961–964); changes in signal transduction; changes in phosphorylation and dephosphorylation; changes in receptor-ligand interactions; changes in concentrations of second messengers such as, for example, cGMP, cAMP, $IP_3$, and $Ca^{2+}$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

Accordingly, the terms "modulating expression" "inhibiting expression" and "activating expression" of a gene can refer to the ability of a molecule to activate or inhibit transcription of a gene. Activation includes prevention of transcriptional inhibition (i.e., prevention of repression of gene expression) and inhibition includes prevention of transcriptional activation (i.e., prevention of gene activation).

To determine the level of gene expression modulation by a ZFP, cells contacted with ZFPs are compared to control cells, e.g., without the zinc finger protein or with a non-specific ZFP, to examine the extent of inhibition or activation. Control samples are assigned a relative gene expression activity value of 100%. Modulation/inhibition of gene expression is achieved when the gene expression activity value relative to the control is about 80%, preferably 50% (i.e., 0.5× the activity of the control), more preferably 25%, more preferably 5–0%. Modulation/activation of gene expression is achieved when the gene expression activity value relative to the control is 110%, more preferably 150% (i.e., 1.5× the activity of the control), more preferably 200–500%, more preferably 1000–2000% or more.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV") thymidine kinase ("tk") promoter or a mutated HSV tk promoter, as described in Eisenberg & McKnight, *Mol. Cell. Biol.* 5:1940–1947 (1985).

A "transcriptional activator" and a "transcriptional repressor" refer to proteins or functional fragments of proteins that have the ability to modulate transcription, as described above. Such proteins include, e.g., transcription factors and co-factors (e.g., KRAB, MAD, ERD, SfD, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., *Nature* 394:498–502 (1998)).

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a DNA-binding domain (e.g., a ZFP) to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245–246; U.S. Pat. No. 5,585,245 and PCT WO 98/44350.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the terms "operatively linked" and "operably linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains a ZFP or an expression vector or nucleic acid encoding a ZFP. The host cell typically supports the replication or expression of the expression vector. Host cells may be prokaryotic cells such as E. coli, or eukaryotic cells such as fungal cells (e.g., yeast), protozoal cells, plant cells, insect cells, animal cells, avian cells, teleost cells, amphibian cells, mammalian cells, primate cells or human cells. Exemplary mammalian cell lines include CHO, HeLa, 293, COS-1, and the like, e.g., cultured cells (in vitro), explants and primary cultures (in vitro and ex vivo), and cells in vivo.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid and nucleic acid sequences, individual substitutions, deletions or additions that alter, add or delete a single amino acid or nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, Proteins (1984) for a discussion of amino acid properties).

Design of ZFPs

The ZFPs disclosed herein are engineered to recognize a selected target site in the endogenous gene of choice. Typically, a backbone from any suitable $C_2H_2$ ZFP, such as SP-1, SP-1C, or ZIF268, is used as the scaffold for the engineered ZFP (see, e.g., Jacobs, *EMBO J.* 11:4507 (1992); Desjarlais & Berg, *PNAS* 90:2256–2260 (1993)). A number of methods can then be used to design and select a ZFP with high affinity for its target (e.g., preferably with a $K_d$ of less than about 25 nM). As described above, a ZFP can be designed or selected to bind to any suitable target site in the target endogenous gene, with high affinity. Co-owned PCT WO 00/42219, herein incorporated by reference in its entirety, comprehensively describes methods for design, construction, and expression of ZFPs for selected target sites.

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *PNAS* 92:344–348 (1995); Jamieson et al., *Biochemistry* 33:5689–5695 (1994); Rebar & Pabo, *Science* 263:671–673 (1994); Choo & Klug, *PNAS* 91:11163–11167 (1994); Choo & Klug, *PNAS* 91: 11168–11172 (1994); Desjarlais & Berg, *PNAS* 90:2256–2260 (1993); Desjarlais & Berg, *PNAS* 89:7345–7349 (1992); Pomerantz et al., *Science* 267:93–96 (1995); Pomerantz et al., *PNAS* 92:9752–9756 (1995); and Liu et al., *PNAS* 94:5525–5530 (1997); Griesman & Pabo, *Science* 275:657–661 (1997); Desjarlais & Berg, *PNAS* 91:11–99–11103 (1994)).

In a preferred embodiment, co-owned PCT WO 00/42219 provides methods that select a target gene, and identify a target site within the gene containing one to six (or more) D-able sites (see definition below). Using these methods, a ZFP can then be synthesized that binds to the preselected site. These methods of target site selection are premised, in part, on the recognition that the presence of one or more D-able sites in a target segment confers the potential for higher binding affinity in a ZFP selected or designed to bind to that site relative to ZFPs that bind to target segments lacking D-able sites. Experimental evidence supporting this insight is provided in Examples 2–9 of co-owned PCT WO 00/42219.

A D-able site or subsite is a region of a target site that allows an appropriately designed single zinc finger to bind to four bases rather than three of the target site. Such a zinc finger binds to a triplet of bases on one strand of a double-stranded target segment (target strand) and a fourth base on the other strand (see FIG. 2 of co-owned PCT WO 00/42219). Binding of a single zinc finger to a four base target segment imposes constraints both on the sequence of the target strand and on the amino acid sequence of the zinc finger. The target site within the target strand should include the "D-able" site motif 5' NNGK 3' (SEQ ID NO:41), in which N and K are conventional IUPAC-IUB ambiguity codes. A zinc finger for binding to such a site should include an arginine residue at position −1 and an aspartic acid, (or less preferably a glutamic acid) at position +2. The arginine residues at position −1 interacts with the G residue in the D-able site. The aspartic acid (or glutamic acid) residue at position +2 of the zinc finger interacts with the opposite strand base complementary to the K base in the D-able site. It is the interaction between aspartic acid (symbol D) and the opposite strand base (fourth base) that confers the name D-able site. As is apparent from the D-able site formula, there are two subtypes of D-able sites: 5' NNGG 3' (SEQ ID NO:42) and 5' NNGT 3' (SEQ ID NO:43). For the former site, the aspartic acid or glutamic acid at position +2 of a zinc finger interacts with a C in the opposite strand to the D-able site. In the latter site, the aspartic acid or glutamic acid at position +2 of a zinc finger interacts with an A in the opposite strand to the D-able site. In general, NNGG (SEQ ID NO:42) is preferred over NNGT (SEQ ID NO:43).

In the design of a ZFP with three fingers, a target site should be selected in which at least one finger of the protein, and optionally, two or all three fingers have the potential to bind a D-able site. Such can be achieved by selecting a target site from within a larger target gene having the formula 5'-NNx aNy bNzc-3', wherein each of the sets (x, a), (y, b) and (z, c) is either (N, N) or (G, K);

at least one of (x, a), (y, b) and (z, c) is (G, K). and

N and K are IUPAC-IUB ambiguity codes

In other words, at least one of the three sets (x, a), (y, b) and (z, c) is the set (G, K), meaning that the first position of the set is G and the second position is G or T. Those of the three sets (if any) which are not (G, K) are (N, N), meaning that the first position of the set can be occupied by any nucleotide and the second position of the set can be occupied by any nucleotide. As an example, the set (x, a) can be (G, K) and the sets (y, b) and (z, c) can both be (N, N).

In the formula 5'-NNx aNy bNzc-3', the triplets of NNx aNy and bNzc represent the triplets of bases on the target strand bound by the three fingers in a ZFP. If only one of x, y and z is a G, and this G is followed by a K, the target site includes a single D-able subsite. For example, if only x is G, and a is K, the site reads 5'-NNG KNy bNzc-3' with the D-able subsite highlighted. If both x and y but not z are G, and a and b are K, then the target site has two overlapping D-able subsites as follows: 5'-NNG KNG KNz c-3' (SEQ ID NO:2), with one such site being represented in bold and the other in italics. If all three of x, y and z are G and a, b, and c are K, then the target segment includes three D-able subsites, as follows 5'NNG KNG KNG K3' (SEQ ID NO:3), the D-able subsites being represented by bold, italics and underline.

These methods thus work by selecting a target gene, and systematically searching within the possible subsequences of the gene for target sites conforming to the formula 5'-NNx aNy bNzc-3', as described above. In some such methods, every possible subsequence of 10 contiguous bases on either strand of a potential target gene is evaluated to determine whether it conforms to the above formula, and, if so, how many D-able sites are present. Typically, such a comparison is performed by computer, and a list of target sites conforming to the formula are output. Optionally, such target sites can be output in different subsets according to how many D-able sites are present.

In a variation, the methods identify first and second target segments, each independently conforming to the above formula. The two target segments in such methods are constrained to be adjacent or proximate (i.e., within about 0–5 bases) of each other in the target gene. The strategy underlying selection of proximate target segments is to allow the design of a ZFP formed by linkage of two component ZFPs specific for the first and second target segments respectively. These principles can be extended to select target sites to be bound by ZFPs with any number of component fingers. For example, a suitable target site for a nine finger protein would have three component segments, each conforming to the above formula.

The target sites identified by the above methods can be subject to further evaluation by other criteria or can be used directly for design or selection (if needed) and production of a ZFP specific for such a site. A further criteria for evaluating potential target sites is their proximity to particular regions within a gene. If a ZFP is to be used to repress a cellular gene on its own (i.e., without linking the ZFP to a repressing moiety), then the optimal location appears to be at, or within 50 bp upstream or downstream of the site of transcription initiation, to interfere with the formation of the transcription complex (Kim & Pabo, *J. Biol. Chem.* 272:29795–296800 (1997)) or compete for an essential enhancer binding protein. If, however, a ZFP is fused to a functional domain such as the KRAB repressor domain or the VP16 activator domain, the location of the binding site is considerably more flexible and can be outside known regulatory regions. For example, a KRAB domain can repress transcription at a promoter up to at least 3 kbp from where KRAB is bound (Margolin et al., *PNAS* 91:4509–4513 (1994)). Thus, target sites can be selected that do not necessarily include or overlap segments of demonstrable biological significance with target genes, such as regulatory sequences. Other criteria for further evaluating target segments include the prior availability of ZFPs binding to such segments or related segments, and/or ease of designing new ZFPs to bind a given target segment.

After a target segment has been selected, a ZFP that binds to the segment can be provided by a variety of approaches. The simplest of approaches is to provide a precharacterized ZFP from an existing collection that is already known to bind to the target site. However, in many instances, such ZFPs do not exist. An alternative approach can also be used to design new ZFPs, which uses the information in a database of existing ZFPs and their respective binding affinities. A further approach is to design a ZFP based on substitution rules as discussed above. A still further alternative is to select a ZFP with specificity for a given target by an empirical process such as phage display. In some such methods, each component finger of a ZFP is designed or selected independently of other component fingers. For example, each finger can be obtained from a different preexisting ZFP or each finger can be subject to separate randomization and selection.

Once a ZFP has been selected, designed, or otherwise provided to a given target segment, the ZFP or the DNA encoding it are synthesized. Exemplary methods for synthesizing and expressing DNA encoding zinc finger proteins are described below. The ZFP or a polynucleotide encoding it can then be used for modulation of expression, or analysis of the target gene containing the target site to which the ZFP binds. Expression and purification of ZFPs ZFP polypeptides and nucleic acids can be made using routine techniques in the field of recombinant genetics. Basic texts disclosing the general methods of use in the field include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding peptides. One protocol is a PCR-based assembly procedure that utilizes six overlapping oligonucleotides (FIG. 1). Three oligonucleotides (oligos 1, 3, and 5 in FIG. 1) correspond to "universal" sequences that encode portions of the DNA-binding domain between the recognition helices. These oligonucleotides remain constant for all zinc finger constructs. The other three "specific" oligonucleotides (oligos 2, 4, and 6 in FIG. 1) are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by highfidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions, but kinasing can also occur post-annealing. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment.

The resulting fragment encoding the newly designed ZFP is ligated into an expression vector. Expression vectors that are commonly utilized include, but are not limited to, a modified pMAL-c2 bacterial expression vector (New England BioLabs, "NEB") or a eukaryotic expression vector, pcDNA (Promega).

Any suitable method of protein purification known to those of skill in the art can be used to purify ZFPs (see Ausubel, supra, Sambrook, supra). In addition, any suitable host can be used, e.g., bacterial cells, insect cells, yeast cells, mammalian cells, and the like.

In one embodiment, expression of the ZFP fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the IPTG inducible tac promoter (NEB). Bacteria containing the MBP-ZFP fusion plasmids are inoculated in to 2xYT medium containing 10 $\mu$M $ZnCl_2$, 0.02% glucose, plus 50 $\mu$g/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 $\mu$M $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in *Current Protocols in Molecular Biology* pp. 12.2.1–12.2.7 (Ausubel ed., 1996); see also U.S. Pat. No. 5,789,538, co-owned PCT WO 00/42219 herein incorporated by reference in its entirety, and Example 1). Affinity is measured by titrating purified protein against a low fixed amount of labeled double-stranded oligonucleotide target. The target comprises the natural binding site sequence (9 or 18 bp) flanked by the 3 bp found in the natural sequence. External to the binding site plus flanking sequence is a constant sequence. The annealed oligonucleotide targets possess a 1 bp 5' overhang which allows for efficient labeling of the target with T4 phage polynucleotide kinase. For the assay the target is added at a concentration of 40 nM or lower (the actual concentration is kept at least 10-fold lower than the lowest protein dilution) and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA (poly (dIdC) or (dAdT) (Pharmacia) can also added at 10–100 $\mu$g/$\mu$l).

The equilibrated reactions are loaded onto a 10% polyacrylamide gel, which has been pre-run for 45 min in Tris/glycine buffer, then bound and unbound labeled target is resolved be electrophoresis at 150V (alternatively, 10–20% gradient Tris-HCl gels, containing a 4% polyacrylamide stacker, can be used). The dried gels are visualized by autoradiography or phosphoroimaging and the apparent $K_d$ is determined by calculating the protein concentration that gives half-maximal binding.

Similar assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

In another embodiment, phage display libraries can be used to select ZFPs with high affinity to the selected target site. This method differs fundamentally from direct design in that it involves the generation of diverse libraries of mutagenized ZFPs, followed by the isolation of proteins with desired DNA-binding properties using affinity selection methods. To use this method, the experimenter typically proceeds as follows.

First, a gene for a ZFP is mutagenized to introduce diversity into regions important for binding specificity and/or affinity. In a typical application, this is accomplished via randomization of a single finger at positions −1, +2, +3, and +6, and perhaps accessory positions such as +1, +5, +8, or +10.

Next, the mutagenized gene is cloned into a phage or phagemid vector as a fusion with, e.g., gene III of filamentous phage, which encodes the coat protein pIII. The zinc finger gene is inserted between segments of gene III encoding the membrane export signal peptide and the remainder of pIII, so that the ZFP is expressed as an amino-terminal fusion with pIII in the mature, processed protein. When using phagemid vectors, the mutagenized zinc finger gene may also be fused to a truncated version of gene III encoding, minimally, the C-terminal region required for assembly of pill into the phage particle.

The resultant vector library is transformed into *E. coli* and used to produce filamentous phage which express variant ZFPs on their surface as fusions with the coat protein pIII (if a phagemid vector is used, then the this step requires superinfection with helper phage). The phage library is then incubated with target DNA site, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which totally disrupt zinc finger-DNA binding.

Recovered phage are used to infect fresh *E. coli*, which is then amplified and used to produce a new batch of phage particles. The binding and recovery steps are then repeated as many times as is necessary to sufficiently enrich the phage pool for tight binders such that these may be identified using sequencing and/or screening methods.

Regulatory Domains

Binding domains such as, for example, ZFPs can optionally be associated with regulatory domains for modulation of gene expression. The ZFP can be covalently or non-covalently associated with one or more regulatory domains, alternatively two or more regulatory domains, with the two or more domains being two copies of the same domain, or two different domains. The regulatory domains can be covalently linked to the ZFP, e.g., via an amino acid linker, as part of a fusion protein. The ZFPs can also be associated with a regulatory domain via a non-covalent dimerization domain, e.g., a leucine zipper, a STAT protein N terminal domain, or an FK506 binding protein (see, e.g., O'Shea, *Science* 254: 539 (1991), Barahmand-Pour et al., *Curr. Top. Microbiol. Immunol.* 211:121–128 (1996); Klemm et al., *Annu. Rev. Immunol.* 16:569–592 (1998); Klemm et al., *Annu. Rev. Immunol.* 16:569–592 (1998); Ho et al., *Nature* 382:822–826 (1996); and Pomeranz et al., *Biochem.* 37:965 (1998)). The regulatory domain can be associated with the ZFP at any suitable position, including the C- or N-terminus of the ZFP.

Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825–30 (1996) for a review of proteins and nucleic acid elements involved in transcription; transcription factors in general are reviewed in Barnes & Adcock, *Clin. Exp. Allergy* 25 Suppl. 2:46–9 (1995) and Roeder, *Methods Enzymol.* 273:165–71 (1996)). Databases dedicated to transcription factors are known (see, e.g., *Science* 269:630 (1995)). Nuclear hormone receptor transcription factors are described in, for example, Rosen et al., *J. Med. Chem.* 38:4855–74 (1995). The C/EBP family of transcription factors are reviewed in Wedel et al., *Immunobiology* 193:171–85 (1995). Coactivators and co-repressors that mediate transcription regulation by nuclear hormone receptors are reviewed in, for example, Meier, *Eur. J. Endocrinol.* 134(2):158–9 (1996); Kaiser et al., *Trends Biochem. Sci.* 21:342–5 (1996); and Utley et al., *Nature* 394:498–502 (1998)). GATA transcription factors, which are involved in regulation of hematopoiesis, are described in, for example, Simon, *Nat. Genet.* 11:9–11 (1995); Weiss et al., *Exp. Hematol.* 23:99–107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403–9 (1994) and Hurley, *Curr. Opin. Struct. Biol.* 6:69–75 (1996). The STAT family of transcription factors are reviewed in, for example, Barahmand-Pour et al., *Curr. Top. Microbiol. Immunol.* 211:121–8 (1996). Transcription factors involved in disease are reviewed in Aso et al., *J. Clin. Invest.* 97:1561–9 (1996).

In one embodiment, the KRAB repression domain from the human KOX-1 protein is used as a transcriptional repressor (Thiesen et al., *New Biologist* 2:363–374 (1990); Margolin et al., *PNAS* 91:4509–4513 (1994); Pengue et al., *Nucl. Acids Res.* 22:2908–2914 (1994); Witzgall et al., *PNAS* 91:4514–4518 (1994); see also Example 3)). In another embodiment, KAP-1, a KRAB co-repressor, is used with KRAB (Friedrnan et al., *Genes Dev.* 10:2067–2078 (1996)). Alternatively, KAP-1 can be used alone with a ZFP. Other preferred transcription factors and transcription factor domains that act as transcriptional repressors include MAD (see, e.g., Sommer et al., *J. Biol. Chem.* 273:6632–6642 (1998); Gupta et al., *Oncogene* 16:1149–1159 (1998); Queva et al., *Oncogene* 16:967–977 (1998); Larsson et al., *Oncogene* 15:737–748 (1997); Laherty et al., *Cell* 89:349–356 (1997); and Cultraro et al., *Mol Cell. Biol.* 17:2353–2359 (19977)); FKHR (forkhead in rhapdosarcoma gene; Ginsberg et al., *Cancer Res.* 15:3542–3546 (1998); Epstein et al., *Mol. Cell. Biol.* 18:4118–4130 (1998)); EGR-1 (early growth response gene product-1; Yan et al., *PNAS* 95:8298–8303 (1998); and Liu et al., *Cancer Gene Ther.* 5:3–28 (1998)); the ets2 repressor factor repressor domain (ERD; Sgouras et al., *EMBO J.* 14:4781–4793 ((19095)); and the MAD smSIN3 interaction domain (SID; Ayer et al., *Mol. Cell. Biol.* 16:5772–5781 (1996)).

In one embodiment, the HSV VP16 activation domain is used as a transcriptional activator (see, e.g., Hagmann et al., *J. Virol.* 71:5952–5962 (1997)). Other preferred transcription factors that could supply activation domains include the VP64 activation domain (Seipel et al., *EMBO J.* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); and EGR-1 (early growth response gene product-1; Yan et al., *PNAS* 95:8298–8303 (1998); and Liu et al., *Cancer Gene Ther.* 5:3–28 (1998)).

Kinases, phosphatases, and other proteins that modify polypeptides involved in gene regulation are also useful as regulatory domains for ZFPs. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

As described, useful domains can also be obtained from the gene products of oncogenes (e.g., myc, Jun, fos, myb, max, mad, rel, ets, bcl, myb, mos family members) and their associated factors and modifiers. Oncogenes are described in, for example, Cooper, *Oncogenes*, 2nd ed., The Jones and Bartlett Series in Biology, Boston, Mass., Jones and Bartlett Publishers, 1995. The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors*, Angel & Herrlich, eds. (1994). The max oncogene is reviewed in Hurlin et al., Cold Spring Harb. Symp. Quant. Biol. 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

ZFPs can include regulatory domains obtained from DNA repair enzymes and their associated factors and modifiers. DNA repair systems are reviewed in, for example, Vos, *Curr. Opin. Cell Biol.* 4:385–95 (1992); Sancar, *Ann. Rev. Genet.* 29:69–105 (1995); Lehmann, *Genet. Eng.* 17:1–19 (1995); and Wood, *Ann. Rev. Biochem.* 65:135–67 (1996). DNA rearrangement enzymes and their associated factors and modifiers can also be used as regulatory domains (see, e.g., Gangloff et al., *Experientia* 50:261–9 (1994); Sadowski, *FASEB J.* 7:760–7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays*, 16:13–22 (1994), and methyltransferases are described in Cheng, *Curr. Opin. Struct. Biol.* 5:4–10 (1995). Chromatin associated proteins and their modifiers (e.g., kinases, acetylases and deacetylases), such as histone deacetylase (Wolffe, *Science* 272:371–2 (1996)) are also useful as domains for addition to the ZFP of choice. In one preferred embodiment, the regulatory domain is a DNA methyl transferase that acts as a transcriptional repressor (see, e.g., Van den Wyngaert et al., *FEBS Lett.* 426:283–289 (1998); Flynn et al., *J. Mol. Biol.* 279:101–116 (1998); Okano et al., *Nucleic Acids Res.* 26:2536–2540 (1998); and Zardo & Caiafa, *J. Biol. Chem.* 273:16517–16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, *Mol. Cell. Biol.* 18:4377–4384 (1998); Wolffe, *Science* 272:371–372 (1996); Taunton et al, *Science* 272:408–411 (1996); and Hassig et al., *PNAS* 95:3519–3524 (1998)). In another embodiment, histone deacetylase is used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

Another suitable repression domain is methyl binding domain protein 2B (MBD-2B) (see, also Hendrich et al. (1999) *Mamm Genome* 10:906–912 for description of MBD proteins). Another useful repression domain is that associated with the v-ErbA protein (see infra). See, for example, Damm, et al. (1989) *Nature* 339:593–597; Evans (1989) *Int. J. Cancer Suppl.* 4:26–28; Pain et al. (1990) *New Biol.* 2:284–294; Sap et al. (1989) *Nature* 340:242–244; Zenke et al. (1988) *Cell* 52:107–119; and Zenke et al. (1990) *Cell* 61:1035–1049. Additional exemplary repression domains include, but are not limited to, thyroid hormone receptor (TR, see infra), SID, MBD1, MBD2, MBD3, MBD4, MBD-like proteins, members of the DNMT family (e.g., DNMT1, DNMT3A, DNMT3B), Rb, MeCP1 and MeCP2. See, for example, Bird et al. (1999) *Cell* 99:451–454; Tyler et al. (1999) *Cell* 99:443–446; Knoepfler et al. (1999) *Cell* 99:447–450; and Robertson et al. (2000) *Nature Genet.* 25:338–342. Additional exemplary repression domains include, but are not limited to, ROM2 and AtHD2A. See, for example, Chern et al (1996) *Plant Cell* 8:305–321; and Wu et al. (2000) *Plant J*. 22:19–27.

Certain members of the nuclear hormone receptor (NHR) superfamily, including, for example, thyroid hormone receptors (TRs) and retinoic acid receptors (RARs) are among the most potent transcriptional regulators currently known. Zhang et al., *Annu. Rev. Physiol.* 62:439–466 (2000) and Sucov et al., *Mol Neurobiol* 10(2–3):169–184 (1995). In the absence of their cognate ligand, these proteins bind with high specificity and affinity to short stretches of DNA (e.g., 12–17 base pairs) within regulatory loci (e.g., enhancers and promoters) and effect robust transcriptional repression of adjacent genes. The potency of their regulatory action stems from the concurrent use of two distinct functional pathways to drive gene silencing: (i) the creation of a localized domain of repressive chromatin via the targeting of a complex between the corepressor N-CoR and a histone deacetylase, HDAC3 (Guenther et al., *Genes Dev* 14:1048–1057 (2000); Urnov et al., *EMBO J* 19:4074–4090 (2000); Li et al., *EMBO J* 19, 4342–4350 (2000) and Underhill et al., *J. Biol. Chem.* 275:40463–40470 (2000)) and (ii) a chromatin-independent pathway (Urnov et al., supra) that may involve direct interference with the function of the basal transcription machinery (Fondell et al., *Genes Dev* 7(7B): 1400–1410 (1993) and Fondell et al., *Mol Cell Biol* 16:281–287 (1996).

In the presence of very low (e.g., nanomolar) concentrations of their ligand, these receptors undergo a conformational change which leads to the release of corepressors, recruitment of a different class of auxiliary molecules (e.g., coactivators) and potent transcriptional activation. Collingwood et al., *J. Mol. Endocrinol.* 23(3):255–275 (1999).

The portion of the receptor protein responsible for transcriptional control (e.g., repression and activation) can be physically separated from the portion responsible for DNA binding, and retains full functionality when tethered to other polypeptides, for example, other DNA-binding domains. Accordingly, a nuclear hormone receptor transcription control domain can be fused to a ZFP DNA-binding domain such that the transcriptional regulatory activity of the receptor can be targeted to a chromosomal region of interest (e.g., a gene) by virtue of the ZFP binding domain.

Moreover, the structure of TR and other nuclear hormone receptors can be altered, either naturally or through recombinant techniques, such that it loses all capacity to respond to hormone (thus losing its ability to drive transcriptional activation), but retains the ability to effect transcriptional repression. This approach is exemplified by the transcriptional regulatory properties of the oncoprotein v-ErbA. The v-ErbA protein is one of the two proteins required for leukemic transformation of immature red blood cell precursors in young chicks by the avian erythroblastosis virus. TR is a major regulator of erythropoiesis (Beug et al., *Biochim Biophys Acta* 1288(3):M35–47 (1996); in particular, in its unliganded state, it represses genes required for cell cycle arrest and the differentiated state. Thus, the administration of thyroid hormone to immature erythroblasts leads to their rapid differentiation. The v-ErbA oncoprotein is an extensively mutated version of TR; these mutations include: (i) deletion of 12 amino-terminal amino acids; (ii) fusion to the gag oncoprotein; (iii) several point mutations in the DNA binding domain that alter the DNA binding specificity of the protein relative to its parent, TR, and impair its ability to heterodimerize with the retinoid X receptor; (iv) multiple point mutations in the ligand-binding domain of the protein that effectively eliminate the capacity to bind thyroid hormone; and (v) a deletion of a carboxy-terminal stretch of amino acids that is essential for transcriptional activation. Stunnenberg et al., *Biochim Biophys Acta* 1423(1):F15–33 (1999). As a consequence of these mutations, v-ErbA retains the capacity to bind to naturally occurring TR target genes and is an effective transcriptional repressor when bound (Umov et al., supra; Sap et al., *Nature* 340:242–244 (1989); and Ciana et al., *EMBO J.* 17(24):7382–7394 (1999). In contrast to TR, however, v-ErbA is completely insensitive to thyroid hormone, and thus maintains transcriptional repression in the face of a challenge from any concentration of thyroids or retinoids, whether endogenous to the medium, or added by the investigator (4).

We have shown that this functional property of v-ErbA is retained when its repression domain is fused to a heterologous, synthetic DNA binding domain. See Example 9. Accordingly, in one aspect, v-ErbA or its functional fragments are used as a repression domain. In additional embodiments, TR or its functional domains are used as a repression domain in the absence of ligand and/or as an activation domain in the presence of ligand (e.g., 3,5,3'-triiodo-L-thyronine or T3). Thus, TR can be used as a switchable functional domain (i.e., a bifunctional domain); its activity (activation or repression) being dependent upon the presence or absence (respectively) of ligand. See Example 13.

Additional exemplary repression domains are obtained from the DAX protein and its functional fragments. Zazopoulos et al., *Nature* 390:311–315 (1997). In particular, the C-terminal portion of DAX-1, including amino acids 245–470, has been shown to possess repression activity. Altincicek et al., *J. Biol. Chem.* 275:7662–7667 (2000). A further exemplary repression domain is the RBP1 protein and its functional fragments. Lai et al., *Oncogene* 18:2091–2100 (1999); Lai et al., *Mol. Cell. Biol.* 19:6632–6641 (1999); Lai et al., *Mol. Cell. Biol.* 21:2918–2932 (2001) and WO 01/04296. The full-length RBP1 polypeptide contains 1257 amino acids. Exemplary functional fragments of RBP1 are a polypeptide comprising amino acids 1114–1257, and a polypeptide comprising amino acids 243–452.

Members of the TIEG family of transcription factors contain three repression domains known as R1, R2 and R3. Repression by TIEG family proteins is achieved at least in part through recruitment of mSIN3A histone deacetylases complexes. Cook et al. (1999) *J. Biol. Chem.* 274:29,500–29,504; Zhang et al. (2001) *Mol. Cell. Biol.* 21:5041–5049. Any or all of these repression domains (or their functional fragments) can be fused alone, or in combination with additional repression domains (or their functional fragments), to a DNA-binding domain to generate a targeted exogenous repressor molecule.

Furthermore, the product of the human cytomegalovirus (HCMV) UL34 open reading frame acts as a transcriptional repressor of certain HCMV genes, for example, the US3 gene. LaPierre et al. (2001) *J. Virol.* 75:6062–6069. Accordingly, the UL34 gene product, or functional fragments thereof, can be used as a component of a fusion polypeptide also comprising a zinc finger binding domain. Nucleic acids encoding such fusions are also useful in the methods and compositions disclosed herein.

Yet another exemplary repression domain is the CDF-1 transcription factor and/or its functional fragments. See, for example, WO 99/27092.

The Ikaros family of proteins are involved in the regulation of lymphocyte development, at least in part by transcriptional repression. Accordingly, an Ikaros family member (e.g., Ikaros, Aiolos) or a functional fragment thereof, can be used as a repression domain. See, for example, Sabbattini et al. (2001) *EMBO J.* 20:2812–2822.

The yeast Ash1p protein comprises a transcriptional repression domain. Maxon et al. (2001) *Proc. Natl. Acad. Sci. USA* 98:1495–1500. Accordingly, the Ash1p protein, its functional fragments, and homologues of Ash1p, such as those found, for example, in, vertebrate, mammalian, and plant cells, can serve as a repression domain for use in the methods and compositions disclosed herein.

Additional exemplary repression domains include those derived from histone deacetylases (HDACs, e.g., Class I HDACs, Class II HDACs, SIR-2 homologues), HDAC-interacting proteins (e.g., SIN3, SAP30, SAP15, NCoR, SMRT, RB, p107, p130, RBAP46/48, MTA, Mi-2, Brg1, Brm), DNA-cytosine methyltransferases (e.g., Dnmt1, Dnmt3a, Dnmt3b), proteins that bind methylated DNA (e.g., MBD1, MBD2, MBD3, MBD4, MeCP2, DMAP1), protein methyltransferases (e.g., lysine and arginine methylases, SuVar homologues such as Suv39H1), polycomb-type repressors (e.g., Bmi-1, eed1, RING1, RYBP, E2F6, Me118, YY1 and CtBP), viral repressors (e.g., adenovirus E1b 55K protein, cytomegalovirus UL34 protein, viral oncogenes such as v-erbA), hormone receptors (e.g., Dax-1, estrogen receptor, thyroid hormone receptor), and repression domains associated with naturally-occurring zinc finger proteins (e.g., WT1, KAP1). Further exemplary repression domains include members of the polycomb complex and their homologues, HPH1, HPH2, HPC2, NC2, groucho, Eve, tramtrak, mHP1, SIP1, ZEB1, ZEB2, and Enx1/Ezh2. In all of these cases, either the full-length protein or a functional fragment can be used as a repression domain for fusion to a zinc finger binding domain. Furthermore, any homologues of the aforementioned proteins can also be used as repression domains, as can proteins (or their functional fragments) that interact with any of the aforementioned proteins.

Additional repression domains, and exemplary functional fragments, are as follows. Hes1 is a human homologue of the Drosophila hairy gene product and comprises a functional fragment encompassing amino acids 910–1014. In particular, a WRPW (trp-arg-pro-trp) motif can act as a repression domain. Fisher et al. (1996) *Mol. Cell. Biol.* 16:2670–2677.

The TLE1, TLE2 and TLE3 proteins are human homologues of the *Drosophila groucho* gene product. Functional fragments of these proteins possessing repression activity reside between amino acids 1–400. Fisher et al., supra.

The Tbx3 protein possesses a functional repression domain between amino acids 524–721. He et al. (1999) *Proc. Natl. Acad. Sci. USA* 96:10,212–10,217. The Tbx2 gene product is involved in repression of the p14/p16 genes and contains a region between amino acids 504–702 that is homologous to the repression domain of Tbx3; accordingly Tbx2 and/or this functional fragment can be used as a repression domain. Carreira et al. (1998) *Mol. Cell. Biol.* 18:5,099–5,108.

The human Ezh2 protein is a homologue of Drosophila enhancer of zeste and recruits the eed1 polycomb-type repressor. A region of the Ezh2 protein comprising amino acids 1–193 can interact with eed1 and repress transcription; accordingly Ezh2 and/or this functional fragment can be used as a repression domain. Denisenko et al. (1998) *Mol. Cell. Biol.* 18:5634–5642.

The RYBP protein is a corepressor that interacts with polycomb complex members and with the YY1 transcription factor. A region of RYBP comprising amino acids 42–208 has been identified as functional repression domain. Garcia et al. (1999) *EMBO J*. 18:3404–3418.

The RING finger protein RING1A is a member of two different vertebrate polycomb-type complexes, contains multiple binding sites for various components of the polycomb complex, and possesses transcriptional repression activity. Accordingly, RING1A or its functional fragments can serve as a repression domain. Satjin et al. (1997) *Mol. Cell. Biol.* 17:4105–4113.

The Bmi-1 protein is a member of a vertebrate polycomb complex and is involved in transcriptional silencing. It contains multiple binding sites for various polycomb complex components. Accordingly, Bmi-1 and its functional fragments are useful as repression domains. Gunster et al. (1997) *Mol. Cell. Biol.* 17:2326–2335; Hemenway et al. (1998) *Oncogene* 16:2541–2547.

The E2F6 protein is a member of the mammalian Bmi-1-containing polycomb complex and is a transcriptional repressor that is capable or recruiting RYBP, Bmi-1 and RING1A. A functional fragment of E2F6 comprising amino acids 129–281 acts as a transcriptional repression domain. Accordingly, E2F6 and its functional fragments can be used as repression domains. Trimarchi et al. (2001) *Proc Natl. Acad. Sci. USA* 98:1519–1524.

The eed1 protein represses transcription at least in part through recruitment of histone deacetylases (e.g., HDAC2). Repression activity resides in both the N- and C-terminal regions of the protein. Accordingly, eed1 and its functional fragments can be used as repression domains. van der Vlag et al. (1999) *Nature Genet*. 23:474–478.

The CTBP2 protein represses transcription at least in part through recruitment of an HPC2-polycomb complex. Accordingly, CTBP2 and its functional fragments are useful as repression domains. Richard et al. (1999) *Mol. Cell. Biol.* 19:777–787.

Neuron-restrictive silencer factors are proteins that repress expression of neuron-specific genes. Accordingly, a NRSF or functional fragment thereof can serve as a repression domain. See, for example, U.S. Pat. No. 6,270,990.

It will be clear to those of skill in the art that, in the formation of a fusion protein (or a nucleic acid encoding same) between a zinc finger binding domain and a functional domain, either a repressor or a molecule that interacts with a repressor is suitable as a functional domain. Essentially any molecule capable of recruiting a repressive complex and/or repressive activity (such as, for example, histone deacetylation) to the target gene is useful as a repression domain of a fusion protein.

Additional exemplary activation domains include, but are not limited to, p300, CBP, PCAF, SRC1 PvALF, AtHD2A and ERF-2. See, for example, Robyr et al. (2000) *Mol. Endocrinol.* 14:329–347; Collingwood et al. (1999) *J. Mol. Endocrinol.* 23:255–275; Leo et al. (2000) *Gene* 245:1–11; Manteuffel-Cymborowska (1999) *Acta Biochim. Pol.* 46:77–89; McKenna et al. (1999) *J. Steroid Biochem. Mol. Biol.* 69:3–12; Malik et al. (2000) *Trends Biochem. Sci.* 25:277–283; and Lemon et al. (1999) *Curr. Opin. Genet. Dev.* 9:499–504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21–29; Okanami et al. (1996) *Genes Cells* 1:87–99; Goff et al. (1991) *Genes Dev*. 5:298–309; Cho et al. (1999) *Plant Mol. Biol.* 40:419–429; Ulmason et al. (1999) *Proc. Natl. Acad. Sci. USA* 96:5844–5849; Sprenger-Haussels et al. (2000) *Plant J*. 22:1–8; Gong et al. (1999) *Plant Mol. Biol.* 41:33–44; and Hobo et al. (1999) *Proc. Natl. Acad. Sci. USA* 96:15,348–15,353.

It will be clear to those of skill in the art that, in the formation of a fusion protein (or a nucleic acid encoding same) between a zinc finger binding domain and a functional domain, either an activator or a molecule that interacts with an activator is suitable as a functional domain. Essentially any molecule capable of recruiting an activating complex and/or activating activity (such as, for example, histone acetylation) to the target gene is useful as an activating domain of a fusion protein.

Insulator domains, chromatin remodeling proteins such as ISWI-containing domains and/or methyl binding domain proteins suitable for use as functional domains in fusion molecules are described, for example, in co-owned PCT application US01/40616 and co-owned U.S. patent application Nos. 60/236,409; 60/236,884; and 60/253,678.

In a further embodiment, a DNA-binding domain (e.g., a zinc finger domain) is fused to a bifunctional domain (BFD). A bifunctional domain is a transcriptional regulatory domain whose activity depends upon interaction of the BFD with a second molecule. The second molecule can be any type of molecule capable of influencing the functional properties of the BFD including, but not limited to, a compound, a small molecule, a peptide, a protein, a polysaccharide or a nucleic acid. An exemplary BFD is the ligand binding domain of the estrogen receptor (ER). In the presence of estradiol, the ER ligand binding domain acts as a transcriptional activator; while, in the absence of estradiol and the presence of tamoxifen or 4-hydroxy-tamoxifen, it acts as a transcriptional repressor. Another example of a BFD is the thyroid hormone receptor (TR) ligand binding domain which, in the absence of ligand, acts as a transcriptional repressor and in the presence of thyroid hormone (T3), acts as a transcriptional activator. An additional BFD is the glucocorticoid receptor (GR) ligand binding domain. In the presence of dexamethasone, this domain acts as a transcriptional activator; while, in the presence of RU486, it acts as a transcriptional repressor. An additional exemplary BFD is the ligand binding domain of the retinoic acid receptor. In the presence of its ligand all-trans-retinoic acid, the retinoic acid receptor recruits a number of co-activator complexes and activates transcription. In the absence of ligand, the retinoic acid receptor is not capable of recruiting transcriptional co-activators. Additional BFDs are known to those of skill in the art. See, for example, U.S. Pat. Nos. 5,834,266 and 5,994,313 and PCT WO 99/10508.

Linker domains between polypeptide domains, e.g., between two ZFPs or between a ZFP and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS (SEQ ID NO:4) is used to link two ZFPs. In another embodiment, the flexible linker linking two ZFPs is an amino acid subsequence comprising the sequence TGEKP (see, e.g., Liu et al., *PNAS* 5525–5530 (1997)). In another embodiment, the linker LRQKDGERP (SEQ ID NO:6) is used to link two ZFPs. In another embodiment, the following linkers are used to link two ZFPs: GGRR (SEQ ID NO:7) (Pomerantz et al. 1995, supra), (G4S)$_n$ (SEQ ID NO:8) (Kim et al., *PNAS* 93, 1156–1160 (1996).); and GGRRGGGS (SEQ ID NO:9); LRQRDGERP (SEQ ID NO:10); LRQKDGGGSERP (SEQ ID NO:11); LRQKd(G3 S)$_2$ ERP (SEQ ID NO:12). Alternatively, flexible linkers can be rationally designed using computer program capable of modeling both DNA-binding sites and the peptidesthemselves (Desjarlais & Berg, *PNAS* 90:2256–2260 (1993), *PNAS* 91:11099–11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to regulatory domains, non-covalent methods can be used to produce molecules with ZFPs associated with regulatory domains.

In addition to regulatory domains, often the ZFP is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

Expression Vectors

The nucleic acid encoding the ZFP of choice is typically cloned into intermediate vectors for transformation into prokaryotic or eukaryotic cells for replication and/or expression, e.g., for determination of $K_d$. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the ZFP are available in, e.g., *E. coli, Bacillus sp.*, and *Salmonella* (Palva et al., *Gene* 22:229–235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *PNAS* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the ZFP, e.g., expression in plants, animals, bacteria, fungus, protozoa etc. (see expression vectors described below and in the Example section). Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); Guide to Protein Purification, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Assays For Determining Regulation of Gene Expression

A variety of assays can be used to determine the level of gene expression regulation by ZFPs. The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, $Ca^{2+}$); cytokine and hormone production levels; and neovascularization, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to control samples without the test compound, to examine the extent of modulation. As described above, for regulation of endogenous gene expression, the ZFP typically has a $K_d$ of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay (see Examples 6 and 7). The test sample is compared to control cells treated with an empty vector or an unrelated ZFP that is targeted to another gene.

In another embodiment, ZFP regulation of endogenous gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment (see Example 8 and FIG. 10). The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining ZFPs that inhibit expression of tumor promoting genes, genes involved in tumor support, such as neovascularization (e.g., VEGF), or that activate tumor suppressor genes such as p53. In this assay, cultured tumor cells expressing the ZFP of choice are injected subcutaneously into an immune compromised mouse such as an athymic mouse, an irradiated mouse, or a SCID mouse. After a suitable length of time, preferably 4–8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used as a preferred embodiment for examining regulation of endogenous gene expression in vivo. Transgenic animals typically express the ZFP of choice. Alternatively, animals that transiently express the ZFP of choice, or to which the ZFP has been administered in a delivery vehicle, can be used. Regulation of endogenous gene expression is tested using any one of the assays described herein.

Nucleic Acids Encoding Fusion Proteins and Gene Therapy

Conventional viral and non-viral based gene transfer methods can be used to introduce nucleic acids encoding engineered ZFP in mammalian cells or target tissues. Such methods can be used to administer nucleic acids encoding ZFPs to cells in vitro. Preferably, the nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfler and Böhm (eds) (1995); and Yu et al., *Gene Therapy* 1:13–26 (1994).

Methods of non-viral delivery of nucleic acids encoding engineered ZFPs include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251–3260 (1985); Tratschin, et al., *Mol. Cell. Biol.* 4:2072–2081 (1984); Hermonat & Muzyczka, *PNAS* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *PNAS* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors. (Ellem et al., *Immunol Immunother.* 44(1): 10–20 (1997); Dranoff et al., *Hum. Gene Ther.* 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702–3 (1998), Kearns et al., *Gene Ther.* 9:748–55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 24:15–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693–1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693–1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

Delivery Vehicles

An important factor in the administration of polypeptide compounds, such as the ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629–634 (1996)). Another subsequence, the h (hydrophobic) domain of signal peptides, was found to have similar cell membrane translocation characteristics (see, e.g., Lin et al., *J. Biol. Chem.* 270:1 4255–14258 (1995)).

Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84–103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223–233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334–3341 (1993); Perelle et al., *Infect. Immun.*, 61:5147–5156 (1993); Stenmark et al., *J. Cell Biol.* 113:1025–1032 (1991); Donnelly et al., *PNAS* 90:3530–3534 (1993); Carbonetti et al., *Abstr. Annu. Meet. Am. Soc. Microbiol.* 95:295 (1995); Sebo et al., *Infect. Immun.* 63:3851–3857 (1995); Klimpel et al., *PNAS U.S.A.* 89:10277–10281 (1992); and Novak et al., *J. Biol. Chem.* 267:17186–17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629–634 (1976); Fraley, et al., *PNAS* 76:3348–3352 (1979); Hope et al., *Biochim. Biophys. Acta* 812:55–65 (1985); Mayer et al., *Biochim. Biophys. Acta* 858:161–168 (1986); Williams et al., *PNAS* 85:242–246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337–16342 (1990) and Leonetti et al., *PNAS* 87:2448–2451 (1990).

Dosages

For therapeutic applications, the dose administered to a patient, in the context of the present disclosure, should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy and $K_d$ of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

The maximum therapeutically effective dosage of ZFP for approximately 99% binding to target sites is calculated to be in the range of less than about $1.5 \times 10^5$ to $1.5 \times 10^6$ copies of the specific ZFP molecule per cell. The number of ZFPs per cell for this level of binding is calculated as follows, using the volume of a HeLa cell nucleus (approximately 1000 $\mu m^3$ or $10^{-12}$ L; *Cell Biology*, (Altman & Katz, eds. (1976)). As the HeLa nucleus is relatively large, this dosage number is recalculated as needed using the volume of the target cell nucleus. This calculation also does not take into account competition for ZFP binding by other sites. This calculation also assumes that essentially all of the ZFP is localized to the nucleus. A value of 100× $K_d$ is used to calculate approximately 99% binding of to the target site, and a value of 10× $K_d$ is used to calculate approximately 90% binding of to the target site. For this example, $K_d$=25 nM ZFP+target site ↔complex i.e., DNA+protein ↔DNA:protein complex $K_d$=[DNA][protein]

[DNA:protein complex]

When 50% of ZFP is bound, $K_d$=[protein]

So when [protein]=25 nM and the nucleus volume is $10^{-12}$ L

[protein]=$(25 \times 10^{-9}$ moles/L$)(10^{-12}$ L/nucleus$)(6 \times 10^{23}$ molecules/mole)=15,000 molecules/nucleus for 50% binding When 99% target is bound; 100× $K_d$=[protein]

100× $K_d$=[protein]=2.5 $\mu$M $(2.5 \times 10^{-6}$ moles/L$)(10^{-12}$ L/nucleus$)(6 \times 10^{23}$ molecules/mole)=about 1,500,000 molecules per nucleus for 99% binding of target site.

The appropriate dose of an expression vector encoding a ZFP can also be calculated by taking into account the average rate of ZFP expression from the promoter and the average rate of ZFP degradation in the cell. Preferably, a weak promoter such as a wild-type or mutant HSV TK is used, as described above. The dose of ZFP in micrograms is calculated by taking into account the molecular weight of the particular ZFP being employed.

In determining the effective amount of the ZFP to be administered in the treatment or prophylaxis of disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

Pharmaceutical Compositions and Administration

ZFPs and expression vectors encoding ZFPs can be administered directly to the patient for modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by ZFP gene therapy include pathogenic bacteria, e.g., chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria; infectious fungus, e.g., *Aspergillus, Candida* species; protozoa such as sporozoa (e.g., *Plasmodia*), rhizopods (e.g., *Entamoeba*) and flagellates (*Trypanosoma,* *Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Regulation of Gene Expression in Plants

ZFPs can be used to engineer plants for traits such as increased disease resistance, modification of structural and storage polysaccharides, flavors, proteins, and fatty acids, fruit ripening, yield, color, nutritional characteristics, improved storage capability, and the like. In particular, the engineering of crop species for enhanced oil production, e.g., the modification of the fatty acids produced in oilseeds, is of interest.

Seed oils are composed primarily of triacylglycerols (TAGs), which are glycerol esters of fatty acids. Commercial production of these vegetable oils is accounted for primarily by six major oil crops (soybean, oil palm, rapeseed, sunflower, cotton seed, and peanut.) Vegetable oils are used predominantly (90%) for human consumption as margarine, shortening, salad oils, and frying oil. The remaining 10% is used for non-food applications such as lubricants, oleochemicals, biofuels, detergents, and other industrial applications.

The desired characteristics of the oil used in each of these applications varies widely, particularly in terms of the chain length and number of double bonds present in the fatty acids making up the TAGs. These properties are manipulated by the plant in order to control membrane fluidity and temperature sensitivity. The same properties can be controlled using ZFPs to produce oils with improved characteristics for food and industrial uses.

The primary fatty acids in the TAGs of oilseed crops are 16 to 18 carbons in length and contain 0 to 3 double bonds. Palmitic acid (16:0 [16 carbons: 0 double bonds]), oleic acid (18:1), linoleic acid (18:2), and linolenic acid (18:3) predominate. The number of double bonds, or degree of saturation, determines the melting temperature, reactivity, cooking performance, and health attributes of the resulting oil.

The enzyme responsible for the conversion of oleic acid (18:1) into linoleic acid (18:2) (which is then the precursor for 18:3 formation) is $\Delta 12$-oleate desaturase, also referred to as omega-6 desaturase. A block at this step in the fatty acid desaturation pathway should result in the accumulation of oleic acid at the expense of polyunsaturates.

In one embodiment ZFPs are used to regulate expression of the FAD2-1 gene in soybeans. Two genes encoding microsomal $\Delta 6$ desaturases have been cloned recently from soybean, and are referred to as FAD2-1 and FAD2-2 (Heppard et al., *Plant Physiol.* 110:311–319 (1996)). FAD2-1 (delta 12 desaturase) appears to control the bulk of oleic acid desaturation in the soybean seed. ZFPs can thus be used to modulate gene expression of FAD2-1 in plants. Specifically, ZFPs can be used to inhibit expression of the FAD2-1 gene in soybean in order to increase the accumulation of oleic acid (18:1) in the oil seed. Moreover, ZFPs can be used to modulate expression of any other plant gene, such as delta-9 desaturase, delta-12 desaturases from other plants, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, polygalacturonase, EPSP synthase, plant viral genes, plant fungal pathogen genes, and plant bacterial pathogen genes.

Recombinant DNA vectors suitable for transformation of plant cells are also used to deliver protein (e.g., ZFP)-encoding nucleic acids to plant cells. Techniques for transforming a wide variety of higher plant species are well known and described in the technical and scientific literature (see, e.g., Weising et al. *Ann. Rev. Genet.* 22:421–477 (1988)). A DNA sequence coding for the desired ZFP is combined with transcriptional and translational initiation regulatory sequences which will direct the transcription of the ZFP in the intended tissues of the transformed plant.

For example, a plant promoter fragment may be employed which will direct expression of the ZFP in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35 S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the ZFP in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as fruit, seeds, or flowers. For example, the use of a polygalacturonase promoter can direct expression of the ZFP in the fruit, a CHS-A (chalcone synthase A from petunia) promoter can direct expression of the ZFP in flower of a plant.

The vector comprising the ZFP sequences will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717–2722 (1984). Electroporation techniques are described in Fromm et al. *PNAS* 82:5824 (1985). Biolistic transformation techniques are described in Klein et al. *Nature* 327:70–73 (1987).

*Agrobacterium tumefaciens*-meditated transformation techniques are well described in the scientific literature (see, e.g., Horsch et al *Science* 233:496–498 (1984)); and Fraley et al. *PNAS* 80:4803 (1983)).

Transformed plant cells which are derived by any of the above transformation techniques can be cultured to regenerate a whole plant which possesses the transformed genotype and thus the desired ZFP-controlled phenotype. Such regeneration techniques rely on manipulation of certain phytohormones in a tissue culture growth medium, typically relying on a biocide and/or herbicide marker which has been introduced together with the ZFP nucleotide sequences. Plant regeneration from cultured protoplasts is described in Evans et al., *Protoplasts Isolation and Culture, Handbook of Plant Cell Culture*, pp. 124–176 (1983); and Binding, *Regeneration of Plants, Plant Protoplasts*, pp. 21–73 (1985). Regeneration can also be obtained from plant callus, explants, organs, or parts thereof. Such regeneration techniques are described generally in Klee et al. *Ann. Rev. of Plant Phys.* 38:467–486 (1987).

Functional Genomics Assays

ZFPs also have use for assays to determine the phenotypic consequences and function of gene expression. The recent advances in analytical techniques, coupled with focussed mass sequencing efforts have created the opportunity to identify and characterize many more molecular targets than were previously available. This new information about genes and their functions will speed along basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. One can now very easily generate long lists of differentially expressed genes that correlate with a given physiological phenomenon, but demonstrating a causative relationship between an individual differentially expressed gene and the phenomenon is difficult. Until now, simple methods for assigning function to differentially expressed genes have not kept pace with the ability to monitor differential gene expression.

Using conventional molecular approaches, over expression of a candidate gene can be accomplished by cloning a full-length cDNA, subcloning it into a mammalian expression vector and transfecting the recombinant vector into an appropriate host cell. This approach is straightforward but labor intensive, particularly when the initial candidate gene is represented by a simple expressed sequence tag (EST). Under expression of a candidate gene by "conventional" methods is yet more problematic. Antisense methods and methods that rely on targeted ribozymes are unreliable, succeeding for only a small fraction of the targets selected. Gene knockout by homologous recombination works fairly well in recombinogenic stem cells but very inefficiently in somatically derived cell lines. In either case large clones of syngeneic genomic DNA (on the order of 10 kb) should be isolated for recombination to work efficiently.

The ZFP technology can be used to rapidly analyze differential gene expression studies. Engineered ZFPs can be readily used to up or down-regulate any endogenous target gene. Very little sequence information is required to create a gene-specific DNA binding domain. This makes the ZFP technology ideal for analysis of long lists of poorly characterized differentially expressed genes. One can simply build a zinc finger-based DNA binding domain for each candidate gene, create chimeric up and down-regulating artificial transcription factors and test the consequence of up or down-regulation on the phenotype under study (transformation, response to a cytokine etc.) by switching the candidate genes on or off one at a time in a model system.

This specific example of using engineered ZFPs to add functional information to genomic data is merely illustrative. Any experimental situation that could benefit from the specific up or down-regulation of a gene or genes could benefit from the reliability and ease of use of engineered ZFPs.

Additionally, greater experimental control can be imparted by ZFPs than can be achieved by more conventional methods. This is because the production and/or function of an engineered ZFP can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any endogenous gene of interest or any transgene by placing the function and/or expression of a ZFP regulator under small molecule control.

Transgenic Mice

A further application of the ZFP technology is manipulating gene expression in transgenic animals. As with cell lines, over-expression of an endogenous gene or the introduction of a heterologous gene to a transgenic animal, such as a transgenic mouse, is a fairly straightforward process. The ZFP technology is an improvement in these types of methods because one can circumvent the need for generating full-length cDNA clones of the gene under study.

Likewise, as with cell-based systems, conventional down-regulation of gene expression in transgenic animals is plagued by technical difficulties. Gene knockout by homologous recombination is the method most commonly applied currently. This method requires a relatively long genomic clone of the gene to be knocked out (ca. 10 kb). Typically, a selectable marker is inserted into an exon of the gene of interest to effect the gene disruption, and a second counter-selectable marker provided outside of the region of homology to select homologous versus non-homologous recombinants. This construct is transfected into embryonic stem cells and recombinants selected in culture. Recombinant stem cells are combined with very early stage embryos generating chimeric animals. If the chimerism extends to the germline homozygous knockout animals can be isolated by back-crossing. When the technology is successfully applied, knockout animals can be generated in approximately one year. Unfortunately two common issues often prevent the successful application of the knockout technology; embryonic lethality and developmental compensation. Embryonic lethality results when the gene to be knocked out plays an essential role in development. This can manifest itself as a lack of chimerism, lack of germline transmission or the inability to generate homozygous back crosses. Genes can play significantly different physiological roles during development versus in adult animals. Therefore, embryonic lethality is not considered a rationale for dismissing a gene target as a useful target for therapeutic intervention in adults. Embryonic lethality most often simply means that the gene of interest can not be easily studied in mouse models, using conventional methods.

Developmental compensation is the substitution of a related gene product for the gene product being knocked out. Genes often exist in extensive families. Selection or induction during the course of development can in some cases trigger the substitution of one family member for another mutant member. This type of functional substitution may not be possible in the adult animal. A typical result of developmental compensation would be the lack of a phenotype in a knockout mouse when the ablation of that gene's function in an adult would otherwise cause a physiological change. This is a kind of false negative result that often confounds the interpretation of conventional knockout mouse models.

A few new methods have been developed to avoid embryonic lethality. These methods are typified by an approach using the cre recombinase and lox DNA recognition elements. The recognition elements are inserted into a gene of interest using homologous recombination (as described above) and the expression of the recombinase induced in adult mice post-development. This causes the deletion of a portion of the target gene and avoids developmental complications. The method is labor intensive and suffers form chimerism due to non-uniform induction of the recombinase.

The use of engineered ZFPs to manipulate gene expression can be restricted to adult animals using the small molecule regulated systems described in the previous section. Expression and/or function of a zinc finger-based repressor can be switched off during development and switched on at will in the adult animals. This approach relies on the addition of the ZFP expressing module only; homologous recombination is not required. Because the ZFP repressors are trans dominant, there is no concern about germline transmission or homozygosity. These issues dramatically affect the time and labor required to go from a poorly characterized gene candidate (a cDNA or EST clone) to a mouse model. This ability can be used to rapidly identify and/or validate gene targets for therapeutic intervention, generate novel model systems and permit the analysis of complex physiological phenomena (development, hematopoiesis, transformation, neural function etc.). Chimeric targeted mice can be derived according to Hogan et al., *Manipulating the Mouse Embryo: A Laboratory Manual*, (1988); *Teratocarcinomas and Embryonic Stem Cells: A Practical Approach*, Robertson, ed., (1987); and Capecchi et al., *Science* 244:1288 (1989).

All publications and patent applications cited in this specification are herein incorporated by reference in their entireties, as if each individual publication or patent application were specifically and individually indicated to be incorporated by reference.

EXAMPLES

The following examples are provided by way of illustration only and not by way of limitation. Those of skill in the art will readily recognize a variety of noncritical parameters that could be changed or modified to yield essentially similar results.

Example 1

Design and Testing of ZFPs Targeted to the Human VEGF Gene

This first Example demonstrates the construction of ZFPs designed to recognize DNA sequences contained in the promoter of the human vascular endothelial growth factor (VEGF) gene. VEGF is an approximately 46 kDa glycoprotein that is an endothelial cell-specific mitogen induced by hypoxia. VEGF has been implicated in angiogenesis associated with cancer, various retinopathies, and other serious diseases. The DNA target site chosen was a region surrounding the transcription initiation site of the gene. The two 9 base pair (bp) sites chosen are found within the sequence agcGGGGAGGA<u>T</u>cGCGGAGGCTtgg, (SEQ ID NO:13), where the upper-case letters represent actual 9-bp targets. The protein targeting the upstream 9-bp target was denoted VEGF1, and the protein targeting the downstream 9-bp target was denoted VEGF3a. The major start site of transcription for VEGF is at the T at the 3' end of the first 9-bp target, which is underlined in the sequence above.

The human SP-1 transcription factor was used as a progenitor molecule for the construction of designed ZFPs. SP-1 has a three finger DNA-binding domain related to the well-studied murine Zif268 (Christy et al., *PNAS* 85:7857–7861 (1988)). Site-directed mutagenesis experiments using this domain have shown that the proposed "recognition rules" that operate in Zif268 can be used to adapt SP-1 to other target DNA sequences (Desjarlais & Berg, *PNAS* 91:11099–11103 (1994)). The SP-1 sequence used for construction of zinc finger clones corresponds to amino acids 533 to 624 in the SP-1 transcription factor.

The selection of amino acids in the recognition helices of the two designed ZFPs, VEGF1 and VEGF3a, is summarized in Table 1.

TABLE 1

Amino acids chosen for recognition helices of VEGF-recognizing ZFPs

| | Position: | | | | | | | | | | |
|---|---|---|---|---|---|---|---|---|---|---|---|
| | Finger 1 | | | | Finger 2 | | | | Finger 3 | | | |
| Protein | −1 | 2 | 3 | 6 | −1 | 2 | 3 | 6 | −1 | 2 | 3 | 6 |
| VEGF1 | T | S | N | R | R | S | N | R | R | D | H | R |
| VEGF3A | Q | S | D | R | R | S | N | R | R | D | E | R |

Coding sequences were constructed to express these peptides using a PCR-based assembly procedure that utilizes six overlapping oligonucleotides (FIG. 1). Three oligonucleotides (oligos 1, 3, and 5 in FIG. 1) corresponding to "universal" sequences that encode portions of the DNA-binding domain between the recognition helices. These oligonucleotides remain constant for any zinc finger construct. The other three "specific" oligonucleotides (oligos 2, 4, and 6 in FIG. 1) were designed to encode the recognition helices. These oligonucleotides contained substitutions at positions −1, 2, 3 and 6 on the recognition helices to make them specific for each of the different DNA-binding domains. Codon bias was chosen to allow expression in both mammalian cells and *E. coli*.

The PCR synthesis was carried out in two steps. First, the double stranded DNA template was created by combining the six oligonucleotides (three universal, three specific) and using a four cycle PCR reaction with a low temperature (25°) annealing step. At this temperature, the six oligonucleotides join to form a DNA "scaffold." The gaps in the scaffold were filled in by a combination of Taq and Pfu polymerases. In the second phase of construction, the zinc finger template was amplified in thirty cycles by external primers that were designed to incorporate restriction sites for cloning into pUC19. Accuracy of clones for the VEGF ZFPs were verified by DNA sequencing. The DNA sequences of each of the two constructs are listed below.

VEGF1: GGTACCCATACCTGGCAAGAAGAAG-CAGCACATCTGCCACATCCAGGGCTGT GGTAAAGTTTACGGCACAACCTCAAATCTG-CGTCGTCACCTGCGCTGGCACA CCGGC-GAGAGGCCTTTCATGTGTACCTGGTC-CTACTGTGGTAAACGCTTCACC CGTTCGT-CAAACCTGCAGCGTCACAAGCGTACCCACACC GGTGAGAAGAAAT TTGCTTGCCCGGAGTGTC-CGAAGCGCTTCATGCGTAGTGACCACCT-GTCCCGT CACATCAAGACCCACCAGAATAA-GAAGGGTGGATCC (SEQ ID NO:14).

VEGF1 translation: VPIPGKKKQHICH-IQGCGKVYGTTSNLRRHLRWHTGERPFM-CTWSYCGKRFTRS SNLQRHKRTHT-GEKKFACPECPKRFMRSDHLSRHIKTHQNKKGGS (SEQ ID NO:15).

VEGF3a: GGTACCCATACCTGGCAAGAAGAAG-CAGCACATCTGCCACATCCAGGGCTGT GGTAAAGTTTACGGCCAGTCCTCCGAC-CTGCAGCGTCACCTGCGCTGGCACA CCGGC-GAGAGGCCTTTCATGTGTACCTGGTC-CTACTGTGGTAAACGCTTCACC CGTTCGTC-AAACCTACAGAGGCACAAGCGTACACA-CACCGGTGAGAAGAAAT TTGCTTGCCCG-GAGTGTCCGAAGCGCTTCATGCGAAGT-GACGAGCTGTCACG ACATATCAAGAC-CCACCAGAACAAGAAGGGTGGATCC (SEQ ID NO:16).

VEGF3a translation: VPIPGKKKQHICH-
IQGCGKVYGQSSDLQRHLRWHTGERPFM-
CTWSYCGKRFTRS SNLQRHKRTHT-
GEKKFACPECPKRFMRSDELSRHIKTHQNKKGGS
(SEQ ID NO:17).

The ability of the designed ZFPs to bind their target sites was verified by expressing and purifying recombinant protein from *E. coli* and performing electrophoretic mobility shift assays (EMSAs). The expression of ZFPs was carried out in two different systems. In the first, the DNA-binding peptides were expressed in *E. coli* by inserting them into the commercially available pET15b vector (Novagen). This vector contains a T7 promoter sequence to drive expression of the recombinant protein. The constructs were introduced into *E. coli* BL21/DE3 (lacI$^q$) cells, which contain an IPTG-inducible T7 polymerase. Cultures were supplemented with 50 μM ZnCl$_2$, were grown at 37° C. to an OD at 600 nm of 0.5–0.6, and protein production was induced with IPTG for 2 hrs. ZFP expression was seen at very high levels, approximately 30% of total cellular protein (FIG. 2). These proteins are referred to as "unfused" ZFPs.

Partially pure unfused ZFPs were produced as follows (adapted from Desjarlais & Berg, *Proteins: Structure, Function and Genetics* 12:101–104 (1992)). A frozen cell pellet was resuspended in 1/50th volume of 1 M NaCl, 25 mM Tris HCl (pH 8.0), 100 μM ZnCl$_2$, 5 mM DTT. The samples were boiled for 10 min. and centrifuged for 10 min. at ~3,000×g. At this point the ZFP protein in the supernatant was >50% pure as estimated by staining of SDS polyacrylamide gels with Coomassie blue, and the product migrated at the predicted molecular weight of around 11 kDa (FIG. 2).

The second method of producing ZFPs was to express them as fusions to the *E. coli* Maltose Binding Protein (MBP). N-terminal MBP fusions to the ZFPs were constructed by PCR amplification of the pET15b clones and insertion into the vector pMal-c2 under the control of the Tac promoter (New England Biolabs). The fusion allows simple purification and detection of the recombinant protein. It had been reported previously that zinc finger DNA-binding proteins can be expressed from this vector in soluble form to high levels in *E. coli* and can bind efficiently to the appropriate DNA target without refolding (Liu et al. *PNAS* 94:5525–5530 (1997)). Production of MBP-fused proteins was as described by the manufacturer (New England Biolabs). Transformants were grown in LB medium supplemented with glucose and ampicillin, and were induced with IPTG for 3 hrs at 37° C. The cells were lysed by French press, then exposed to an agarose-based amylose resin, which specifically binds to the MBP moiety, thus acting as an affinity resin for this protein. The MBP fusion protein was eluted with 10 mM maltose (FIG. 2C) to release ZFP of >50% purity. In some cases, the proteins were further concentrated using a Centricon 30 filter unit (Amicon).

Partially purified unfused and MBP fusion ZFPs were tested by EMSA to assess binding to their target DNA sequences. The protein concentrations in the preparations were measured by Bradford assay (BioRad). Since SDS polyacrylamide gels demonstrated >50% homogeneity by either purification method, no adjustment was made for ZFP purity in the calculations. In addition, there could be significant amounts of inactive protein in the preparations. Therefore, the data generated by EMSAs below represent an underestimate of the true affinity of the proteins for their targets (i.e., overestimate of $K_d$s). Two separate preparations were made for each protein to help control for differences in ZFP activity.

The VEGF DNA target sites for the EMSA experiments were generated by embedding the 9-bp binding sites in 29-bp duplex oligonucleotides. The sequences of the recognition ("top") strand and their complements ("bottom") used in the assays are as follows:

VEGF site 1, top: 5'-CATGCATAGC GGGGAGGATCGCCATCGAT (SEQ ID NO:18).

VEGF site 1, bottom: 5'-ATCGATGGCGATCCTC-CCCGCTATGCATG (SEQ ID NO:19).

VEGF site 3, top: 5'-CATGCATATC GCGGAGGCTTGGCATCGAT (SEQ ID NO:20)

VEGF site 3, bottom: 5'-ATCGATGCCAAGCCTC-CGCGATATGCATG (SEQ ID NO:21).

The VEGF DNA target sites are underlined. The 3 bp on either side of the 9 bp binding site was also derived from the actual VEGF DNA sequence. The top strand of each target site was labeled with polynucleotide kinase and γ-$^{32}$P dATP. Top and bottom strands were annealed in a reaction containing each oligonucleotide at 0.5 μM, 10 mM Tris-HCl (pH 8.0), 1 mM EDTA, and 50 mM NaCl. The mix was heated to 95° C. for 5 min. and slow cooled to 30° C. over 60 min. Duplex formation was confirmed by polyacrylamide gel electrophoresis. Free label and ssDNA remaining in the target preparations did not appear to interfere with the binding reactions.

Binding of the ZFPs to target oligonucleotides was performed by titrating protein against a fixed amount of duplex substrate. Twenty microliter binding reactions contained 10 fmole (0.5 nM) 5'-$^{32}$P-labeled double-stranded target DNA, 35 mM Tris HCl (pH 7.8), 100 mM KCl, 1 mM MgCl$_2$, 1 mM dithiothreitol, 10% glycerol, 20 μg/ml poly dI-dC (optionally), 200 μg/ml bovine serum albumin, and 25 μM ZnCl$_2$. Protein was added as one fifth volume from a dilution series made in 200 mM NaCl, 20 mM Tris (pH 7.5), 1 mM DTT. Binding was allowed to proceed for 30 min. at room temperature. Polyacrylamide gel electrophoresis was carried out at 4° C. using precast 10% or 10–20% Tris-HCl gels (BioRad) and standard Tris-Glycine running buffer containing 0.1 mM ZnCl$_2$.

The results of a typical EMSA using an MBP fused ZFP are shown in FIG. 3. In this case, a 3-fold dilution series of the MBP-VEGF1 protein was used. The shifted product was quantitated on a phosphorimager (Molecular Dynamics) and the relative signal (percent of plateau value) vs. the log$_{10}$ of nM protein concentration was plotted. An apparent $K_d$ was found by determining the protein concentration that gave half maximal binding of MBP-VEGF1 to its target site, which in this experiment was approximately 2 nM.

The binding affinities determined for the VEGF proteins can be summarized as follows. VEGF1 showed the stronger DNA-binding affinity; in multiple EMSA analyses, the average apparent $K_d$ was determined to be approximately 10 nM when bound to VEGF site 1. VEGF3a bound well to its target site but with a higher apparent $K_d$ than VEGF1; the average $K_d$ for VEGF3a was about 200 nM. In both cases the MBP-fused and unfused versions of the proteins bound with similar affinities. $K_d$s were also determined under these conditions for MBP fusions of the wild-type Zif268 and SP-1 ZFPs, which yielded Kds of 60 and 65 nM, respectively. These results are similar to binding constants reported in the literature for Zif268 of approximately 2–30 nM (see, e.g., Jamieson et al., *Biochemistry* 33:5689–5695 (1994)). The $K_d$s for the synthetic VEGF ZFPs therefore compare very favorably with those determined for these naturally-occurring DNA-binding proteins.

In summary, this Example demonstrates the generation of two novel DNA-binding proteins directed to specific targets near the transcriptional start of the VEGF gene. These proteins bind with affinities similar to those of naturally-occurring transcription factors binding to their targets.

Example 2
Linking ZFPs to Bind an 18-bp Target in the Human VEGF Gene

An important consideration in ZFP design is DNA target length. For random DNA, a sequence of n nucleotides would be expected to occur once every $0.5 \times 4^n$ base-pairs. Thus, DNA-binding domains designed to recognize only 9 bp of DNA would find sites every 130,000 bp and could therefore bind to multiple locations in a complex genome (on the order of 20,000 sites in the human genome). 9-bp putative repressor-binding sequences have been chosen for VEGF in the 5' UTR where they might directly interfere with transcription. However, in case zinc finger domains that recognize 9-bp sites lack the necessary affinity or specificity when expressed inside cells, a larger domain was constructed to recognize 18 base-pairs by joining separate three-finger domains with a linker sequence to form a six-finger protein. This should ensure that the repressor specifically targets the appropriate sequence, particularly under conditions where only small amounts of the repressor are being produced. The 9-bp target sites in VEGF were chosen to be adjacent to one another so that the zinc fingers could be linked to recognize an 18-bp sequence. The linker DGGGS (SEQ. ID. NO:4) was chosen because it permits binding of ZFPs to two 9-bp sites that are separated by a one nucleotide gap, as is the case for the VEGF1 and VEGF3a sites (see also Liu et al., *PNAS* 5525–5530 (1997)).

The 6-finger VEGF3a/1 protein encoding sequence was generated as follows. VEGF3a was PCR amplified using the primers SPE7 (5'-GAGCA<u>GAATTC</u>GGCAAGAAGA-AGCAGCAC (SEQ ID NO:22)) and SPEamp12 (5'-GTGG<u>TCTAGA</u>CAGCTCGTCACTTCGC (SEQ ID NO:23)) to generate EcoRI and XbaI restriction sites at the ends (restriction sites underlined). VEGF1 was PCR amplified using the primers SPEamp13 (5'-GGAG<u>CCAAGG</u>CTGTGGTAAAGTTTACGG (SEQ ID NO:24)) and SPEamp11 (5'-GGAG<u>AAGCTT</u>GGATCCTCAT-TATCCC (SEQ ID NO:25)) to generate StyI and HindIII restriction sites at the ends (restriction sites underlined). Using synthetic oligonucleotides, the following sequence was ligated between the XbaI and StyI sites, where XbaI and StyI are underlined: <u>TCT AGA</u> CAC ATC AAA ACC CAC CAG AAC AAG AAA GAC GGC GGT GGC AGC GGC AAA AAG AAA CAG CAC ATA TGT CAC AT<u>C CAA GG</u> (SEQ ID NO:26). This introduced the linker sequence DGGGS (SEQ ID NO:4) between the two SP-1 domains. The ligation product was reamplified with primers SPE7 and SPEamp11 and cloned into pUC19 using the EcoRI and HindIII sites. The linked ZFP sequences were then amplified with primers (1) GB19 GCCATGCCGGTACCCATACCTGGCAA-GAAGAAGCAGCAC (SEQ ID NO:27)

(2) GB10 CAGATCGGATCCACCCTTCTTATTCTG-GTGGGT (SEQ ID NO:28) to introduce KpnI and BamHI sites for cloning into the modified pMAL-c2 expression vector as described above.

The nucleotide sequence of the designed, 6-finger ZFP VEGF3a/1 from KpnI to BamHI is:
GGTACCCATACCTGGCAAGAAGAAGCAG-CACATCTGCCACATCCAGGGCTGT GGTAAAGTTTA-CGGCCAGTCCTCCGACCTGCAGCGTCACCT-GCGCTGGCACA
CCGGCGAGAGGCCTTTCATGTGTACCTG-GTCCTACTGTGGTAAACGCTTCACA CGTTCGT-CAAACCTACAGAGGCACAAGCGTACACA-CACAGGTGAGAAGAAA TTTGCTTGCC-CGGAGTGTCCGAAGCGCTTCATGCGAAGTGACG-AGCTGTCTAG ACACATCAAAACCCACCAGAACAA-GAAAGACGGCGGTGGCAGCGGCAAAAA GAAA-CAGCACATATGTCACATCCAAGGCTGTG-GTAAAGTTTACGGCACAACC TCAAATCTGCGT-CGTCACCTGCGCTGGCACACCGGCGAGAGGCCTT-TCATGTG TACCTGGTCCTACTGTGGTAAACGCT-TCACCCGTTCGTCAAACCTGCAGCGTC ACAAGCG-TACCCACACCGGTGAGAAGAAATTTGCT-TGCCCGGAGTGTCCGAA GCGCTTCAT-GCGTAGTGACCACCTGTCCCGTCACATCAAG-ACCCACCAGAAT AAGAAGGGTGGATCC (SEQ ID NO:29).

The VEGF3a/1 amino acid translation (using single letter code) is:
VPIPGKKKQHICHIQGCGKVYGQSSDLQRHLRWH-TGERPFMCTWSYCGKRFTRS SNLQRHKRTHT-GEKKFACPECPKRFMRSDELSRHIKTHQNKKDG-GGSGKKKQHI CHIQGCGKVYGTTSNLRRHLRWHT-GERPFMCTWSYCGKRFTRSSNLQRHKRTH TGEKKFACPECPKRFMRSDHLSRHIKTHQNKKGGS (SEQ ID NO:30).

The 18-bp binding protein VEGF3a/1 was expressed in *E. coli* as an MBP fusion, purified by affinity chromatography, and tested in EMSA experiments as described in Example 1. The target oligonucleotides were prepared as described and comprised the following complementary sequences:

(1) JVF9 AGCGAGCGGGGAGGATCGCGGAGGCT-TGGGGCAGCCGGGTAG (SEQ ID NO:31), and (2) JVF10 CGCTCTACCCGGCTGCCCCAAGCCTC-CGCGATCCTCCCCGCT (SEQ ID NO:32).

For the EMSA studies, 20 µl binding reactions contained 10 fmole (0.5 nM) 5'-$^{32}$P-labeled double-stranded target DNA, 35 mM Tris HCl (pH 7.8), 100 mM KCl, 1 mM MgCl$_2$, 5 mM dithiothreitol, 10% glycerol, 20 µg/ml poly dI-dC, 200 µg/ml bovine serum albumin, and 25 µM ZnCl$_2$. Protein was added as one fifth volume from a 3-fold dilution series. Binding was allowed to proceed for 60 min at either room temperature or 37° C. Polyacrylamide gel electrophoresis was carried out at room temperature or 37° C. using precast 10% or 10–20% Tris-HCl gels (BioRad) and standard Tris-Glycine running buffer. The room temperature assays yielded an apparent $K_d$ for this VEGF3a/1 protein of approximately 1.5 nM. Thus, the 18-bp binding ZFP bound with high affinity to its target site. In a parallel experiment, VEGF1 protein was tested against its target using the oligonucleotides described in Example 1, yielding an apparent $K_d$ of approximately 2.5 nM. When binding and electrophoresis were performed at 37° C., the apparent $K_d$ of VEGF3a/1 was approximately 9 nM when tested against the 18-bp target, compared to a $K_d$ of 40 nM for VEGF1 tested against its target. This indicates that the difference in binding affinities is accentuated at the higher temperature.

The apparent $K_d$ is a useful measure of the affinity of a protein for its DNA target. However, for a DNA binding site either in vitro or in vivo, its occupancy is determined to a large extent by the off-rate of the DNA-binding protein. This parameter can be measured by competition experiments as shown in FIG. 4. The conditions for EMSA were as described above; binding and electrophoresis were performed at 37° C. These data indicate that the half-life of the protein-DNA complex is more than ten times longer for VEGF3a/1 than for VEGF1. Thus, under these in vitro conditions, the occupancy of the target site is much higher for the 18-bp binding protein than for the 9-bp binding protein.

Example 3
Fusing Designed ZFP Sequences to Functional Domains in Mammalian Expression Vectors This Example describes the development of expression vectors for producing ZFPs within mammalian cells, translocating them to the nucleus, and providing functional domains that are localized to the target DNA sequence by the ZFP. The functional domains employed are the Kruppel-Associated Box (KRAB) repression domain and the Herpes Simplex Virus (HSV-1) VP16 activation domain.

Certain DNA-binding proteins contain separable domains that function as transcriptional repressors. Approximately 20% of ZFPs contain a non-DNA-binding domain of about 90 amino acids that functions as a transcriptional repressor (Thiesen, The New Biologist 2:363–374 (1990); Margolin et al., *PNAS* 91:4509–4513 (1994); Pengue et al., (1994), supra; Witzgall et al., (1994), supra). This domain, termed the KRAB domain, is modular and can be joined to other DNA-binding proteins to block expression of genes containing the target DNA sequence (Margolin et al., (1994); Pengue et al., (1994); Witzgall et al., (1994), supra). The KRAB domain has no effect by itself; it needs to be tethered to a DNA sequence via a DNA-binding protein to function as a repressor. The KRAB domain has been shown to block transcription initiation and can function at a distance of up to at least 3 kb from the transcription start site. The KRAB domain from the human KOX-1 protein (Thiesen, The New Biologist 2:363–37 (1990)) was used for the studies described here. This 64 amino acid domain can be fused to ZFPs and has been shown to confer repression in cell culture (Liu et al., supra).

The VP16 protein of HSV-1 has been studied extensively, and it has been shown that the C-terminal 78 amino acids can act as a trans-activation domain when fused to a DNA-binding domain (Hagmann et al., *J. Virology* 71:5952–5962 (1997)). VP16 has also been shown to function at a distance and in an orientation-independent manner. For these studies, amino acids 413 to 490 in the VP16 protein sequence were used. DNA encoding this domain was PCR amplified from plasmid pMSVP16ΔC+119 using primers with the following sequences:

(1) JVF24 CGCGGATCCGCCCCCCCGACCGATG (SEQ ID NO:33), and
(2) JVF25 CCGCAAGCTTACTTGTCATCGTCGTCCT-TGTAGTCGCTGCCCCCACCGTACTC GTCAAT-TCC (SEQ ID NO:34).

The downstream primer, JVF25, was designed to include a downstream FLAG epitope-encoding sequence.

Three expression vectors were constructed for these studies. The general design is summarized in FIG. 5. The vectors are derived from pcDNA3.1(+) (Invitrogen), and place the ZFP constructs under the control of the cytomegalovirus (CMV) promoter. The vector carries ampicillin and neomycin markers for selection in bacteria and mammalian cell culture, respectively. A Kozak sequence for proper translation initiation (Kozak, *J. Biol. Chem.* 266:19867–19870 (1991)) was incorporated. To achieve nuclear localization of the products, the nuclear localization sequence (NLS) from the SV40 large T antigen (Pro-Lys-Lys-Lys-Arg-Lys-Val) (Kalderon et al., *Cell* 39:499–509 (1984)) was added. The insertion site for the ZFP-encoding sequence is followed by the functional domain sequence. The three versions of this vector differ in the functional domain; "pcDNA-NKF" carries the KRAB repression domain sequence, "pcDNA-NVF" carries the VP16 activation domain, and "NF-control" carries no functional domain. Following the functional domain is the FLAG epitope sequence (Kodak) to allow specific detection of the ZFPs.

The vectors were constructed as follows. Plasmid pcDNA-ΔHB was constructed by digesting plasmid pcDNA3.1(+) (Invitrogen) with HindIII and BamHI, filling in the sticky ends with Klenow, and religating. This eliminated the HindIII, KpnI, and BamHI sites in the polylinker. The vector pcDNA3.1(+) is described in the Invitrogen catalog. Plasmid pcDNA-NKF was generated by inserting a fragment into the EcoRI/XhoI sites of pcDNA-ΔHB that contained the following: 1) a segment from EcoRI to KpnI containing the Kozak sequence including the initiation codon and the SV40 NLS sequence, altogether comprising the DNA sequence
<u>GAATTC</u>GCTAGCGCCACCATGGCCCCCAAGAAGAA-GAGGAAGGTGGGAATC CATGG<u>GGTAC</u> (SEQ ID NO:36),
where the EcoRI and KpnI sites are underlined; and 2) a segment from KpnI to XhoI containing a BamHI site, the KRAB-A box from KOX1 (amino acid coordinates 11–53 in Thiesen, 1990, supra), the FLAG epitope (from Kodak/IBI catalog), and a HindIII site, altogether comprising the sequence.
<u>GGTAC</u>CCGGG<u>GATCC</u>CGGACACTGGTGACCTTC A-AGGATGTATTTGTGGACT TCACCAGGGAGGA-GTGGAA GCTGCTGGACACTGCTCAGCAGATCGTG-TACAG AAATGTGATGCTGGAGAACTATAAGAAC-CTGGTTTCCTTGGGCAGCGACTAC AAGGACGAC-GATGACAAGTAAGCTT<u>CTCGAG</u> (SEQ ID NO:37).
where the KpnI, BamHI and XhoI sites are underlined.

The VEGF3a/1-KRAB effector plasmid was generated by inserting a KpnI-BamHI cassette containing the ZFP sequences into pcDNA-NKF digested with KpnI and BamHI. The VEGF1-KRAB and VEGF3a-KRAB effector plasmids were constructed in a similar way except that the ZFP sequences were first cloned into the NLS-KRAB-FLAG sequences in the context of plasmid pLitmus 28 (New England Biolabs) and subsequently moved to the BamHI-XhoI sites of pcDNA3.1(+) as a BglII-XhoI cassette, where the BglII site was placed immediately upstream of the EcoRI site (see Example 4 for expression of these vectors).

The effector plasmids used in Example 5 were constructed as follows. Plasmid pcDNA-NVF was constructed by PCR amplifying the VP16 transactivation domain, as described above, and inserting the product into the BamHI/HindIII sites of pcDNA-NKF, replacing the KRAB sequence. The sequence of the inserted fragment, from BamHI to HindIII, was:
<u>GGATCC</u>GCCCCCCCGACCGATGTCAGCCTGGGGGA-CGAGCTCCACTTAGACG GCGAGGACGTGGCGATG-GCGCATGCCGACGCGCTAGACGATTTCGATCTGGA CATGTTGGGGGACGGGGATTCCCCGGGGCC-GGGATTTACCCCCCACGACTCC GCCCCC- TACG-GCG CTCTGGATATGGCCGACTTCGAGTTTGAG-CAGATGTTTAC CGATGCCCTTGGAATTGACGAG-TACGGTGGGGGCAGCGACTACAAGGACGAC GAT-GACAAGT<u>AAGCTT</u> (SEQ ID NO:38).

VEGF1-VP16 and VEGF3a/1-VP16 vectors were constructed by inserting a KpnI-BamHI cassette containing the ZFP sequences into pcDNA-NVF digested with KpnI and BamHI.

The effector plasmids used in Example 6 were constructed as follows. Plasmid NF-control was generated by inserting the sequence.
GAATTCGCTAGCGCCACCATGGCCCCCAAGAAGAA-GAGGAAGGTGGGAATCC ATGGGGTACCCGGGGAT-GGATCCGGCAGCGACTACAAGGACGACGATGACA AGTAAGCTTCTCGAG (SEQ ID NO:39).
into the EcoRI-XhoI sites of pcDNA-NKF, thereby replacing the NLS-KRAB-FLAG sequences with NLS-FLAG only.

VEGF1-NF and VEGF3a/1-NF were constructed by inserting a KpnI-BamHI cassette containing the ZFP sequences into NF-control digested with KpnI and BamHI. CCR5-KRAB was constructed in the same way as the VEGF KRAB vectors, except that the ZFP sequences were designed to be specific for a DNA target site that is unrelated to the VEGF targets.

Finally, control versions of both the KRAB and VP16 expression plasmids were constructed. Plasmid NKF-control was designed to express NLS-KRAB-FLAG without zinc finger protein sequences; plasmid NVF-control was designed to express NLS-VP16-FLAG without ZFP sequences. These plasmids were made by digesting pcDNA-NKF and -NVF, respectively, with BamHI, filling in the ends with Klenow, and religating in order to place the downstream domains into the proper reading frame. These plasmids serve as rigorous controls for cell culture studies.

Mammalian cell expression and nuclear localization of the VEGF engineered ZFPs was demonstrated through immunofluorescence studies. 293 (human embryonic kidney) cells were transfected with the expression plasmid encoding the NLS-VEGF1-KRAB-FLAG chimera. Lipofectamine was used as described below. After 24–48 hours, cells were fixed and exposed to a primary antibody against the FLAG epitope. A secondary antibody labeled with Texas Red was applied, and the cells were counter stained with DAPI. Texas Red staining was observed to consistently co-localize with the DAPI staining, indicating that the ZFP being expressed from this plasmid was nuclear localized.

Example 4
Repression of VEGF Reporters in Co-transfection Experiments

This Example demonstrates the use of transient co-transfection studies to measure the activity of the ZFP repressor proteins in cells. Such experiments involve co-transfection of ZFP-KRAB expression ("effector") plasmids with reporter plasmids carrying the VEGF target sites. Efficacy is assessed by the repression of reporter gene expression in the presence of the effector plasmid relative to empty vector controls.

The reporter plasmid system was based on the pGL3 firefly luciferase vectors (Promega). Four copies of the VEGF target sites were inserted upstream of the SV40 promoter, which is driving the firefly luciferase gene, in the plasmid pGL3-Control to create pVFR1–4x. This plasmid contains the SV40 enhancer and expresses firefly luciferase to high levels in many cell types. Insertions were made by ligating together tandem copies of the two complementary 42-bp oligonucleotides, JVF9 and JVF10, described in Example 2. Adaptor sequences were ligated on, and the assembly was inserted into the MluI/BglII sites of pGL3-Control. This resulted in the insertion of the following sequence between those sites:
ACGCGTaagcttGCTAGCGAGCGGGGAGGATC GCGGAGGCTTGGGGCAGCCGGG TAGAGC GAGCGGGGAGGATCGCGGAGGCTTGGGGCAGCCG GGTAGAGCGAG CGGGGAGGATCGCGGAGGCT TGGGGCAGCCGGGTAGAGCGAGCGGGGAGGATC GCGGAGGCTTGGGGCAGCCGGGTAGAGCGCTCAG-aagcttAGATCT (SEQ ID NO:40).

The first six and last six nucleotides shown are the MluI and BglII sites; the lowercase letters indicate HindIII sites. The binding sites for VEGF1 and VEGF3a are underlined.

The effector plasmid construction is described above. The VEGF1-KRAB, VEGF3a-KRAB, and VEGF3a/1-KRAB expression vectors were designed to produce a fusion of the SV40 nuclear localization sequence, the VEGF ZFP, the KRAB repression domain, and a FLAG epitope marker all under the control of the CMV promoter. The empty pcDNA3.1 expression vector was used as a control (pcDNA).

All vectors were prepared using Qiagen DNA purification kits. FIG. 6 shows a typical set of transfections using COS-1 (African green monkey kidney) cells. Approximately 40,000 cells were seeded into each well of a 24-well plate and allowed to grow overnight in Dulbecco's Modified Eagle Medium (D-MEM) medium containing 10% fetal bovine serum at 37° C. with 5% $CO_2$. Cells were washed with PBS and overlayed with 200 µl of serum-free D-MEM. Plasmids were introduced using lipofectamine (Gibco-BRL). Each well was transfected with about 0.3 µg of effector plasmid, 0.3 µg of reporter plasmid, and 0.01 µg of plasmid pRL-SV40 (Promega) that had been complexed with 6 µl of lipofectamine and 25 µl of D-MEM for 30 min at 37° C. Transfections were done in triplicate. After 3 hrs, 1 ml of medium containing 10% serum was added to each well. Cells were harvested 40–48 hours after transfection. Luciferase assays were done using the Dual Luciferase™ System (Promega). The third plasmid transfected, pRL-SV40, carries the Renilla luciferase gene and was co-transfected as a standard for transfection efficiency. The data shown in FIG. 6 are the averages of triplicate assays normalized against the Renilla activity.

For the control reporter plasmid pGL3-Control (pGL3-C), the presence or absence of the ZFP-KRAB expression plasmid does not influence the luciferase expression level. However, for pVFR1-4x, the reporter containing four copies of the VEGF target site, presence of the VEGF1 (9-bp-binding ZFP) or VEGF3a/1 (18-bp-binding ZFP) expression plasmid reduces luciferase expression by a factor of 2–3 relative to the empty pcDNA vector control. The VEGF3a (9-bp-binding ZFP) expression plasmid appears to exhibit little or no effect. These experiments clearly demonstrate that a designed ZFP is capable of functioning in a cell to repress transcription of a gene when its target site is present. Furthermore, it appears that a certain level of affinity is required for function; i.e., VEGF1 and VEGF3a/1, with Kds of 10 nM or less, are functional, whereas VEGF3a, with a $K_d$ of 200 nM, is not.

A second reporter plasmid, pVFR2-4x, was constructed by removing the four copies of the VEGF target sites using HindIII and inserted them into the HindIII site of pGL3-Control (in the forward orientation). This places the target sites between the start site of transcription for the SV40 promoter and the translational start codon of the luciferase gene. In similar co-transfection experiments to those described, approximately 3–4 fold repression of the luciferase signal was observed with the VEGF1-KRAB or VEGF3a/1-KRAB repressors relative to the pcDNA controls (data not shown). This indicates that the repressors are active when bound either upstream or downstream of the start of transcription.

Example 5
Activation of VEGF Reporters in Co-Transfection Experiments

This Example demonstrates the use of transient co-transfection studies to measure the activity of the ZFP transcriptional activators in cells. The experimental setup is similar to that of Example 4 except that a different transfection method, a different cell line, and a different set of reporter and effector plasmids was used.

For activation experiments, a reporter was constructed labeled pVFR3-4x. This reporter contains the four copies of the VEGF targets, with the sequence shown above, at the MluI/BglII sites of plasmid pGL3-Promoter (Promega). This vector has been deleted for the SV40 enhancer sequence and therefore has a lower basal level of firefly luciferase expression. pVFR3-4x was constructed by swapping the KpnI/NcoI fragment of pVFR1–4x into the KpnI/NcoI sites of pGL3-Promoter.

The effector plasmid construction is described above. The VEGF1-VP16, VEGF3a-VP16, and VEGF3a/1-VP16 expression vectors were designed to produce a fusion of the SV40 nuclear localization sequence, the VEGF ZFP, the VP16 trans-activation domain, and a FLAG epitope tag all under the control of the CMV promoter. The empty pcDNA3 expression vector was used as a control.

All vectors were prepared using Qiagen DNA purification kits. FIG. 7 shows a typical set of transfections using 293 (human embryonic kidney) cells. Approximately 40,000 cells were seeded into each well of a 24-well plate and allowed to grow overnight in D-MEM medium containing 10% fetal bovine serum at 37° C. with 5% $CO_2$. Cells were washed with serum-free D-MEM and overlayed with 200 µl of the same. Plasmids were introduced using a calcium phosphate transfection kit (Gibco-BRL) according to the manufacturer's instructions. Cells in each well were transfected with 1.5 µg of reporter plasmid, 1.5 µg of effector plasmid, and 0.5 µg of an actin/β-gal plasmid. Plasmids were combined with 15 µl of $CaCl_2$ and brought to 100 µl with $dH_2O$. 100 µl of HEPES solution was added dropwise while vortexing. The mix was incubated for 30 min at room temperature. The 200 µl of calcium phosphate-treated DNA was then added to the medium in each well. Transfections were done in triplicate. After 5 hours, the medium was removed and 1 ml of medium containing 10% serum was added. Cells were harvested 40–48 hours after transfection. Luciferase assays were done using the Dual-Light™ system (Tropix). The third plasmid transfected, actin/β-gal, carries the β-galactosidase gene under the control of the actin promoter and was co-transfected as a standard for transfection efficiency. The β-galactosidase assays were also done according to the manufacturer's protocol (Tropix). The data shown in FIG. 7 are the average of triplicate assays normalized against the β-galactosidase activity.

For the control reporter plasmid, pGL3-Promoter (pGL3-P), the presence or absence of the ZFP-VP16 expression plasmid does not significantly influence the luciferase expression level. For pVFR3-4x, the reporter containing four copies of the VEGF target site, presence of VEGF1 (the 9-bp-binding ZFP) shows a very slight activation relative to the empty pcDNA vector control. VEGF3 a/1 (the 18-bp-binding ZFP) expression plasmid activates luciferase expression very substantially, showing about a 14-fold increase relative to pcDNA. These experiments clearly demonstrate that a designed ZFP, when fused to the VP16 activation domain, is capable of functioning in a cell to activate transcription of a gene when its target site is present. Furthermore, these results clearly demonstrate that an 18-bp binding protein, VEGF3a/1, is a much better activator in this assay than a 9-bp binding VEGF1 protein. This could be a result of the improved affinity or decreased off-rate of the VEGF3a/1 protein.

A fourth VEGF reporter plasmid was constructed by cloning the KpnI/NcoI fragment of pVFR2-4x into pGL3-Promoter to create plasmid pVFR4-4x. Activation was observed in co-transfections using this reporter in combination with effector plasmids expressing the VEGF1-VP16 and VEGF3a/1-VP16 fusions (data not shown). This indicates that these artificial trans-activators are functional when bound either upstream or downstream of the start of transcription.

These co-transfection data demonstrate that ZFPs can be used to regulate expression of reporter genes. Such experiments serve as a useful tool for identifying ZFPs for further use as modulators of expression of endogenous cellular genes. As is shown below, modulation results can vary between co-transfection experiments and endogenous gene experiments, while using the same ZFP construct.

Example 6
Repression of an Endogenous VEGF Gene in Human Cells

This Example demonstrates that a designed ZFP can repress expression of an endogenous cellular gene that is in its natural context and chromatin structure. Specifically, effector plasmids expressing VEGF ZFPs fused to the KRAB repression domain were introduced into cells and were shown to down-regulate the VEGF gene.

Eucaryotic expression vectors were constructed that fuse the VEGF3a/1 and the VEGF1 ZFPs to the SV40 NLS and KRAB, as described above in Example 3. Transfections were done using Lipofectamine, a commercially available liposome preparation from GIBCO-BRL. All plasmid DNAs were prepared using Qiagen Midi DNA purification system. 10 µg of the effector plasmid was mixed with 100 µg of Lipofectamine (50 µl) in a total volume of 1600 µl of Opti-MEM. A pCMVβ-gal plasmid (Promega) was also included in the DNA mixture as an internal control for transfection efficiency. Following a 30 minute incubation, 6.4 ml of DMEM was added and the mixture was layered on $3 \times 10^6$ 293 cells. After five hours, the DNA-Lipofectamine mixture was removed, and fresh culture medium containing 10% fetal bovine serum was layered on the cells.

Eighteen hours post transfection, the 293 cells were induced by treatment with 100 µM DFX (desferrioxamine), resulting in a rapid and lasting transcriptional activation of the VEGF gene and also in a gradual increase in VEGF mRNA stability (Ikeda et al., *J. Biol. Chem.* 270:19761–19766 (1995)). Under routine culture conditions, 293 cells secrete a low level of VEGF in the culture media. The cells were allowed to incubate an additional 24 hours before the supernatants were collected for determination of VEGF levels by an ELISA assay.

In parallel experiments that demonstrated a similar level of repression, cell viability was monitored using the Promega Celltiter 96® Aqueous One Solution cell proliferation assay (Promega). After Dfx treatment for 18 hours, 500 µL of the original 2 ml of media was removed and analyzed for VEGF expression, as described above. To evaluation cell viability, 300 µL of Promega Celltiter 96® Aqueous One Solution Reagent was added to the remaining 1.5 ml. The cells were then incubated at 37° C. for approximately 2 hours. 100 µL from each well was transferred to a 96-well plate and read on an ELISA plate reader at OD 490 nm. There was no significant reduction in viability of cells expressing the VEGF3a/1-KRAB construct relative to those transfected with empty vector controls, indicating that the VEGF repression observed was not due to generalized cell death.

A 40–50-fold decrease in VEGF expression was noted in the DFX treated cells transfected with VEGF3a/1-KRAB, an expression vector encoding the 18 bp binding VEGF high affinity ZFP. A two-fold decrease in expression was observed when cells were transfected with VEGF1-KRAB, an expression vector encoding the 9 bp binding VEGF high affinity ZFP. No significant decrease in VEGF expression was observed in cells that were transfected with a non-VEGF ZFP (CCR5-KRAB) or NKF-control (FIG. 8). Similar results have been obtained in three independent transfection experiments.

In a separate experiment, the following results were obtained (data not shown). VEGF1-NF, which expresses the 9-bp-binding VEGF1 ZFP without a functional domain, showed no effect on VEGF gene expression. A significant reduction in VEGF expression was observed with VEGF3a/1-NF, which expresses the 18-bp binding protein without a functional domain. This result suggests that binding to the start site of transcription, even without a repression domain, interferes with transcription. Even when fused to the KRAB domain, the VEGF3a ZFP is unable to affect expression levels (plasmid VEGF3a-KRAB). However, VEGF1 fused to KRAB (VEGF1-KRAB) results in a dramatic decrease in expression. VEGF3a/1 fused to KRAB (VEGF3a/1-KRAB) prevents expression of VEGF altogether.

These data indicate that a designed ZFP is capable of locating and binding to its target site on the chromosome and preventing expression of an endogenous cellular target gene. In particular, the results indicate that ZFPs with a $K_d$ of less than about 25 nM (e.g., VEGF1 has an average apparent $K_d$ of about 10 nM) provide dramatic decreases in expression. In addition, the data demonstrate that the KRAB functional domain enhances gene silencing. Because in this experiment the introduction of the repressor occurs before the inducer of VEGF is added (DFX), the data demonstrate the ability of a designed repressor to prevent activation of an already quiescent gene. In addition, these results demonstrate that a six-finger engineered ZFP (VEGF3a/1) with nanomolar affinity for its target is able to inhibit the hypoxic response of the VEGF gene when it binds a target that overlaps the transcriptional start site.

Example 7

Activation of Andogenous VEGF Gene in Human Cells

This Example demonstrates that a designed ZFP can activate the expression of a gene that is in its natural context and chromatin structure. Specifically, effector plasmids expressing VEGF ZFPs fused to the VP16 activation domain were introduced into cells and were shown to up-regulate the VEGF gene.

Eucaryotic expression vectors were constructed that fuse the VEGF3a/1 and the VEGF1 ZFPs to the SV40 NLS and VP16, as described in Example 3. Transfections were done using Lipofectamine, a commercially available liposome preparation from GIBCO-BRL. All plasmid DNAs were prepared using the Qiagen Midi DNA purification system. 10 μg of the effector plasmid (containing the engineered ZFP) was mixed with 100 μg of Lipofectamine (50 μl) in a total volume of 1600 μl of Opti-MEM. A pCMVβ-gal plasmid (Promega) was also included in the DNA mixture as an internal control for transfection efficiency. Following a 30 minute incubation, 6.4 ml of DMEM was added and the mixture was layered on $3\times10^6$ 293 cells. After five hours, the DNA-Lipofectamine mixture was removed, and fresh culture medium containing 10% fetal bovine serum was layered on the cells. One day later, fresh media was added and the supernatant was collected 24 hours later for determination of VEGF levels using a commercially available ELISA kit (R and D Systems).

For the three-fingered VEGF1-specific ZFP (VEGF1-VP16), a 7–10 fold increase in VEGF expression was observed when compared to control plasmid (NVF-control) and mock transfected cells (FIG. 9). Similar results have been obtained in 5 independent experiments. It is important to note that the level of VEGF secretion in VEGF1-VP16 transfected cells was equivalent or greater than the level in cells that have been treated with DFX (FIG. 9). Introduction of VEGF3a/1-VP16 stimulated a more modest induction of VEGF. This result is consistent with the finding in Example 6, in which expression of the 18-bp binding protein without a functional domain prevented activation to a certain degree. This result suggested that the tight binding of this protein to the start site of transcription interferes with activation.

These data indicate that a designed ZFP is capable of locating and binding to its target site on the chromosome, presenting a transcriptional activation domain, and dramatically enhancing the expression level of that gene. In particular, the results indicate that ZFPs with a $K_d$ of less than about 25 nM (e.g., VEGF1 has an average apparent $K_d$ of about 10 nM) provide dramatic increases in expression.

Example 8

RNase Protection Assay

To further substantiate the results in Examples 6 and 7, a ribonuclease protection assay (RPA) was performed to correlate the increased level of VEGF protein with an increase in VEGF mRNA levels (Example 7), and to correlate the decreased level of VEGF protein with a decrease in VEGF mRNA levels (Example 6).

RNA was isolated from the transfected cells using an RNA isolation kit (Pharmingen). Radiolabeled multi template probes, which included a VEGF specific probe, were prepared by in vitro transcription and hybridized overnight at 56° C. to 5 μg of each of the RNAs from the experimental and control transfected cells. The hybridization mixture was treated with RNase and the protected probes were purified and subjected to 5% denaturing polyacrylamide gel electrophoresis and the radioactivity was evaluated by autoradiography. 293 cells transfected with the VEGF1-VP16 had a 2–4 fold increase in the level of VEGF mRNA when compared to cells transfected with NVF-control (FIG. 10, panel A; see Example 7 for experimental details). The size of the protected probe was identical to the size of the probe generated from the control human RNA provided as a control for RNA integrity. (FIG. 10, panel A).

In a separate experiment, the level of VEGF specific mRNA was also quantitated in cells that had been transfected with a VEGF-KRAB effector plasmid (FIG. 10, panel B; see Example 6 for experimental details). The details of the transfection are described in Example 6. A dramatic decrease in the level of VEGF mRNA was observed when cells were transfected with the VEGF3a/1-KRAB effector plasmid. No significant decrease in VEGF mRNA was observed when cells were transfected with NKF-control or a non-VEGF specific ZFP (CCR5-5-KRAB and CCR5-3-KRAB, which recognize different CCR5 target sites).

This experiment demonstrates that the increase in VEGF protein observed upon transfection with the VEGF1-VP16 chimeric transcription factor is mediated by an increase in the level of VEGF mRNA. Similarly, the decrease in VEGF protein observed upon transfection with the VEGF3 a/1-KRAB chimeric transcription factor is mediated by a decrease in the level of VEGF mRNA.

Example 9
Repression of Human VEGF-A Gene Expression Using Fusions Between a v-erbA Repression Domain and a Zinc Finger DNA-Binding Domain Construction of ZFP Fusions The following zinc finger DNA binding domains were used for the construction of fusion proteins that bind to the human VEGF-A gene. The VEGF3a/1 domain comprises six zinc fingers and binds to a sequence overlapping the VEGF-A transcription startsite. See co-owned PCT WO 00/41566 and PCT WO 00/42219. The VOP28A binding domain comprises three zinc fingers and binds to a sequence approximately 573 nucleotides upstream of the transcription startsite. The VOP30A binding domain comprises three zinc fingers and binds to two sequences in the VEGF-A gene: one approximately 42 nucleotides downstream of the transcription startsite and one approximately 530 nucleotides downstream of the transcription startsite. The VOP32B binding domain comprises three zinc fingers and binds to a sequence approximately 434 nucleotides downstream of the transcription startsite. The design, sequence and binding properties of these binding domains has been disclosed by Liu et al. (2001) *J. Biol. Chem.* 276:11,323–11,334; wherein they were designated VZ–573, VZ+42/+530 and VZ+434b, respectively.

Fusion proteins were designed, which comprise amino acids 223–556 of v-erbA (wherein amino acid 556 is the carboxy-terminal amino acid of the v-erbA protein) in operative linkage with each of the aforementioned zinc finger binding domains. The fusion proteins were also designed to contain a nuclear localization sequence and a FLAG epitope tag. Design and preparation of nucleic acids encoding these fusion proteins, and their insertion into vectors, was accomplished essentially as described supra in Examples 1 and 3, and in co-owned WO 00/42219. See also Zhang et al. (2000) *J. Biol. Chem.* 275:33,850–33,860 and Liu et al. (2001) supra.

Assays for the Activity of ZFP Fusions on the Endogenous VEGF-A Gene in Human Cells by Transient Transfection.

Human embryonic kidney cells (HEK 293) were grown in DMEM (Dulbecco's modified Eagle's medium), supplemented with 10% fetal bovine serum, in a 5% $CO_2$ incubator at 37° C. Cells were plated in 24-well plates at a density of 160,000 cells per well. A day later, when cells were between 50% and 90% confluent, plasmids encoding ZFP/v-erbA fusions were transfected into the cells, using 1.5 μl LipofectAMINE reagent (according to manufacture's recommendations: Gibco Life Technologies, Rockville, Md.) and various amounts of DNA, as indicated in FIG. 11. Medium was removed and replaced with fresh medium 16 hours after transfection. Forty hours after transfection, the culture medium and the cells were harvested and assayed for VEGF-A expression. VEGF-A protein content in the culture medium was assayed using a human VEGF ELISA kit (R&D Systems, Minneapolis, Minn.) according to manufacture's protocol.

The results, shown in FIG. 11, indicate that v-erbA/ZFP fusions are effective in repressing expression of the human VEGF-A gene.

Figure 12:
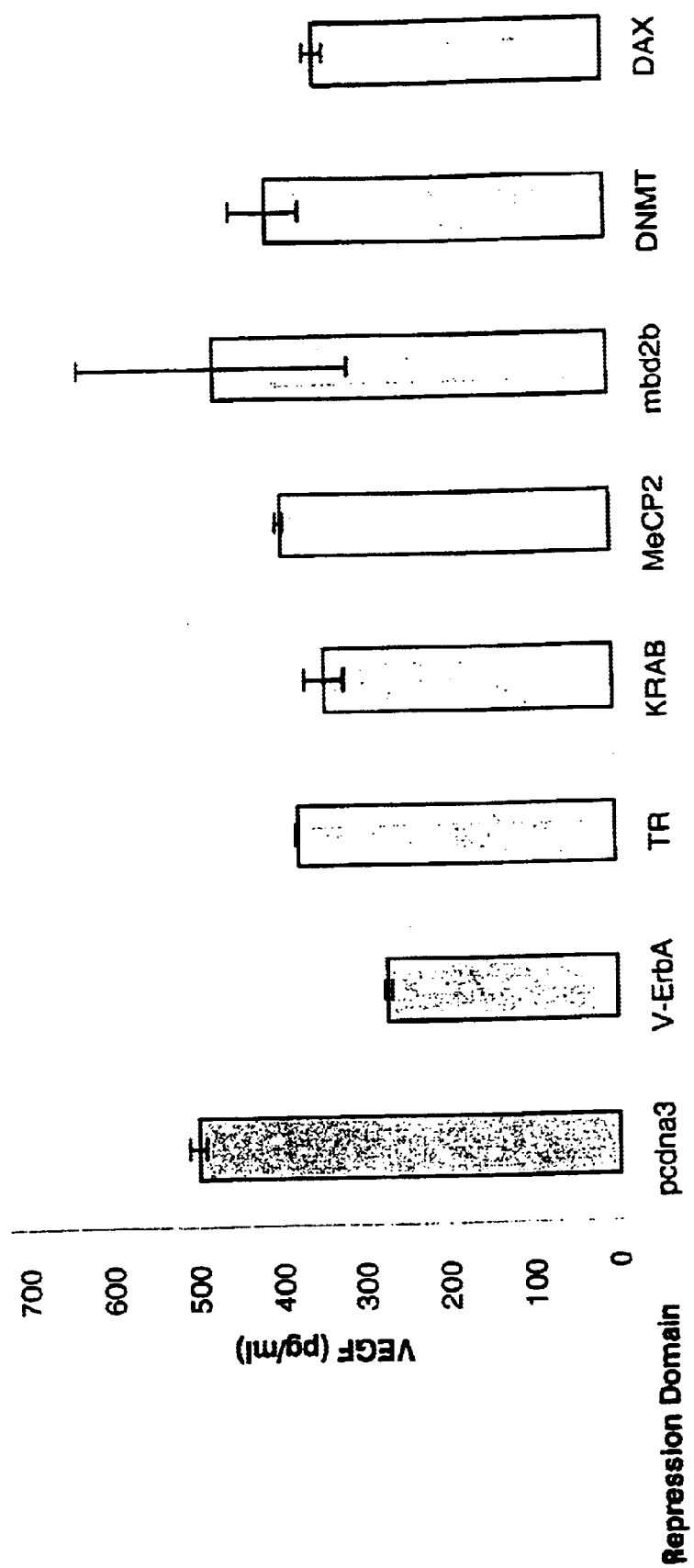
FIG. 12. Levels of VEGF-A protein in the culture medium of human 293 cells that had been transfected with plasmids encoding different repression domains fused to the VOP32B ZFP binding domain (see Example 9). The name of the repression domain tested in each transfection is given along the abscissa.

Example 10
Repression of Human VEGF-A Gene Expression: Repression Domain Survey The activity of a number of different repression domains, fused to the VOP32B binding domain (described in Example 9, supra), was tested. Vectors were constructed, essentially as described in Example 9 supra, to encode fusion proteins comprising a nuclear localization sequence, a repression domain, the VOP 32B binding domain and a FLAG epitope tag. The repression domains tested included KRAB, v-erbA, TR (in the absence of ligand), MeCP2, MBD2B, DNMT and Dax. HEK 293 cells were cultured and transfected, and VEGF-A protein levels were measured in the culture medium of transfected cells, as described in Example 9 supra. Results are shown in FIG. 12, and indicate that all of the repression domains tested were able to repress VEGF-A expression to different extents.

Figure 13:
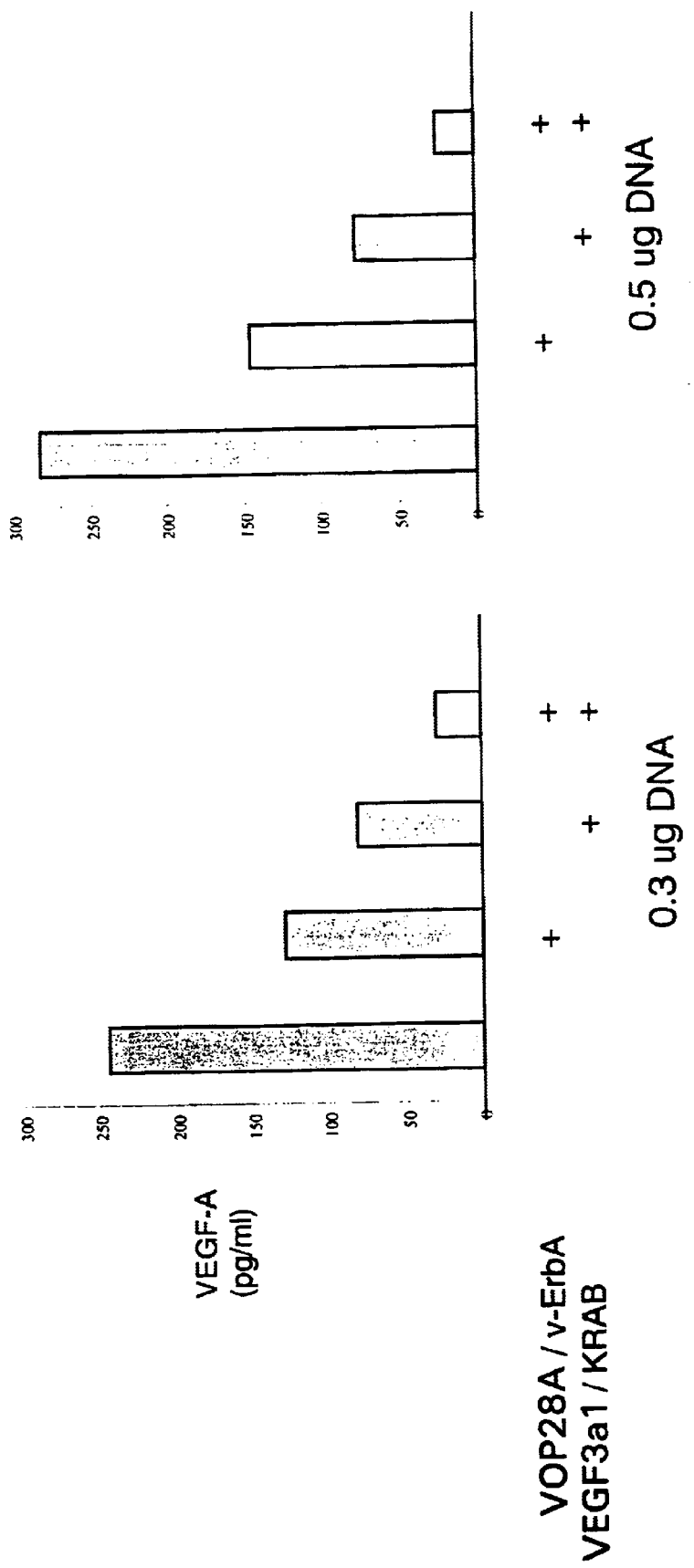
FIG. 13. Levels of VEGF-A protein in the culture medium of human 293 cells that had been transfected with plasmids encoding different repression domains targeted to different regions of the gene. Transfection of cells with plasmids encoding a VOP28A/v-erbA fusion, a VEGF3a1/KRAB fusion, neither, or both is as indicated below the abscissa. Two different concentrations of ZFP-encoding DNA were tested, as indicated.

Example 11
Enhanced Repression of Human VEGF-A Gene Using Combinations of Functional Domains This example provides evidence that enhanced repression of gene expression is obtained through the use of several repression domains, each targeted to a different region of a gene. Human 293 cells were transfected with a plasmid encoding the v-erbA repression domain fused to the VOP28A binding domain, or with a plasmid encoding the KRAB repression domain fused to the VEGF3a/1 binding domain, or with both plasmids, and VEGF-A expression was measured in transfected cells. Plasmid constructions, cell culture, transfection and measurement of VEGF-A were as described in Example 9. The results, shown in FIG. 13, show approximately two-fold repression of VEGF-A expression by v-erbA, approximately three-fold repression by KRAB, and a synergistic repression of approximately ten-fold when both repression domains are present in the cell.

Example 12
Repression of Mouse VEGF-A Gene Expression Using Fusions Between a v-erbA Repression Domain and a Zinc Finger DNA-Binding Domain Because of homology between the human and mouse VEGF-A genes, several of the zinc finger binding domains described in Example 9 also bind to analogous sites in the mouse VEGF-A gene. In particular the VOP 28A, VOP 30A and VOP 32B binding domains bind to sites located at approximately 500 nucleotides upstream, 530 nucleotides downstream, and 430 nucleotides downstream, respectively, of the mouse VEGF-A transcription startsite. Accordingly, the ZFP/v-erbA fusions described in Example 9 were tested for their ability to repress expression of the mouse VEGF-A gene.

Figure 14:
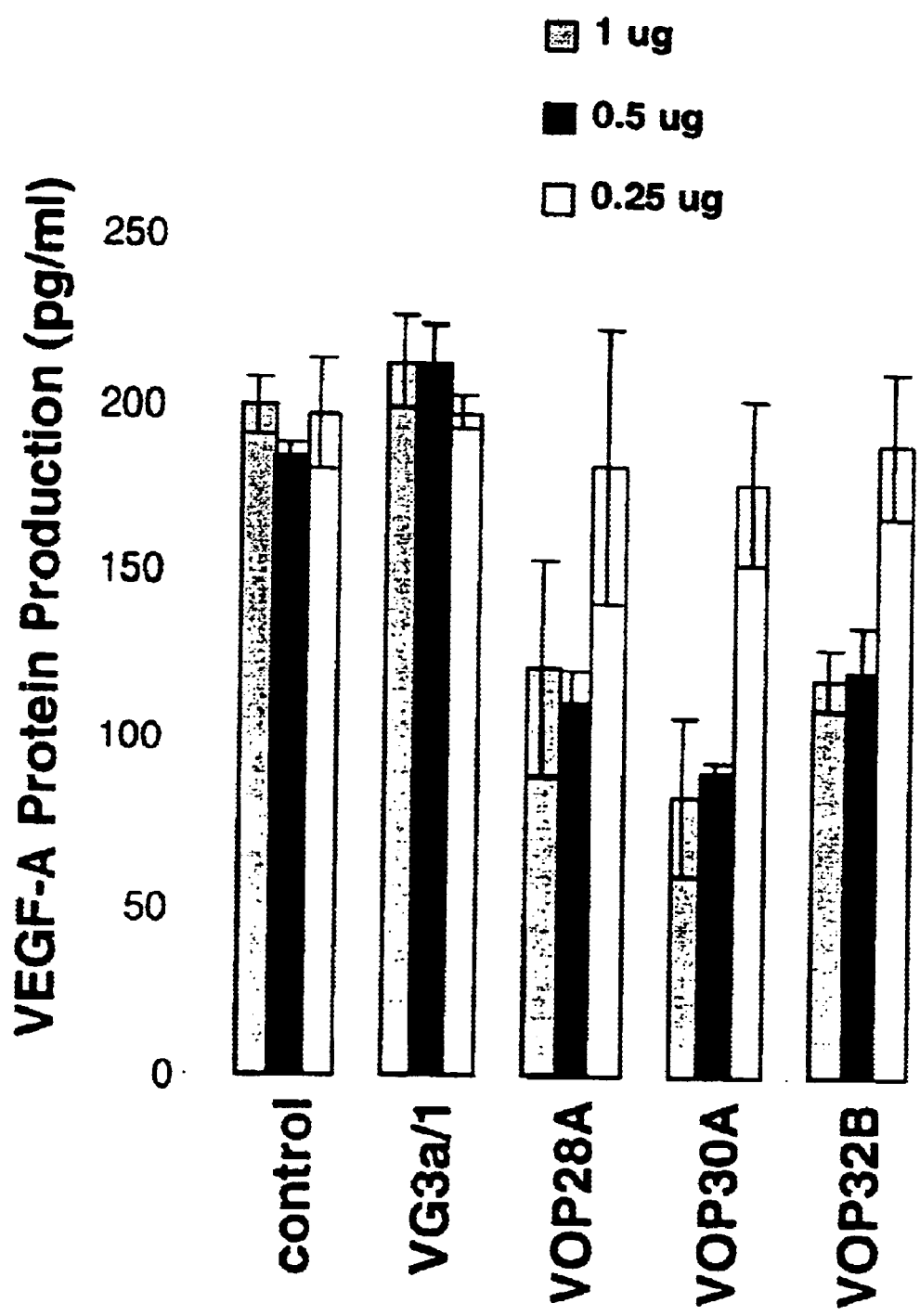
FIG. 14. Levels of VEGF-A protein in the culture medium of mouse MES13 cells that have been transfected with plasmids encoding different v-erbA/ZFP fusions. The different ZFP binding domains are indicated along the abscissa and are described in Example 9. For each plasmid, different concentrations of DNA were used for transfection, as indicated in the Figure. Control cells were transfected with vector plasmid, which lacked sequences encoding a ZFP fusion protein.

Mouse MES 13 cells were cultured, essentially as described in Example 9 (except that they were plated at ½ to ⅓ the density at which 293 cells were plated), and transfected with expression vectors encoding fusions of a v-erbA repression domain to each of the VOP28A, VOP30A and VOP32B binding domains, as described in Example 9. VEGF-A protein secreted into the culture medium of transfected cells was measured as described in Example 9. The results, shown in FIG. 14, indicate that proteins comprising a fusion of v-erbA to any of the three binding domains which bind in the mouse VEGF-A gene are effective in repressing VEGF-A expression in mouse cells. A fusion of v-erbA to VEGF3a/1 (which does not bind in the mouse VEGF-A gene) was used as a control, and shows no repression activity.

Example 13
Regulation of VEGF-A Gene Expression Using Fusions Between a Thyroid Hormone Receptor Ligand-Binding Domain and a Zinc Finger DNA-Binding Domain In this example, regulation of human VEGF-A gene expression by fusions between a ZFP DNA-binding domain and a thyroid hormone receptor (TR) ligand-binding domain was examined, and it was demonstrated that the TR ligand-binding domain acts as a ligand-dependent bifunctional domain.

Plasmids were constructed to encode fusions between amino acids 114–408 of the chicken thyroid hormone receptor α1 (which has a full-length amino acid sequence of 408 amino acids, GenBank Accession No. Y00987) and each of the VOP28A, VOP30A and VOP32B ZFP binding domains described in Example 9. Plasmid construction, culture and transfection of human 293 cells, and measurement of VEGF-A protein levels were conducted as described in Example 9. After transfection, each culture of transfected cells was divided into two portions. The first portion was cultured as described in Example 9; while T3 was added to a final concentration of 100 nM in the second portion.

Figure 15:
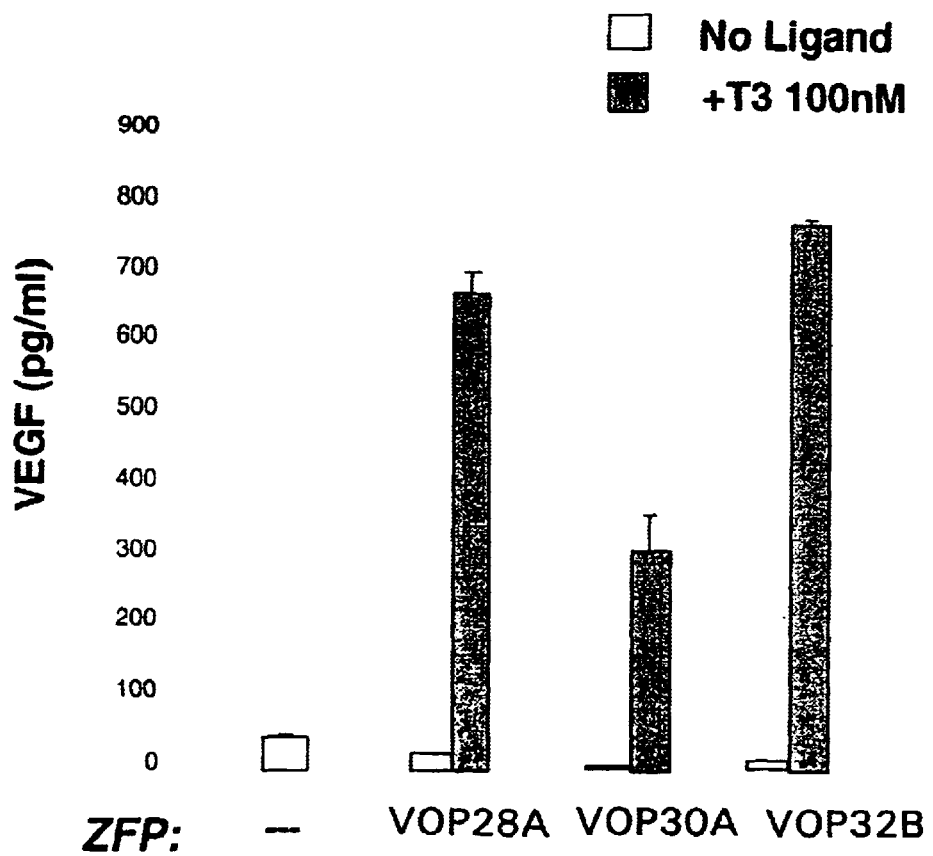
FIG. 15. Repression and ligand-dependent activation of human VEGF-A expression by TR/ZFP fusions. Human 293 cells were transfected with plasmids encoding fusions of the thyroid hormone receptor (amino acids 114–408) to different ZFP binding domains, as indicated along the abscissa. Transfected cells were cultured in medium with no additions, or in medium containing 100 nM 3,5,3'-triiodo-L-thyronine (T3), as indicated. VEGF-A levels in the culture medium of transfected cells are shown.

Results are shown in FIG. 15 and indicate that, in the absence of T3, TR/ZFP fusions targeted to the VEGF-A gene repress gene expression; while, in the presence of ligand (T3), the same TR/ZFP fusions activate VEGF-A expression up to 40-fold. Similar results, showing bifunctional, ligand-dependent regulation of VEGF-A gene expression by ZFP-TR fusions, were obtained in mouse MES13 cells.

Example 14
Repression of Human p16 Gene Expression

The human p 16 gene is a tumor suppressor gene involved in regulation of the cell cycle. In this example, repression of p16 expression, using several different repression domains, is shown.

HEK 293 cells were seeded to a concentration of $0.5 \times 10^6$ cells per well in 6-well plates. One day later, the cells were transfected (2 ug plasmid DNA in 7 ul LipofectAMINE 2000) with a plasmid encoding a ZFP-functional domain fusion. The ZFP binding domain used in the fusions, Cat18a, was designed (as described supra and in WO 98/53059; WO 98/53059; WO 98/53060 and co-owned WO 00 42219) to bind to a 9-nucleotide sequence (GTGGGGGGC, located between 75 and 83 nucleotides upstream of the transcription startsite disclosed by Hara et al. (1996) *Mol. Cell. Biol.* 16:859–867. Sequences encoding this binding domain were fused independently to sequences encoding the KRAB (Example 3, supra), v erbA (amino acids 223–556), and MBD2B (amino acids 149–411) repression domains.

Figure 16:
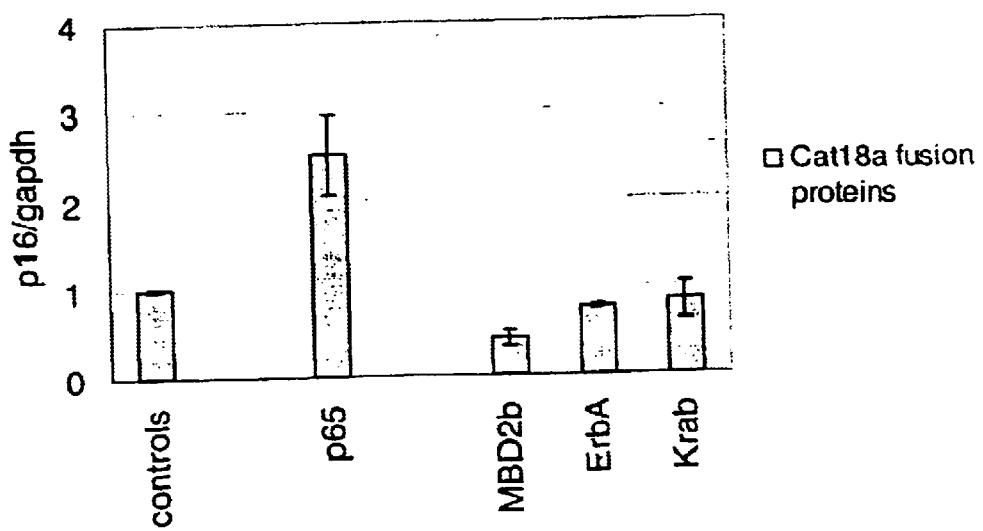
FIG. 16. Levels of p16 mRNA (normalized to GAPDH mRNA levels) in human 293 cells that had been transfected with plasmids encoding a fusion between a p16-targeted ZFP DNA binding domain and a KRAB, v-erbA or MBD2B repression domain (as indicated along the abscissa). Control cells were transfected with a vector that encoded a protein lacking a DNA-binding domain. Cells transfected with a plasmid encoding a fusion between a p65 activation domain and a p 16-targeted ZFP were also analyzed (indicated by "p65" along the abscissa).

Two days after transfection, cells were harvested, total RNA was isolated from the cells and the RNA was tested for p16 mRNA levels using a real-time quantitative amplification assay (Taqman®). The results, shown in FIG. 16, indicate repression of p16 transcription by fusion proteins containing a p16-targeted ZFP binding domain fused to KRAB, v-erbA or MBD2B.

It will be readily apparent to one of ordinary skill in the art, in light of the teachings disclosed herein, that certain changes and modifications may be made thereto without departing from the spirit or scope of the appended claims.

What is claimed is:

1. A method of modulating expression of an endogenous cellular gene in a cell, the method comprising the step of:
   contacting the cell with a first polynucleotide encoding a first zinc finger protein, wherein the first zinc finger protein is a fusion protein comprising a designed or selected zinc finger protein in operative linkage with a fimctional domain, further wherein the fusion protein binds to a first target site in the gene;
   thereby modulating expression of the endogenous cellular gene.

2. The method of claim 1, wherein the step of contacting further comprises contacting the cell with a second polynucleotide encoding a second zinc finger protein that binds a second target site in the endogenous cellular gene.

3. The method of claim 2, wherein the first and second target sites are adjacent.

4. The method of claim 3, wherein the first and second zinc finger proteins are covalently linked.

5. The method of claim 1, wherein the first zinc finger protein is a fusion protein comprising at least two regulatory domains.

6. The method of claim 3, wherein the first and second zinc finger proteins are fusion proteins, each comprising a functional domain.

7. The method of claim 6, wherein the first and second zinc finger proteins are fusion proteins, each comprising at least two functional domains.

8. The method of claim 1, wherein the cell is selected from the group consisting of an animal cell, a plant cell, a bacterial cell, a protozoal cell, or a fungal cell.

9. The method of claim 8, wherein the cell is a plant cell.

10. The method of claim 8, wherein the cell is a mammalian cell.

11. The method of claim 10, wherein the cell is a human cell.

12. The method of claim 1 wherein the expression of the endogenous cellular gene is repressed.

13. The method of claim 12, wherein the functional domain is selected from the group consisting of unliganded thyroid hormone receptor (TR), v-erbA, Dax and RBP.

14. The method of claim 1, wherein the expression of the endogenous cellular gene is activated.

15. The method of claim 14, wherein the functional domain is ligand-bound thyroid hormone receptor.

16. The method of claim 15, wherein the ligand is 3,5,3'-tiiodo-L-thyronine (T3).

17. The method of claim 1 wherein the functional domain is a bifunctional domain (BFD).

18. The method of claim 17, wherein the activity of the bifunctional domain is dependent upon interaction of the BFD with a second molecule.

19. The method of claim 18, wherein the BFD is selected from the group consisting of thyroid hormone receptor, retinoic acid receptor, estrogen receptor and glucocorticoid receptor.

20. The method of claim 18, wherein the second molecule is a protein.

21. The method of claim 18, wherein the second molecule is a small molecule.

22. The method of claim 19, wherein the second molecule is a small molecule.

23. The method of claim 22, wherein the small molecule is selected from the group consisting of thyroid hormone (T3), all-trans-retinoic acid, estradiol, tamoxifen, 4-hydroxy-tamoxifen, RU-486 and dexamethasone.

24. The method of claim 1, wherein sequences encoding the first zinc finger protein are operablylinked to a promoter, and wherein the first polynucleotide is administered to the cell in a lipid:nucleic acid complex or as naked nucleic acid.

25. The method of claim 24, wherein the promoter is an inducible promoter.

26. The method of claim 1, wherein sequences encoding the first zinc finger protein are contained in an expression vector and are operably linked to a promoter, and wherein the method further comprises the step of first administering the expression vector to the cell.

27. The method of claim 26, wherein the expression vector is a viral expression vector.

28. The method of claim 27, wherein the expression vector is selected from the group consisting of a retroviral expression vector, an adenoviral expression vector, and an AAV expression vector.

29. The method of claim 26, wherein the promoter is an inducible promoter.

30. The method of claim 1, wherein the first target site is upstream of a transcription initiation site of the endogenous cellular gene.

31. The method of claim 1, wherein the first target site is adjacent to a transcription initiation site of the endogenous cellular gene.

32. The method of claim 1, wherein the first target site is downstream of a transcription initiation site of the endogenous cellular gene.

33. The method of claim 1, wherein the zinc finger protein comprises an SP-1 backbone.

* * * * *